(12) United States Patent
Anderson et al.

(10) Patent No.: US 8,545,818 B2
(45) Date of Patent: *Oct. 1, 2013

(54) HAIR CARE COMPOSITIONS AND METHODS OF TREATING HAIR USING SAME

(75) Inventors: Daniel Griffith Anderson, Sudbury, MA (US); Amir Nashat, Newton, MA (US); Mitchell John DeRosa, Hyde Park, MA (US); David Thomas Puerta, Melrose, MA (US); Ronald P. McLaughlin, Reading, MA (US); Bryan Scott Akcasu, Burbank, CA (US); Susan Alice Williams, Natick, MA (US); Richard Matthew Ramirez, Wichita Falls, TX (US)

(73) Assignee: Living Proof, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/490,644

(22) Filed: Jun. 7, 2012

(65) Prior Publication Data

US 2012/0251471 A1    Oct. 4, 2012

Related U.S. Application Data

(63) Continuation of application No. 12/147,397, filed on Jun. 26, 2008, now Pat. No. 8,226,934.

(60) Provisional application No. 60/981,625, filed on Oct. 22, 2007, provisional application No. 60/981,632, filed on Oct. 22, 2007.

(51) Int. Cl.
*A61Q 5/06* (2006.01)
*A61Q 5/02* (2006.01)
*A61Q 5/12* (2006.01)

(52) U.S. Cl.
USPC ......... 424/47; 424/70.1; 424/70.2; 424/70.11

(58) Field of Classification Search
None
See application file for complete search history.

(56) References Cited

U.S. PATENT DOCUMENTS

| | | |
|---|---|---|
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer |
| 2,658,072 A | 11/1953 | Kosmin |
| 3,155,591 A | 11/1964 | Hilfer |
| 3,332,880 A | 7/1967 | Kessler et al. |
| 3,405,084 A | 10/1968 | Bohac et al. |
| 3,577,517 A | 5/1971 | Kubot et al. |
| 3,634,022 A | 1/1972 | Robbins et al. |
| 3,634,367 A | 1/1972 | Lang et al. |
| 3,676,550 A | 7/1972 | Anzuino |
| 3,726,288 A | 4/1973 | Nowak et al. |
| 3,810,977 A | 5/1974 | Levine et al. |
| 3,862,306 A | 1/1975 | Block et al. |
| 3,927,199 A | 12/1975 | Micchelli et al. |
| 3,929,678 A | 12/1975 | Laughlin et al. |
| 3,959,461 A | 5/1976 | Bailey et al. |
| 3,981,987 A | 9/1976 | Linke et al. |
| 3,993,744 A | 11/1976 | Cella et al. |
| 3,993,745 A | 11/1976 | Cella et al. |
| 4,013,786 A | 3/1977 | Cella et al. |
| 4,044,121 A | 8/1977 | Ko |
| 4,059,688 A | 11/1977 | Rosenberg et al. |
| 4,077,441 A | 3/1978 | Rosen et al. |
| 4,098,811 A | 7/1978 | Falk |
| 4,122,029 A | 10/1978 | Gee et al. |
| 4,164,562 A | 8/1979 | Nandagiri et al. |
| 4,176,176 A | 11/1979 | Cella et al. |
| 4,192,861 A | 3/1980 | Micchelli et al. |
| 4,196,190 A | 4/1980 | Gehman et al. |
| 4,237,253 A | 12/1980 | Jacquet et al. |
| 4,243,548 A | 1/1981 | Heeb et al. |
| 4,265,878 A | 5/1981 | Keil |
| 4,275,055 A | 6/1981 | Nachtigal et al. |
| 4,315,910 A | 2/1982 | Nowak, Jr. et al. |
| 4,348,380 A | 9/1982 | Jacquet et al. |
| 4,358,567 A | 11/1982 | Hayama et al. |
| 4,387,090 A | 6/1983 | Bolich, Jr. |
| 4,421,769 A | 12/1983 | Dixon et al. |
| 4,521,404 A | 6/1985 | Lorenz et al. |
| 4,543,249 A | 9/1985 | Nelson |
| 4,567,035 A | 1/1986 | Waxman et al. |
| 4,689,379 A | 8/1987 | Chuang |
| 4,767,613 A | 8/1988 | Nuber et al. |
| 4,778,675 A | 10/1988 | Vanlerberghe et al. |
| 4,803,067 A | 2/1989 | Brunetta et al. |
| 4,850,577 A | 7/1989 | Yamaoka |
| 4,874,604 A | 10/1989 | Sramek |
| 4,880,620 A | 11/1989 | Vanlerberghe et al. |
| 4,897,262 A | 1/1990 | Nandagiri et al. |
| 4,923,695 A | 5/1990 | Nowak, Jr. et al. |
| 4,954,336 A | 9/1990 | Chuang et al. |

(Continued)

FOREIGN PATENT DOCUMENTS

| | | |
|---|---|---|
| RU | 2266300 C2 | 6/2004 |
| RU | 2246929 C2 | 8/2004 |

(Continued)

OTHER PUBLICATIONS

Fisher, J.P. et al., "Photoinitiated Polymerization of Biomaterials", Annu. Rev. Mater. Res., vol. 31, pp. 171-181, 2001.

(Continued)

*Primary Examiner* — Jyothsna Venkat
(74) *Attorney, Agent, or Firm* — Fitzpatrick, Cella, Harper & Scinto

(57) ABSTRACT

The present invention provides kits and methods for treating hair on the scalp comprising non-toxic compositions providing beneficial effects on hair without employing high temperatures, free radical initiators or rinsing hair after applying the compositions.

9 Claims, No Drawings

(56) References Cited

U.S. PATENT DOCUMENTS

| | | | |
|---|---|---|---|
| 5,021,238 | A | 6/1991 | Martino et al. |
| 5,082,010 | A | 1/1992 | Skaryd et al. |
| 5,183,588 | A | 2/1993 | Salerno et al. |
| 5,183,589 | A | 2/1993 | Brunetta et al. |
| 5,206,298 | A | 4/1993 | Kawaguchi |
| 5,288,825 | A | 2/1994 | Toyooka et al. |
| 5,312,968 | A | 5/1994 | O'Lenick, Jr. et al. |
| 5,523,078 | A | 6/1996 | Baylin |
| 5,688,493 | A | 11/1997 | Sugawara et al. |
| 5,705,148 | A | 1/1998 | Bollens et al. |
| 5,738,879 | A | 4/1998 | Rine |
| 5,741,499 | A | 4/1998 | Arnauld et al. |
| 5,833,997 | A | 11/1998 | Mahieu et al. |
| 5,851,544 | A | 12/1998 | Penska et al. |
| 5,989,533 | A | 11/1999 | Deegan et al. |
| 6,156,296 | A | 12/2000 | Riedel et al. |
| 6,410,005 | B1 | 6/2002 | Galleguillos et al. |
| 6,419,937 | B1 | 7/2002 | Waldmann-Laue et al. |
| 6,455,058 | B1 | 9/2002 | Sun et al. |
| 6,602,495 | B2 | 8/2003 | Bergmann et al. |
| 6,653,353 | B2 | 11/2003 | Adams et al. |
| 6,706,674 | B2 | 3/2004 | Cincotta et al. |
| 6,939,922 | B2 | 9/2005 | Beckley et al. |
| 7,135,168 | B2 | 11/2006 | Miczewski et al. |
| 7,763,240 | B2 * | 7/2010 | Anderson et al. ............ 424/70.1 |
| 7,785,575 | B2 * | 8/2010 | Anderson et al. ............ 424/70.1 |
| 8,226,934 | B2 * | 7/2012 | Anderson et al. .......... 424/70.11 |
| 8,318,138 | B2 * | 11/2012 | Anderson et al. ............... 424/47 |
| 2002/0086167 | A1 * | 7/2002 | Hayashi et al. ............... 428/447 |
| 2002/0197227 | A1 | 12/2002 | Scholz |
| 2003/0147830 | A1 | 8/2003 | Phillips et al. |
| 2004/0040095 | A1 | 3/2004 | King et al. |
| 2006/0104919 | A1 * | 5/2006 | Novak ............................ 424/47 |
| 2007/0141002 | A1 | 6/2007 | Montezinos et al. |
| 2007/0197704 | A1 | 8/2007 | Walter et al. |
| 2008/0066773 | A1 | 3/2008 | Anderson et al. |

FOREIGN PATENT DOCUMENTS

| | | |
|---|---|---|
| WO | 93/16809 A2 | 9/1993 |
| WO | 0251370 A1 | 7/2002 |
| WO | 02076412 A2 | 10/2002 |

OTHER PUBLICATIONS

"Best of Beauty", Allure magazine, pp. 214, 216, 218, 220, and 222, Oct. 2008.
Bottle label for "TruLift, Stop the Frizz, Anti-frizz Styling Cream for Thick to Coarse Hair," 4 fl. oz., 2009.
Print out entitled, "2009 Innovation Edison Best New Products of the Year," printed from http://www.edisonawards.com/09awards-nominees.hp, 2 pages, 2009.
Non-Final Office Action in U.S. Appl. No. 12/841,724, dated Nov. 8, 2011.
Final Office Action in U.S. Appl. No. 12/420,539, dated Mar. 24, 2010.
Non-Final Office Action in U.S. Appl. No. 12/420,539, dated Jan. 4, 2010.
Written Opinion in Singapore Appln. No. 201002038-6, dated Jul. 7, 2011.
Restriction Requirement in U.S. Appl. No. 12/404,193, dated Sep. 18, 2009.
Non-Final Office Action in U.S. Appl. No. 12/404,193, dated Jan. 4, 2010.
Notice of Allowance in U.S. Appl. No. 12/404,193, dated Jun. 25, 2010.
Non-Final Office Action in U.S. Appl. No. 12/147,397, dated Aug. 29, 2011.
Notice of Allowance in U.S. Appl. No. 12/147,397, dated Feb. 14, 2012.
Notice of Allowance in U.S. Appl. No. 12/420,539, dated Jun. 14, 2010.
Restriction Requirement in U.S. Appl. No. 12/420,539, dated Sep. 18, 2009.
Restriction Requirment in U.S. Appl. No. 12/797,141, dated Jun. 22, 2011.
Restriction Requirement in U.S. Appl. No. 12/841,724, dated Jul. 18, 2011.
International Preliminary Report on Patentability of PCT/US2008/080819, dated Apr. 27, 2010.
International Search Report of PCT/US2008/080819, dated Dec. 29, 2008.
Non-Final Office Action in U.S. Appl. No. 12/797,141, dated Oct. 25, 2011.
Final Office Action in U.S. Appl. No. 12/841,724, dated May 9, 2012.
Office Action in Russian Application No. 2010112584, dated Jun. 25, 2012.
Restriction Requirement in U.S. Appl. No. 12/841,486, dated Dec. 16, 2011.
Non-Final Office Action in U.S. Appl. No. 12/841,486, dated Apr. 11, 2012.
Non-Final Office Action in U.S. Appl. No. 12/797,141, dated Mar. 28, 2013.
Final Office Action in U.S. Appl. No. 12/797,141, dated Jul. 11, 2012.
Non-Final Office Action in U.S. Appl. No. 12/841,724, dated Mar. 29, 2013.

* cited by examiner

HAIR CARE COMPOSITIONS AND METHODS OF TREATING HAIR USING SAME

This application is a continuation of U.S. application Ser. No. 12/147,397, filed Jun. 26, 2008, which claims the benefit of U.S. Provisional Application No. 60/981,625, filed Oct. 22, 2007, and U.S. Provisional Application No. 60/981,632, filed Oct. 22, 2007. The entire contents of all the above-mentioned applications are herein incorporated by reference.

BACKGROUND OF THE INVENTION

1. Field of the Invention

The present invention relates to compositions, kits and methods for treating hair. More particularly, the present invention includes compositions, kits and methods for treating hair using compounds described below, but without agents for effecting polymerization. The inventive compositions, kits and methods may also be used on hair other than on the scalp. In addition, the inventive compositions, kits and methods may be used on animals other than humans, including on the hair or fur of domesticated animals, including on cats and dogs.

2. Background of the Invention

The hair care industry is a multi-billion dollar industry in the United States alone. The industry includes the development, production, and marketing of a large array of products for hair care, including shampoos, gels, mousses, lotions, sprays, conditioners, coloring products, pomades, serums, waxes, and repair products. Most of these products utilize pre-formed polymers developed to impart a desired characteristic upon application to a user's hair. For example, polymers are used to give hair shine, style hair, preserve hair style, give hair a desired texture or feel, enhance hair color, condition hair, dry hair so it sets quickly, straighten or smoothen hair, soften hair, strengthen hair, make hard-to-treat hair manageable, enhance optical properties, provide hold to hair, provide frizz control and/or to repair damaged hair.

Existing hair care treatments, however, suffer from numerous limitations. One problem common to many hair care products is poor efficacy and longevity. For example, existing hair care treatments are not robust and can lose their efficacy over the course of a day. Many treatments lose their efficacy upon exposure to water or excess humidity. In addition, many hair treatments weigh down hair, flake off, leave unsightly residues, fail to dry and set quickly, do not provide adequate hold, and are not effective for hard-to-treat hair (e.g., naturally curly hair). Treatments have been developed which overcome some of these issues; however, they typically involve permanently treating the hair with reducing and/or oxidizing agents which can damage hair. Thus, there remains a need for hair treatments that withstand the rigors of a typical user's daily routine and can maintain efficacy in a variety of environments without damaging hair fibers. In addition, hair care products which are designed to protect hair or deliver agents which improve hair strength, shine, color, and arrangement suffer from similar limitations as they also exhibit poor efficacy and longevity requiring daily application. It is preferable that a hair treatment be long lasting, not weigh down hair, not flake, and not leave any undesirable residues. Furthermore, the hair treatment should preferably dry and set relatively quickly, provide adequate hold, and be able to manage hard-to-treat hair.

SUMMARY OF THE INVENTION

As described herein, it has been discovered that certain organic chemical compounds, such as small molecules, applied to hair produce effects and characteristics desired by hair product consumers. The compounds are preferably not polymers such as those typically used in hair care products. In certain embodiments, the organic compounds are fluorinated. In certain embodiments, the organic compounds are chlorinated. In certain embodiments, a combination of compounds described herein are used to treat hair. The compositions, kits and methods of the present invention afford numerous beneficial effects that are especially desired for treating hair on the scalp, including: (1) controlling moisture penetration into the hair (frizz control), (2) providing a soft feel to the hair, without a harsh feeling (conditioning), (3) increasing the shine of the hair, (4) enhancing the hair's color, (5) avoiding the feeling of stickiness to the hair (and consequently resisting accumulation of dirt to the hair), (6) dries and sets quickly, (7) can help generate and or preserve the style of the hair, (8) adding strength to the hair, (9) leaving a low amount of residue (are "weightless"), (10) do not flake off the hair, (11) lasting over the course of more than one day, even more than 5 days, (12) affecting, including reducing, the surface energy of the hair (and thereby affording quicker drying of hair), (13) affording manageability for hard-to-treat hair, as well as repairing damaged hair, (14) providing hold, and (15) providing shape.

The present invention provides novel cosmetic hair care compositions for use on hair. The compositions include an active hair care ingredient as described herein and in U.S. patent application, U.S. Ser. No. 11/734,425, filed Apr. 12, 2007, which is incorporated herein by reference for the monomers recited therein, and a cosmetically acceptable excipient. Cosmetically acceptable excipients include preservatives, antioxidants, chelating agents, sunscreen agents, vitamins, dyes, hair coloring agents, proteins, amino acids, plant extracts, humectants, fragrances, perfumes, oils, emollients, lubricants, butters, penetrants, thickeners, viscosity modifiers, polymers, resins, hair fixatives, film formers, surfactants, detergents, emulsifiers, opacifying agents, volatiles, propellants, liquid vehicles, carriers, carriers, salts, pH adjusting agents, neutralizing agents, buffers, hair conditioning agents, anti-static agents, anti-frizz agents, anti-dandruff agents, hair waving agents, hair straightening agents, relaxers, absorbents, and combinations thereof. Examples and appropriate amounts of each of these categories of cosmetically acceptable excipients is described herein. In certain embodiments, the cosmetic hair care compositions include at least two or more cosmetically acceptable excipients. In certain embodiments, the cosmetic hair care composition simply includes the active hair care ingredient and a cosmetically acceptable excipient that is volatile, leaving only the active ingredient on the subject's hair. The inventive hair care compositions include shampoos, conditioners, mousses, gels, hair sprays, creams, pomades, serums, waxes, coloring compositions, styling compositions, repair compositions, etc.

The present invention also provides novel compositions that can be used to aid in the lubrication of hair to assist in shaving any part of the body, for example, the beard, the legs and the underarms.

The present invention also provides a method of treating hair on the scalp comprising the step of: applying to the hair a non-toxic composition comprising a compound of formula (I):

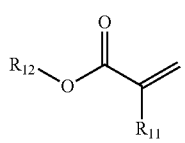

wherein
- $R_{11}$ is hydrogen or methyl optionally substituted with one or more halogen; and
- $R_{12}$ is selected from the group consisting of cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; and substituted or unsubstituted heteroaryl; and wherein the method does not employ a step consisting of (i) heating hair with a heating source above about 160° C. after applying the non-toxic composition; (ii) applying a composition containing more than about 0.1% weight/weight of a free radical initiator selected from the group consisting of a heat-activated initiator that is activated at or above ambient temperature and an initiator that is active at ambient temperature; or (iii) both (i) and (ii).

The present invention also provides a method of treating hair on the scalp comprising the step of applying to the hair a non-toxic composition comprising a compound of formula (I) as described above, and wherein the method does not employ a step consisting of rinsing the hair after applying the compound.

The present invention also provides a method of treating hair on the scalp comprising the step of applying to the hair a non-toxic composition comprising a compound of formula (I) as described above, and wherein the method does not employ a step consisting of (i) rinsing the hair after applying the compound; (ii) applying a composition containing more than about 0.1% weight/weight of a free radical initiator selected from the group consisting of a heat-activated initiator that is activated at or above ambient temperature and an initiator that is active at ambient temperature; or (iii) both (i) and (ii).

The present invention also provides a method of treating hair on the scalp comprising the step of applying to the hair a non-toxic composition comprising a compound of formula (I) as described above under conditions wherein there is no substantial polymerization of the compound.

The present invention also provides a kit for treating hair on the scalp comprising one or more non-toxic compositions, wherein at least one non-toxic composition comprises a compound of formula (I) above; and instructions for use of the kit, wherein said instructions do not direct (i) heating of the hair with a heating source above about 160° C. after applying the non-toxic composition; (ii) applying a composition containing more than about 0.1% weight/weight of a free radical initiator selected from the group consisting of a heat-activated initiator that is activated at or above ambient temperature and an initiator that is active at ambient temperature; or (iii) both (i) and (ii).

The present invention also provides a kit for treating hair on the scalp comprising one or more non-toxic compositions, wherein at least one non-toxic composition comprises a compound of formula (I) above, and instructions for use of the kit, wherein the instructions do not direct rinsing the hair after applying the compound.

The present invention also provides a kit for treating hair on the scalp comprising one or more non-toxic compositions, wherein at least one non-toxic composition comprises a compound of formula (I) above, and instructions for use of the kit, wherein the instructions do not direct (i) rinsing the hair after applying said compound; (ii) applying a composition containing more than about 0.1% weight/weight of a free radical initiator selected from the group consisting of a heat-activated initiator that is activated at or above ambient temperature and an initiator that is active at ambient temperature; or (iii) both (i) and (ii).

The present invention also provides a kit for treating hair on the scalp comprising one or more non-toxic compositions, wherein at least one non-toxic composition comprises a compound of formula (I) above, and instructions for use of the kit, wherein following the instructions results in no substantial polymerization of the compound.

The invention also provides a method of formulating an inventive cosmetic hair care composition.

DETAILED DESCRIPTION OF THE INVENTION

The present invention provides novel cosmetic hair care compositions comprising fluorinated, as well as non-fluorinated, chlorinated, organic chemical compounds, some of which are capable of polymerization, but do not necessarily substantially polymerize after application to hair. It has been discovered that the application of certain of these active hair care ingredients, and cosmetic hair care compositions thereof, to hair leads to producing desirable effects on a subject's hair referred to above, including: (1) controlling moisture penetration into the hair (frizz control), (2) providing a soft feel to the hair, without a harsh feeling (conditioning), (3) increasing the shine of the hair, (4) enhancing the hair's color, (5) avoiding the feeling of stickiness to the hair (and consequently resisting accumulation of dirt to the hair), (6) dries and sets quickly, (7) can help generate and or preserve the style of the hair, (8) adding strength to the hair, (9) leaving a low amount of residue (are "weightless"), (10) do not flake off the hair, (11) lasting over the course of more than one day, even more than 5 days, (12) affecting, including reducing, the surface energy of the hair (and thereby affording quicker drying of hair), (13) affording manageability for hard-to-treat hair, as well as repairing damaged hair, (14) providing hold, and (15) providing shape. The active hair care ingredients are typically non-toxic, low molecular weight, organic compounds. The inventive compositions can also be used to affect the color, condition, surface energy, style, strength, shine, and/or optical properties of the treated hair. The hair treatment using the inventive compositions is preferably robust and long-lasting, resisting removal and/or degradation by humidity, brushing, or other factors.

The present invention also provides novel compositions that can be used to aid in the lubrication of hair to assist in shaving any part of the body, for example, the beard, the legs and the underarms.

The present invention also provides a method of treating hair on the scalp comprising the step of: applying to the hair a non-toxic composition comprising a compound of formula (I):

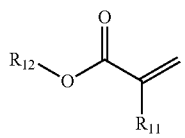

wherein
$R_{11}$ is hydrogen or methyl optionally substituted with a halogen; and
$R_{12}$ is selected from the group consisting of cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; and substituted or unsubstituted heteroaryl; and wherein said method does not employ a step consisting of (i) heating hair with a heating source above about 160° C. after applying said non-toxic composition; (ii) applying a composition containing more than about 0.1% weight/weight of a free radical initiator selected from the group consisting of a heat-activated initiator that is activated at or above ambient temperature and an initiator that is active at ambient temperature; or (iii) both (i) and (ii). In step (ii) above, a composition refers to either (a) the non-toxic composition comprising a compound of formula (I) above containing more than about 0.1% weight/weight of a free radical initiator selected from the group consisting of a heat-activated initiator that is activated at or above ambient temperature and an initiator that is active at ambient temperature or (b) another composition containing more than about 0.1% weight/weight of a free radical initiator selected from the group consisting of a heat-activated initiator that is activated at or above ambient temperature and an initiator that is active at ambient temperature, wherein the another composition is applied simultaneously or subsequent to the application of the non-toxic composition.

In a certain embodiment, the method of the present invention preferably does not employ a step consisting of applying a composition containing more than about 0.01% weight/weight, even more preferably, more than about 0.001% weight/weight of a free radical initiator selected from the group consisting of a heat-activated initiator that is activated at or above ambient temperature and an initiator that is active at ambient temperature.

In a certain embodiment, the method of the present invention preferably does not further employ a step consisting of applying a composition containing more than about 0.1% weight/weight, preferably, more than about 0.01% weight/weight, and even more preferably, more than about 0.001% weight/weight of a uv-activated free radical initiator that is activated under ambient light. In the step above, a composition refers to either (a) the non-toxic composition comprising a compound of formula (I) above containing more than about 0.1% weight/weight, preferably, more than about 0.01% weight/weight, and even more preferably, more than about 0.001% weight/weight of a uv-activated free radical initiator that is activated under ambient light or (b) another composition containing more than about 0.1% weight/weight, preferably, more than about 0.01% weight/weight, and even more preferably, more than about 0.001% weight/weight of a uv-activated free radical initiator that is activated under ambient light, wherein the another composition is applied simultaneously or subsequent to the application of the non-toxic composition.

In a certain embodiment, the method of the present invention preferably does not employ a step consisting of heating hair with a heating source above about 120° C. after applying the non-toxic composition.

In a preferred embodiment, $R_{12}$ of formula (I) above contains at least one halogen, more preferably, $R_{12}$ contains at least one fluorine.

In a preferred embodiment, the compound of formula (I) above is selected from the group consisting of 1,1,1,3,3,3-hexafluoroisopropyl 2-fluoroacrylate; 1,1,1,3,3,3-hexafluoroisopropyl 2-fluoromethacrylate; 1,1,1,3,3,3-hexafluoroisopropyl acrylate; 1,1,1,3,3,3-hexafluoroisopropyl methacrylate; 2,2,3,3,4,4,5,5-octafluoro-1,6-hexyl dimethacrylate; 2,2,3,3,4,4,5,5-octafluoro-1,6-hexyl diacrylate; methyl pentafluoromethacrylate; methyl pentafluoroacrylate; methyl trifluoroacrylate; methyl trifluoromethacrylate; heptafluoroisopropyl acrylate; heptafluoroisopropyl methacrylate; hexafluoro-2-methylisopropyl acrylate; hexafluoro-2-methylisopropyl methacrylate; pentafluorobenzyl acrylate; pentafluorobenzyl methacrylate; tert-butyl-2-(trifluoromethyl)acrylate; tert-butyl-2-(trifluoromethyl)methacrylate; 1H,1H,1H-eicosafluoroundecyl acrylate; 1H,1H,1H-eicosafluoroundecyl methacrylate; 2,2,3,3,4,4,5,5-octafluoro-1,6-hexyldiacrylate; 2,2,3,3,4,4,5,5-octafluoro-1,6-hexyldimethacrylate; 2,2,3,3,4,4,5,5-octafluoropentyl methacrylate; 2,2,3,3,4,4,5,5-octafluoropentyl acrylate; 2,2,3,3,4,4-hexafluoro-1,5-pentyl diacrylate; 2,2,3,3,4,4-hexafluoro-1,5-pentyl dimethacrylate; 2,3-dichloro-1-propyl acrylate; 2,3-dichloro-1-propyl methacrylate; 1-3-dichloro-2-propyl acrylate; 1-3-dichloro-2-propyl methacrylate; 2,2,2-trichloroethyl acrylate; 2,2,2-trichloroethyl methacrylate; 2-chloroethyl acrylate; 2-chloroethyl methacrylate; 2,2,2-tribromoethyl acrylate; 2,2,2-tribromoethyl methacrylate; 2,2,2-tribromoethyl acrylate.

In a preferred embodiment, the compound of formula (I) above is

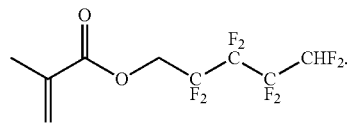

Octafluoropentyl methacrylate (OFPMA)

The preferred embodiments in features described herein with respect to the non-toxic composition comprising a compound of formula (I) described above are all applicable to each individual compound described above. For example, the method of the present invention wherein the method does not employ a step of applying a composition containing more than about 0.01% weight/weight of a free radical initiator selected from the group consisting of a heat-activated initiator that is activated at or above ambient temperature and an initiator that is active at ambient temperature, applies to each individual compound described above. For example, method of the present invention wherein the method does not employ a step consisting of heating hair with a heating source above about 120° C. after applying the non-toxic composition applies to each individual compound described above.

The present invention also provides a method of treating hair on the scalp comprising the step of applying to the hair a non-toxic composition comprising a compound of formula (I) described above, and wherein the method does not employ a step consisting of rinsing the hair after applying the compound. Preferably, the method does not employ a step consisting of rinsing the hair within at least 30 minutes to several hours, for example, about 1, 2, 3, or 4 hours applying the compound.

The present invention also provides a method of treating hair on the scalp comprising the step of applying to the hair a non-toxic composition comprising a compound of formula (I) as described above, and wherein the method does not employ a step consisting of (i) rinsing the hair after applying the compound; (ii) applying a composition containing more than about 0.1% weight/weight, preferably, more than about 0.01% weight/weight, even more preferably more than about 0.001% weight/weight of a free radical initiator selected from the group consisting of a heat-activated initiator that is activated at or above ambient temperature and an initiator that is active at ambient temperature; or (iii) both (i) and (ii).

The present invention also provides a method of treating hair on the scalp comprising the step of applying to the hair a non-toxic composition comprising a compound of formula (I) as described above under conditions wherein there is no substantial polymerization of the compound.

There are many means for providing that no substantial polymerization of the monomer compound is occurring, including the addition of one or more polymerization inhibitors, the addition of one or more reducing agents, waiting for a sufficient period of time until there are no longer an appreciable number of free-radicals by virtue of them terminating, cooling the contents of the reactor to limit the reactivity of the free-radicals, and combinations thereof. A preferred means involves the addition of one or more polymerization inhibitors such as, for example, N,N-diethylhydroxylamine, N-nitrosodiphenylamine, 2,4-dinitrophenylhydrazine, p-phenylenediamine, phenathiazine, alloocimene, triethyl phosphite, 4-nitrosophenol, 2-nitrophenol, p-aminophenol, 4-hydroxy-TEMPO (also known as 4-hydroxy-2,2,6,6, tetramethylpiperidinyloxy, free radical), hydroquinone, p-methoxyhydroquinone, tert-butyl-p-hydroquinone, 2,5-di-tert-butyl-p-hydroquinone, 1,4-naphthalenediol, 4-tert butyl catechol, copper sulfate, copper nitrate, cresol and phenol. When used, the polymerization inhibitors or reducing agents are added in effective amount to substantially stop any polymerization, generally from 25 to 5,000 parts per million ("ppm"), preferably from 50 to 3,500 ppm based on polymer solids.

Yet another embodiment of the present invention provides a composition for treating hair consisting essentially of a compound of formula (I) as described above. This compound as described herein lacks substantial presence of a free radical initiator, a polymerization initiator or a polymerization catalyst that causes substantial polymerization.

Yet another embodiment of the present invention provides a composition that can be used to aid in the lubrication of hair to assist in shaving any part of the body, for example, the beard, the legs and the underarms, consisting essentially of a compound of formula (I) as described above. This compound as described herein lacks substantial presence of a free radical initiator, a polymerization initiator or a polymerization catalyst that causes substantial polymerization.

The present invention also provides kits for use in treating hair based on the inventive hair care formulations. In another aspect, the present invention provides kits including the inventive cosmetic hair care compositions and instructions for using the composition in treating hair. The kit may include enough of the formulation for one use or multiple uses (e.g., approximately 2, 3, 4, 5, 10, 15, 20, 25, or 50). The kit may include any or all of the following components: hair care formulation, tube, bottle, spray bottle, brush, hair dryer, containers, and instructions for use. The formulations of the kit may be packaged as lotions, mousses, solutions, gels, pomades, serums, waxes, emulsions, suspensions, pumpable hair sprays, aerosol sprays, and non-aerosol sprays (e.g., atomisers). Hair care formulations are typically conveniently packaged in a suitable container for shipping and/or application of the composition. For example, a composition may be provided in a pump spray bottle or spray can. In certain embodiments, the kits are conveniently packaged for use by the end use along with instructions for use in accordance with the present invention. In certain embodiments, the kit is tailored for producing a desired characteristic in the treated hair. The kit may also include other hair care products including dyes, shampoos, conditioners, gels, mousses, pomades, serums, waxes, etc. The kit may also include all the materials needed for treating hair with the inventive hair care composition. The kit may include the materials conveniently packaged for use in a hair stylist's shop or for home use.

The present invention also provides a kit for treating hair on the scalp comprising one or more non-toxic compositions, wherein at least one non-toxic composition comprises a compound of formula (I) above; and instructions for use of the kit, wherein said instructions do not direct (i) heating of said hair with a heating source above about 160° C. after applying said non-toxic composition; (ii) applying a composition containing more than about 0.1% weight/weight of a free radical initiator selected from the group consisting of a heat-activated initiator that is activated at or above ambient temperature and an initiator that is active at ambient temperature; or (iii) both (i) and (ii). In instructions (ii) above, a composition refers to either (a) the non-toxic composition comprising a compound of formula (I) above containing more than about 0.1% weight/weight of a free radical initiator selected from the group consisting of a heat-activated initiator that is activated at or above ambient temperature and an initiator that is active at ambient temperature or (b) another composition containing more than about 0.1% weight/weight of a free radical initiator selected from the group consisting of a heat-activated initiator that is activated at or above ambient temperature and an initiator that is active at ambient temperature, wherein the another composition is applied simultaneously or subsequent to the application of the non-toxic composition.

It will be understood that the preferred embodiments of the kits of the present invention will include the preferred compounds of formula (I) and the limitations relating to the free radical initiator, the concentrations of the free radical initiator, and temperatures of the heating source as described herein for the methods of the present invention.

In a certain embodiment, the instructions for use of the kit of the present invention preferably does not direct applying a composition containing more than about 0.01% weight/weight, even more preferably, more than about 0.001% weight/weight of a free radical initiator selected from the group consisting of a heat-activated initiator that is activated at or above ambient temperature and an initiator that is active at ambient temperature.

In a certain embodiment, the instructions for use of the kit of the present invention does not further direct applying a composition containing more than about 0.1% weight/weight, preferably, more than about 0.01% weight/weight, and even more preferably, more than about 0.001% weight/weight of a uv-activated free radical initiator that is activated under ambient light. In the instructions above, a composition refers to either (a) the non-toxic composition comprising a compound of formula (I) above containing more than about 0.1% weight/weight, preferably, more than about 0.01% weight/weight, and even more preferably, more than about 0.001% weight/weight of a uv-activated free radical initiator that is activated under ambient light or (b) another composition containing more than about 0.1% weight/weight, preferably, more than about 0.01% weight/weight, and even more preferably, more than about 0.001% weight/weight of a uv-activated free radical initiator that is activated under ambient light, wherein the another composition is applied simultaneously or subsequent to the application of the non-toxic composition.

In a certain embodiment, the instructions for use of the kit of the present invention preferably does direct heating hair with a heating source above about 120° C. after applying the non-toxic composition.

The present invention also provides a kit for treating hair on the scalp comprising one or more non-toxic compositions, wherein at least one non-toxic composition comprises a compound of formula (I) above, and instructions for use of the kit, wherein the instructions do not direct rinsing the hair after applying the compound. Preferably, the instructions do not direct rinsing the hair within at least 30 minutes to several hours, for example, about 1, 2, 3, or 4 hours applying the compound.

The present invention also provides a kit for treating hair on the scalp comprising one or more non-toxic compositions, wherein at least one non-toxic composition comprises a compound of formula (I) above, and instructions for use of the kit, wherein the instructions do not direct (i) rinsing the hair after applying the compound; (ii) applying a composition containing more than about 0.1% weight/weight, preferably, more than about 0.01% weight/weight, even more preferably more than about 0.001% weight/weight of a free radical initiator selected from the group consisting of a heat-activated initiator that is activated at or above ambient temperature and an initiator that is active at ambient temperature; or (iii) both (i) and (ii).

The present invention also provides a kit for treating hair on the scalp comprising one or more non-toxic compositions, wherein at least one non-toxic composition comprises a compound of formula (I) above, and instructions for use of the kit, wherein following the instructions results in no substantial polymerization of the compound.

Yet another embodiment of the present invention provides a composition comprising a compound selected from the group consisting of 1,1,1,3,3,3-hexafluoroisopropyl 2-fluoroacrylate; 1,1,1,3,3,3-hexafluoroisopropyl 2-fluoromethacrylate; 1,1,1,3,3,3-hexafluoroisopropyl acrylate; 1,1,1,3,3,3-hexafluoroisopropyl methacrylate; 2,2,3,3,4,4,5,5-octafluoro-1,6-hexyl dimethacrylate; 2,2,3,3,4,4,5,5-octafluoro-1,6-hexyl diacrylate; methyl pentafluoromethacrylate; methyl pentafluoroacrylate; methyl trifluoroacrylate; methyl trifluoromethacrylate; heptafluoroisopropyl acrylate; heptafluoroisopropyl methacrylate; hexafluoroisopropyl crotonate; hexafluoro-2-methylisopropyl acrylate; hexafluoro-2-methylisopropyl methacrylate; 1,1,1,3,3,3-hexafluoroisopropyl methacrylate; 1,1,1,3,3,3-hexafluoroisopropyl acrylate; 1,1,1,3,3,3-hexafluoroisopropyl dimethacrylate; 1,1,1,3,3,3-hexafluoroisopropyl diacrylate; pentafluorobenzyl acrylate; pentafluorobenzyl methacrylate; tert-butyl-2-(trifluoromethyl)acrylate; tert-butyl-2-(trifluoromethyl) methacrylate; 1H,1H,1H-eicosafluoroundecyl acrylate; 1H,1H,1H-eicosafluoroundecyl methacrylate; 2,2,3,3,4,4,5,5-octafluoro-1,6-hexyldiacrylate; 2,2,3,3,4,4,5,5-octafluoro-1,6-hexyldimethacrylate; 2,2,3,3,4,4,5,5-octafluoropentyl methacrylate; 2,2,3,3,4,4,5,5-octafluoropentyl acrylate; 2,2,3,3,4,4-hexafluoro-1,5-pentyl diacrylate; 2,2,3,3,4,4-hexafluoro-1,5-pentyl dimethacrylate; 2,3-dichloro-1-propyl acrylate; 2,3-dichloro-1-propyl methacrylate; 1-3-dichloro-2-propyl acrylate; 1-3-dichloro-2-propyl methacrylate; 2,2,2-trichloroethyl acrylate; 2,2,2-trichloroethyl methacrylate; 2-chloroethyl acrylate; 2-chloroethyl methacrylate; 2,2,2-tribromoethyl acrylate; 2,2,2-tribromoethyl methacrylate; 2,2,2-tribromoethyl methacrylate; and 2,2,2-tribromoethyl acrylate.

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, E- and Z-isomers, R- and S-enantiomers, diastereomers, (d)-isomers, (l)-isomers, (−)- and (+)-isomers, racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term acyl as used herein refers to a group having the general formula —C(O)R, where R is alkyl, alkenyl, alkynyl, aryl, carbocylic, heterocyclic, or aromatic heterocyclic. An example of an acyl group is acetyl.

The term aliphatic, as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

The term alkyl as used herein refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-10 carbon atoms. In another embodiment, the alkyl group employed contains 1-8 carbon atoms. In still other embodiments, the alkyl group contains 1-6 carbon atoms. In yet another embodiments, the alkyl group contains 1-4 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents.

The term alkoxy as used herein refers to a saturated (i.e., alkyl-O—) or unsaturated (i.e., alkenyl-O— and alkynyl-O—) group attached to the parent molecular moiety through an oxygen atom. In certain embodiments, the alkyl group contains 1-20 aliphatic carbon atoms. In certain other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples include, but are not limited to, methoxy, ethoxy, propoxy, isopropoxy, n-butoxy, tert-butoxy, i-butoxy, sec-butoxy, neopentoxy, n-hexoxy, and the like.

The term alkenyl denotes a monovalent group derived from a hydrocarbon moiety having at least one carbon-carbon double bond by the removal of a single hydrogen atom. In certain embodiments, the alkenyl group employed in the invention contains 1-20 carbon atoms. In some embodiments, the alkenyl group employed in the invention contains 1-10 carbon atoms. In another embodiment, the alkenyl group employed contains 1-8 carbon atoms. In still other embodiments, the alkenyl group contains 1-6 carbon atoms. In yet another embodiment, the alkenyl group contains 1-4 carbons. Alkenyl groups include, for example, ethenyl, propenyl, butenyl, 1-methyl-2-buten-1-yl, and the like.

The term alkynyl as used herein refers to a monovalent group derived form a hydrocarbon having at least one carbon-carbon triple bond by the removal of a single hydrogen atom. In certain embodiments, the alkynyl group employed in the invention contains 1-20 carbon atoms. In some embodiments, the alkynyl group employed in the invention contains 1-10 carbon atoms. In another embodiment, the alkynyl group employed contains 1-8 carbon atoms. In still other embodiments, the alkynyl group contains 1-6 carbon atoms. Representative alkynyl groups include, but are not limited to, ethynyl, 2-propynyl (propargyl), 1-propynyl, and the like.

The term alkylamino, dialkylamino, and trialkylamino as used herein refers to one, two, or three, respectively, alkyl groups, as previously defined, attached to the parent molecular moiety through a nitrogen atom. The term alkylamino refers to a group having the structure —NHR' wherein R' is an alkyl group, as previously defined; and the term dialkylamino refers to a group having the structure —NR'R", wherein R' and R" are each independently selected from the group consisting of alkyl groups. The term trialkylamino refers to a group having the structure —NR'R"R'", wherein R', R", and W are each independently selected from the group consisting of alkyl groups. In certain embodiments, the alkyl group contain 1-20 aliphatic carbon atoms. In certain other embodiments, the alkyl group contains 1-10 aliphatic carbon atoms. In yet other embodiments, the alkyl group contains 1-8 aliphatic carbon atoms. In still other embodiments, the alkyl group contain 1-6 aliphatic carbon atoms. In yet other embodiments, the alkyl group contain 1-4 aliphatic carbon atoms. Additionally, R', R", and/or W taken together may optionally be —$(CH_2)_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of thioalkoxyl moieties include, but are not limited to, methylthio, ethylthio, propylthio, isopropylthio, n-butylthio, and the like.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms aryl and heteroaryl, as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, aryl refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term heteroaryl, as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term carboxylic acid as used herein refers to a group of formula —CO$_2$H.

The terms halo and halogen as used herein refer to an atom selected from fluorine, chlorine, bromine, and iodine.

The term haloalkyl denotes an alkyl group, as defined above, having one, two, or three halogen atoms attached thereto and is exemplified by such groups as chloromethyl, bromoethyl, trifluoromethyl, and the like.

The term heteroaliphatic, as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term heterocyclic, as used herein, refers to an aromatic or non-aromatic, partially unsaturated or fully saturated, 3- to 10-membered ring system, which includes single rings of 3 to 8 atoms in size and bi- and tri-cyclic ring systems which may include aromatic five- or six-membered aryl or aromatic heterocyclic groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring.

The term aromatic heterocyclic, as used herein, refers to a cyclic aromatic radical having from five to ten ring atoms of which one ring atom is selected from sulfur, oxygen, and nitrogen; zero, one, or two ring atoms are additional heteroatoms independently selected from sulfur, oxygen, and nitrogen; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. Aromatic heterocyclic groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide.

Specific heterocyclic and aromatic heterocyclic groups that may be included in the compounds of the invention include: 3-methyl-4-(3-methylphenyl)piperazine, 3 methylpiperidine, 4-(bis-(4-fluorophenyl)methyl)piperazine, 4-(diphenylmethyl)piperazine, 4-(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl)amino)ethyl)piperazine, 4-(2-(diethylamino)ethyl)piperazine, 4-(2-chlorophenyl)piperazine, 4-(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl)piperazine, 4-(2-nitrophenyl)piperazine, 4-(2-nitrophenyl)piperazine, 4-(2- phenylethyl)piperazine, 4-(2-pyridyl)piperazine, 4-(2-pyrimidinyl)piperazine, 4-(2,3-dimethylphenyl)piperazine, 4-(2,4-difluorophenyl)piperazine, 4-(2,4-dimethoxyphenyl)piperazine, 4-(2,4-dimethylphenyl)piperazine, 4-(2,5-dimethylphenyl)piperazine, 4-(2,6-dimethylphenyl)piperazine, 4-(3-chlorophenyl)piperazine, 4-(3-methylphenyl)piperazine, 4-(3-trifluoromethylphenyl)piperazine, 4-(3,4-dichlorophenyl)piperazine, 4-3,4-dimethoxyphenyl)piperazine, 4-(3,4-dimethylphenyl)piperazine, 4-(3,4-methylenedioxyphenyl)piperazine, 4-(3,4,5-trimethoxyphenyl)piperazine, 4-(3,5-dichlorophenyl)piperazine, 4-(3,5-dimethoxyphenyl)piperazine, 4-(4-(phenylmethoxy)phenyl)piperazine, 4-(4-(3,1-dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl)piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl)piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine, 6-fluoro-1,2,3,4-tetrahydro-2-methylquinoline, 1,4-diazacycloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole.

The term carbamoyl, as used herein, refers to an amide group of the formula —CONH$_2$.

The term carbonyldioxyl, as used herein, refers to a carbonate group of the formula —O—CO—OR.

The term hydrocarbon, as used herein, refers to any chemical group comprising hydrogen and carbon. The hydrocarbon may be substituted or unsubstituted. The hydrocarbon may be unsaturated, saturated, branched, unbranched, cyclic, polycyclic, or heterocyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents may also be further substituted (e.g., an aryl group substituent may have another substituent off it, such as another aryl group, which is further substituted with fluorine at one or more positions).

The term thiohydroxyl or thiol, as used herein, refers to a group of the formula —SH.

The following are more general terms used throughout the present application:

As used herein, the singular forms "a", "an", and "the" include the plural reference unless the context clearly indicates otherwise. Thus, for example, a reference to "a monomer" includes a plurality of such monomers.

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). An animal may be a domesticated animal. In certain embodiments, the animal is human. An animal may be a transgenic animal.

"Biocompatible": The term "biocompatible", as used herein is intended to describe compounds that are not toxic to cells. Compounds are "biocompatible" if their addition to cells in vitro results in less than or equal to 20% cell death. The administration in vivo does not cause inflammation, cancer, birth defects, neurotoxicity, or other such adverse side effects.

"Biodegradable": As used herein, "biodegradable" compounds are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably does not cause inflammation, cancer, birth defects, neurotoxicity, or other such adverse side effects in vivo. In certain preferred embodiments, the chemical reactions relied upon to break down the biodegradable compounds are uncatalyzed. For example, the inventive materials may be broken down in part by the hydrolysis of the ester bonds found in cross-linked material.

"Keratin": The term "keratin" as used herein refers any one of a class of fibrous structural proteins found in hair, wool, and nails. Keratin proteins contains a large quantity of cysteine residues. Human hair is approximately 15% cysteine residues cross-linked by disulfide bridges. The helical keratin molecules twist around each other to form elongated strands call intermediate filaments.

"Monomer": As used herein, a "monomer" is a chemical compound that is capable of being linked to other monomers covalently to form a polymer. Examples of monomers include acrylates, methacrylates, epoxide containing compounds, styrenes, and vinyl alcohol. In certain embodiments, the monomers useful in accordance with the present invention are susceptible to free radical polymerization.

Oligomer": The term "oligomer," as used herein, refers to a chemical compound with a finite number of structural units connected by covalent bonds. An oligomer has less monomeric units than the corresponding polymer. An oligomer has at least 3 and typically up to 100 monomeric units making up its structure.

"Peptide" or "protein": As used herein, a "peptide" or "protein" comprises a string of at least three amino acids linked together by peptide bonds. The terms "protein" and "peptide" may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polymer": The term "polymer," as used herein, refers to a chemical compound of repeating structural units (monomers) connected by covalent bonds. A polymer is typically of high molecular weight and may comprise 10 s to 100 s to 1000 s or even more monomers.

Active Hair Care Ingredients

A variety of active hair care ingredients may be used in the inventive cosmetic hair care compositions. A variety of chemical compounds may be used in accordance with the present invention to treat hair. In certain embodiments, the compounds are small molecules. In certain particular embodiments, the compounds are small organic molecules. In certain particular embodiments, the compounds are fluorinated, small organic molecules. In certain particular embodiments, the compounds are non-fluorinated, small organic molecules. In certain particular embodiments, the compounds are chlorinated, small organic molecules. Combinations of compounds may be used to treat hair, thereby creating different cosmetic effects. The availability of a wide range of compounds also allows for treating hair to achieve various desired properties, including: (1) controlling moisture penetration into the hair (frizz control), (2) providing a soft feel to the hair, without a harsh feeling (conditioning), (3) increasing the shine of the hair, (4) enhancing the hair's color, (5) avoiding the feeling of stickiness to the hair (and consequently resisting accumulation of dirt to the hair), (6) dries and sets quickly, (7) can help generate and or preserve the style of the hair, (8) adding strength to the hair, (9) leaving a low amount of residue (are "weightless"), (10) do not flake off the hair, (11) lasting over the course of more than one day, even more than 5 days, (12) affecting, including reducing, the surface energy of the hair (and thereby affording quicker drying of hair), (13) affording manageability for hard-to-treat hair, as well as repairing damaged hair, (14) providing hold, and (15) providing shape.

Some of the above-identified beneficial attributes have been afforded in existing hair care products through use of compositions containing conditioning agents such as silicones or other polymers, which have a high affinity for keratin and especially for the hair on the scalp. Such compounds include, but are not limited to silicones such as cyclomethicone, dimethiconol, dimethicone, cyclopentasiloxane, cyclomethicone, trimethylsiloxyphenyl, dimethiconol, cyclopentasiloxane dimethicone copolyol. However, the coating on keratin fibers, such as the hair, obtained with such compositions often has an unpleasant tacky feel and also may be readily lost via transfer, for example when a hand is passed through the hair. In addition, as a result of such transfer the hair may give the impression of being dirty, sticky or tacky. Also, the effects of the use of such silicone compounds and polymers is not long lasting as they are removed by shampooing the hair, thus making it necessary to repeat application of the compositions to the hair, for example, after rinsing, washing or shampooing. Moreover, residue from silicone compounds may build up on the hair and contribute to making the hair limp, contribute to worsening frizz and when used with heat appliances silicone containing compositions may cause "silicone burn."

The inventive compositions and methods therefore afford the benefits of silicone containing composition without many of their drawbacks. Accordingly, the compositions, methods of the invention preferably do not employ a compound containing a silicone compound; preferably the compositions, methods employ less than 10% wt/vol of such a silicone compound, preferably less than 1% wt/vol of such a silicone compound, more preferably below 0.5% wt/vol, more preferably below 0.2% wt/vol; more preferably below 0.1% wt/vol; more preferably below 0.05% wt/vol; more preferably below 0.01% wt/vol; and still more preferably below 0.001% wt/vol.

Attempts have been made to treat hair with certain acrylate monomers and polymerize them in situ by free-radical polymerization. For example, U.S. Pat. No. 3,676,550 discloses use of certain acrylate and methacrylate compositions as hair treatments. The acrylate and methacrylate monomers employed in U.S. Pat. No. 3,676,550 do not readily polymerize in the presence of moisture. Indeed, those compositions employ an "inert solvent" (which contain 10 to 90% water; the remainder being water-miscible organic solvent).

Unfortunately, compositions and methods that employ in situ free radical polymerization tend to degrade the hair, probably since harsh chemicals are involved. Another problem reported for such compositions and methods is that the chemicals employed irritate and/or are harmful to the hair and/or skin and leave the hair feeling harsh, as well as causing hair discoloration. Furthermore, many such hair treatments may involve reduction of hair prior to treatment, which causes additional hair damage.

In contrast, the compounds employed in the inventive compositions and methods are not toxic, are not harmful to the hair or skin and do not leave the hair feeling harsh or cause hair discoloration. Moreover, the inventive compositions and methods do not rely on free-radical polymerization agents or pre- or post-treatment of the hair with either a reducing or oxidizing agent. In certain embodiments, the inventive compositions and methods do not employ a free radical initiator, a polymerization initiator or a polymerization catalyst. In certain embodiments, the inventive compositions and methods do not employ more than about 0.001% weight/weight, more preferably not more than about 0.01% weight/weight, even more preferably not more than about 0.1% weight/weight of a free radical initiator, a polymerization initiator or a polymerization catalyst. In certain embodiments, there is not more than approximately 0.001 per mol of a free radical initiator, a polymerization initiator or a polymerization catalyst per mol of monomer. Accordingly, the inventive compositions and methods preferably do not employ more than about 0.001% weight/weight, more preferably not more than about 0.01% weight/weight, even more preferably not more than about 0.1% weight/weight of a peroxide; a peracid, a peroxide generating system; a peroxomonosulfate; a peroxodisulfate; a diazo compound, a redox catalyst (such as $NH_4S_2O_8/NaHSO_3$; $H_2O/Fe^{3+}$; $S_2O_8^{-2}/RSH$; $Fe^{3+}/HSO_3$; $Ce^{+4}/ROH$; $KMnO_4$/citric acid; sodium sulfite).

One approach to avoid the harsh chemicals and/or conditions involved in in situ polymerization has been to avoid monomers that do not require such initiators, but rather employ monomers that readily polymerize in the presence of moisture (water). Accordingly, U.S. Pat. No. 5,082,010 shows that cyanoacrylates have been used as a treatment for hair. Cyanoacrylate monomers readily polymerize in the presence of moisture and are said to be "instant adhesives." "Crazy Glue" (2-cyano acrylate) is such an example. In addition, a medical glue, 2-octyl cyanoacrylate, is FDA approved for use as a wound adhesive for use in surgery. Contact with the moisture in the air, or from a biological fluid or tissue, is sufficient for polymerization of such cyanoacrylates.

In contrast, compositions of the present invention employ monomers that do not readily polymerize simply by exposing the monomer to moisture, such as by contact of the monomer with moisture from a biological fluid or tissue as for cyanoacrylates. Indeed, the monomers of the present invention may be formulated as stable compositions using aqueous carriers, for example containing greater than 90% water as carrier. The monomers of the present inventions are not cyanoacrylates.

Use of the inventive compositions are simple and easy. Preferably, the inventive composition is applied to hair that has been just washed. It is not necessary to completely dry the hair, but rather, the hair may be towel dried, allowing for the hair to remain moist, or even dripping wet. A composition of the invention is applied and worked into the hair for example, by the use of a comb or brush, after which the hair is blow dried, preferably using heat from a conventional hair drier, even more preferably, using a heat source below 160° C. and even more preferably, using a heat source below 120° C. In the case of a composition that is a cream, it is recommended that the cream be worked into the ends of the hair, after which the composition is worked into the remaining length of the hair. It is not necessary, and indeed it is preferable, that there be no rinsing step after application of the inventive composition to the hair.

The compounds useful in accordance with the invention are typically low molecular weight organic compounds. In certain embodiments, the chemical compounds are not oligomeric or polymeric. That is, the compound is not an oligomer or low molecular weight polymer. In certain embodiments, the compounds are not peptides or proteins. In certain embodiments, the compounds are not oligonucleotides. In certain embodiments, the compounds are not biomolecules (i.e., compounds found in nature). In certain embodiments, the compounds are dimers. In certain other embodiments, the compounds are trimers.

The molecular weight of the compound used to treat hair is typically sufficient to prevent substantial evaporation of the compound from the treated hair. In certain embodiments, the molecular weight of the compound is less than about 3,000 g/mol. In certain embodiments, the molecular weight of the compound is less than about 2,500 g/mol. In certain embodiments, the molecular weight of the compound is less than about 2,000 g/mol. In certain other embodiments, the molecular weight of the compound is less than about 1,500 g/mol. In certain other embodiments, the molecular weight of the compound is less than about 1,000 g/mol. In certain embodiments, the molecular weight of the compound is less than about 500 g/mol. In certain embodiments, the molecular weight of the compound is less than about 400 g/mol. In certain embodiments, the molecular weight of the compound ranges from about 50 g/mol to about 500 g/mol. In certain embodiments, the molecular weight of the compound ranges from about 100 g/mol to about 500 g/mol. In certain embodiments, the molecular weight of the compound ranges from about 100 g/mol to about 1,000 g/mol. In certain embodiments, the molecular weight of the compound ranges from about 200 g/mol to about 1,000 g/mol. In certain embodiments, the molecular weight of the compound ranges from about 500 g/mol to about 1,000 g/mol. In certain embodiments, the molecular weight of the compound ranges from about 1,000 g/mol to about 2,000 g/mol. In certain embodiments, the molecular weight of the compound is preferably above about 200 g/mol, more preferably above about 300 g/mol, more preferably above about 400 g/mol, and even more preferably above about 500 g/mol.

The compound typically has a boiling point greater than 50° C. In certain embodiments, the boiling point of the compound is greater than 55° C. In certain embodiments, the boiling point of the compound is greater than 60° C. In certain embodiments, the boiling point of the compound is greater than 65° C. In certain embodiments, the boiling point of the compound is greater than 70° C. In certain embodiments, the boiling point of the compound is greater than 75° C. In certain embodiments, the boiling point of the compound is greater than 80° C. In certain embodiments, the boiling point of the compound is greater than 85° C. In certain embodiments, the boiling point of the compound is greater than 90° C. In certain embodiments, the boiling point of the compound is greater than 95° C. In certain embodiments, the boiling point of the compound is greater than 100° C. In certain embodiments, the boiling point of the compound is greater than 110° C. In certain embodiments, the boiling point of the compound is greater than 120° C. In certain embodiments, the boiling point of the compound is greater than 130° C. In certain embodiments, the boiling point of the compound is greater than 140° C. In certain embodiments, the boiling point of the compound is greater than 150° C. In certain embodiments, the boiling point of the compound is greater than 175° C. In certain embodiments, the boiling point of the compound is greater than 200° C.

The compound typically has a melting point less than 40° C. In certain embodiments, the melting point of the compound is less than 35° C. In certain embodiments, the melting point of the compound is less than 30° C. In certain embodiments, the melting point of the compound is less than 35° C. In certain embodiments, the melting point of the compound is less than 30° C. In certain embodiments, the melting point of the compound is less than 25° C. In certain embodiments, the melting point of the compound is less than 20° C. In certain embodiments, the melting point of the compound is less than 15° C. In certain embodiments, the melting point of the compound is less than 10° C. In certain embodiments, the melting point of the compound is less than 0° C.

In certain embodiments, the compound has a melting point less than about 10° C. and a boiling point greater than about 60° C. In certain embodiments, the compound has a melting point less than about 20° C. and a boiling point greater than about 70° C. In certain embodiments, the compound has a melting point less than about 20° C. and a boiling point greater than about 80° C. In certain embodiments, the compound has a melting point less than about 10° C. and a boiling point greater than about 100° C. In certain embodiments, the compound has a melting point less than about 20° C. and a boiling point greater than about 100° C.

The compound typically comprises an unsaturated functional group such as a double or triple bond. Example of unsaturated functional groups include alkenes, alkynes, carbonyls, and imines. In certain embodiments, the compound includes a conjugated unsaturated system. In certain embodiments, the compound includes an $\alpha,\beta$-unsaturated carbonyl moiety. In certain embodiments, the compound includes an acrylate moiety. In certain embodiments, the compound includes a crotonate moiety. In certain embodiments, the compound includes a methacrylate moiety. In certain embodiments, the compound includes a 2-fluoroacrylate moiety. In certain embodiments, the compound includes a diacrylate moiety. In certain embodiments, the compound includes a dicrotonate moiety. In certain embodiments, the compound includes a dimethacrylate moiety. In certain embodiments, the compound includes an alkene. In certain embodiments, the compound includes a vinyl group. In certain embodiments, the compound include an allyl group. In certain embodiments, the compound includes a diene. In certain embodiments, the compounds comprise a conjugated diene moiety. In certain embodiments, the compound includes an alkyne. In certain embodiments, the compound includes an eneyne moiety. In certain embodiments, the compound includes an aryl moiety. In certain embodiments, the compound includes a phenyl moiety. In certain embodiments, the compound includes a styrene moiety. In certain embodiments, the compound includes multiple fused phenyl moieties. In certain embodiments, the compound includes a heteroaryl moiety.

Particularly useful compounds in the inventive hair care system include alkene-containing compounds. In certain particular embodiments, the alkene is monosubstituted. In other embodiments, the alkene is disubstituted. Disubstituted alkenes may be either in the cis or trans configuration, or any mixture thereof. In yet other embodiments, the alkene is trisubstituted. The trisubstituted alkene may be in either the E or Z configuration, or any mixture thereof. In still other embodiments, the alkene is tetrasubstituted. Again, various isomers are possible and are considered part of this invention.

In certain embodiments, the monosubstituted alkene-containing compound useful for hair treatment is of the formula:

wherein $R_1'$ is selected from the group consisting of cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR_A$; —$C(O)R_A$; —$CO_2R_A$; —$C(O)N(R_A)_2$; —$SR_A$; —$SOR_A$; —$SO_2R_A$; —$NR_A$; —$N(R_A)_2$; —$NHC(O)R_A$; and —$C(R_A)_3$; wherein each occurrence of $R_A$ is independently selected from a group consisting of hydrogen, cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; alkoxy; aryloxy; alkylthio; arylthio; amino; alkylamino; dialkylamino; heteroaryloxy; heteroarylthio and a protecting group.

In certain embodiments, $R_1'$ is a substituted or unsubstituted, branched or unbranched aliphatic moiety. In certain embodiments, $R_1'$ is an alkyl moiety. In certain embodiments, $R_1'$ is of one of the formulae:

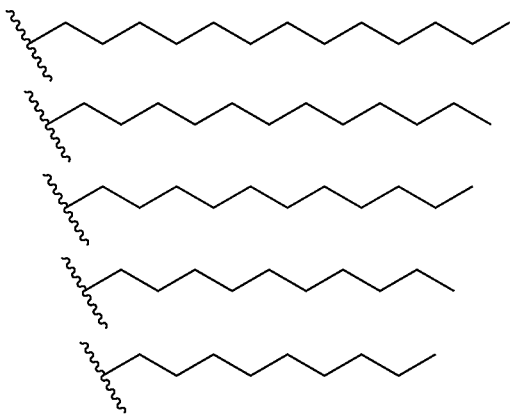

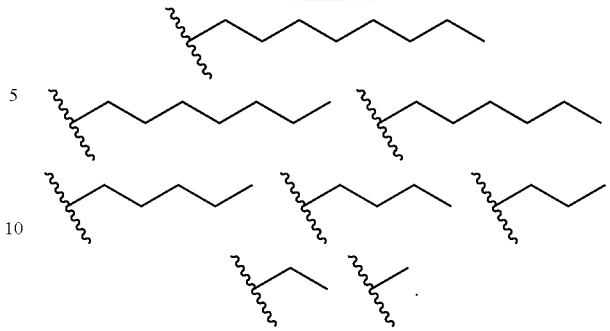

As would be appreciated by one of skill in this art, any of the above alkyl groups may be substituted, branched, unsaturated, and/or cyclic.

In certain embodiments, $R_1'$ is one of the formulae:

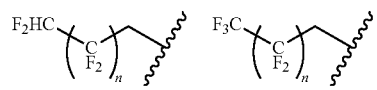

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive. In certain embodiments, n is an integer between 3 and 20, inclusive.

In certain embodiments, $R_1'$ is one of the formulae:

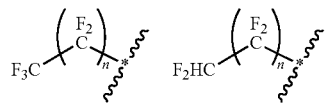

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive. In certain embodiments, n is an integer between 3 and 20, inclusive.

In certain embodiments, $R_1'$ is of the formula:

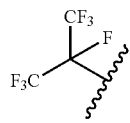

In certain embodiments, $R_1'$ is of the formula:

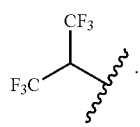

In yet other embodiments, $R_1'$ is a substituted or unsubstituted, branched or unbranched heteroaliphatic moiety. In still other embodiments, $R_1'$ is a substituted or unsubstituted acyl moiety.

In other embodiments, $R_1'$ is a substituted or unsubstituted aryl moiety. In certain particular embodiments, $R_1'$ is of the formula:

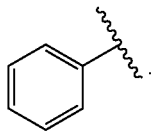 [SMILES: *c1ccccc1]

In certain particular embodiments, $R_1'$ is of the formula:

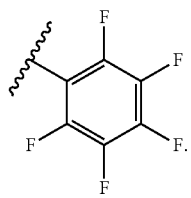 [SMILES: *c1c(F)c(F)c(F)c(F)c1F]

In certain particular embodiments, $R_1'$ is of the formula:

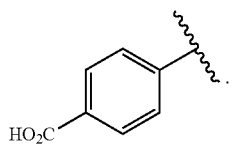

In certain particular embodiments, $R_1'$ is a substituted or unsubstituted phenyl moiety. In certain embodiments, $R_1'$ is substituted phenyl (e.g., a phenyl ring with 1, 2, 3, 4, or 5 substituents). In other embodiments, $R_1'$ is a substituted or unsubstituted heteroaryl moiety.

In certain embodiments, $R_1'$ is —C(O)$R_A$. In other embodiments, $R_1'$ is —CO$_2R_A$. In certain embodiments, $R_A$ is $C_1$-$C_6$ alkyl. In certain particular

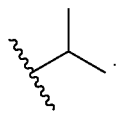

embodiments, $R_A$ is methyl. In certain embodiments, $R_A$ is In other embodiments, $R_A$ is t-butyl.

In certain particular embodiments, $R_1'$ is —CO$_2R_A$, wherein $R_A$ is one of the formulae:

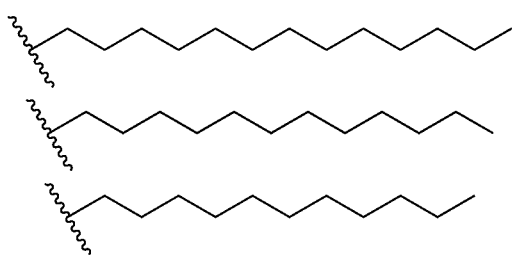

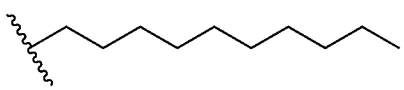

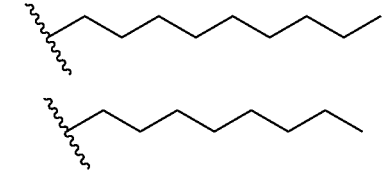

As would be appreciated by one of skill in this art, any of the above alkyl groups may be substituted, branched, unsaturated, and/or cyclic.

In certain particular embodiments, $R_1'$ is —CO$_2R_A$, wherein $R_A$ is selected from the group consisting of:

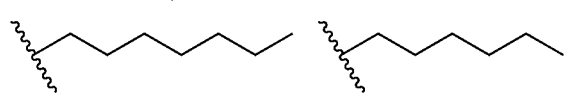

wherein n is an integer between 0 and 20, inclusive; and m is an even or odd integer between 1 and 6, inclusive.

In certain particular embodiments, $R_1'$ is —CO$_2R_A$, wherein $R_A$ is one of the formulae:

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive.

In certain particular embodiments, $R_1'$ is —CO$_2R_A$, wherein $R_A$ is of the formulae:

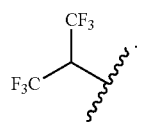

In certain particular embodiments, $R_1'$ is —$CO_2R_A$, wherein $R_A$ is of the formulae:

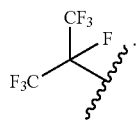

In certain particular embodiments, $R_1'$ is —$CO_2R_A$, wherein $R_A$ is aryl or arylalkyl. In certain particular embodiments, $R_1'$ is —$CO_2R_A$, wherein $R_A$ is of the formula:

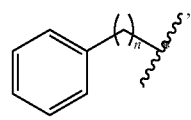

wherein n is an integer between 0 and 12, inclusive. In certain embodiments, n is 0. In certain embodiments, n is 1. In other embodiments, n is 2, 3, 4, 5, or 6. In certain particular embodiments, $R_1'$ is —$CO_2R_A$, wherein $R_A$ is of the formula:

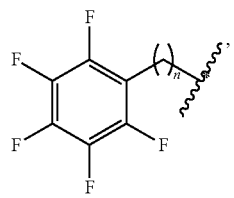

wherein n is an integer between 0 and 12, inclusive. In certain particular embodiments, $R_1'$ is —$CO_2R_A$, wherein $R_A$ is of the formula:

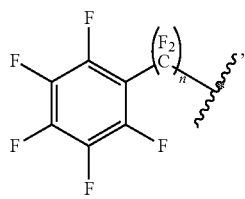

wherein n is an integer between 0 and 12, inclusive. In certain embodiments, n is 0. In certain embodiments, n is 1. In other embodiments, n is 2, 3, 4, 5, or 6. In certain particular embodiments, $R_1'$ is —$CO_2R_A$, wherein $R_A$ is of the formula:

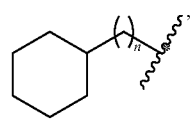

wherein n is an integer between 0 and 12, inclusive. In certain particular embodiments, $R_1'$ is —$CO_2R_A$, wherein $R_A$ is of the formula:

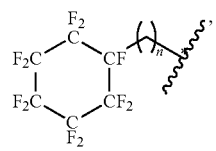

wherein n is an integer between 0 and 12, inclusive. In certain particular embodiments, $R_1'$ is —$CO_2R_A$, wherein $R_A$ is of the formula:

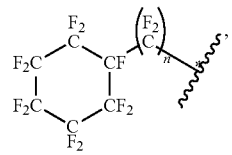

wherein n is an integer between 0 and 12, inclusive. In certain embodiments, n is 0. In certain embodiments, n is 1. In other embodiments, n is 2, 3, 4, 5, or 6.

In certain embodiments, the compound is an acrylate of formula:

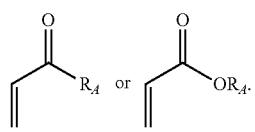

Exemplary acrylate compounds include:

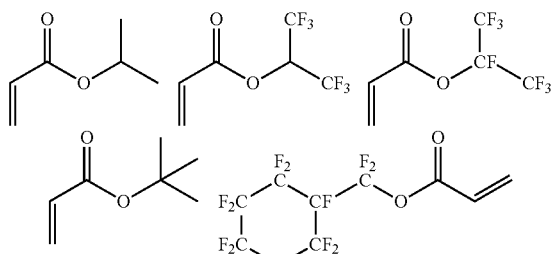

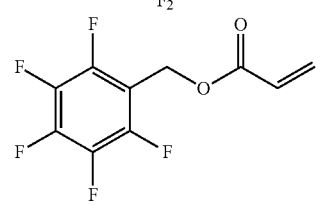

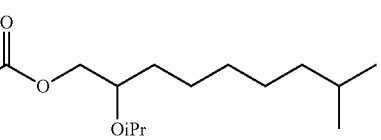

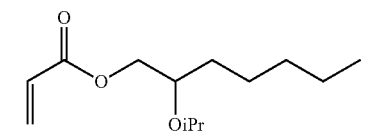

-continued

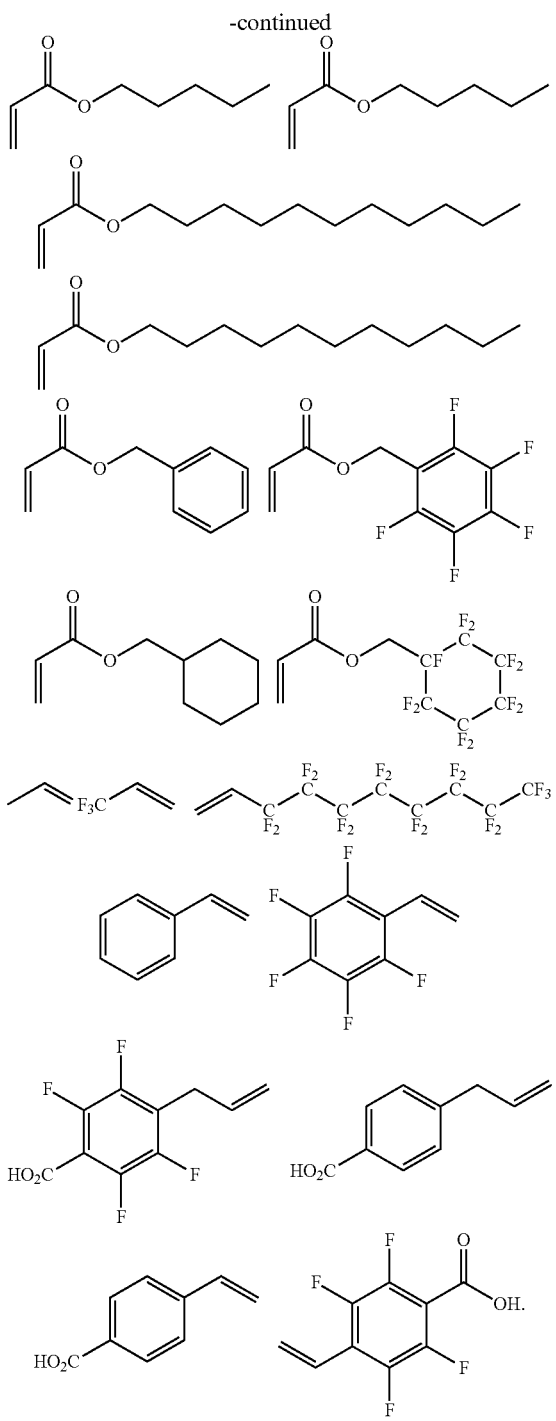

In certain embodiments, the alkene-containing compound useful in the treatment of hair is of the formula:

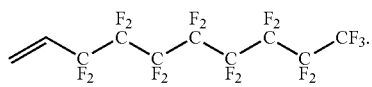

In certain embodiments, the disubstituted alkene-containing compound useful in the treatment of hair is of one of the formulae:

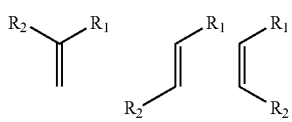

wherein

R$_1$ and R$_2$ are each independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$_A$; —C(O)R$_A$; —CO$_2$R$_A$; —C(O)N(R$_A$)$_2$; —SR$_A$; —SOR$_A$; —SO$_2$R$_A$; —NR$_A$; —N(R$_A$)$_2$; —NHC(O)R$_A$; and —C(R$_A$)$_3$;

wherein each occurrence of R$_A$ is independently selected from a group consisting of hydrogen, cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; alkoxy; aryloxy; alkylthio; arylthio; amino; alkylamino; dialkylamino; heteroaryloxy; heteroarylthio and a protecting group;

or R$_1$ and R$_2$ form a cyclic structure; and provided that when R$_1$ is hydrogen, R$_2$ is not hydrogen.

In other embodiments, R$_1$ is a substituted or unsubstituted, branched or unbranched aliphatic moiety. In certain embodiments, R$_1$ is an alkyl moiety. In certain embodiments, R$_1$ is C$_1$-C$_6$ alkyl moiety. In certain embodiments, R$_1$ is of one of the formulae:

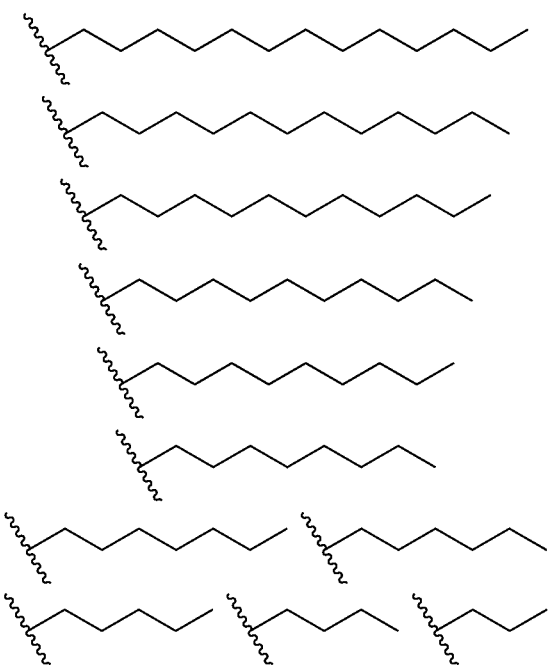

-continued

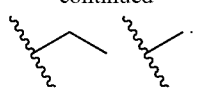

As would be appreciated by one of skill in this art, any of the above alkyl groups may be substituted, branched, unsaturated, and/or cyclic.

In certain particular embodiments, $R_1$ is one of the formulae:

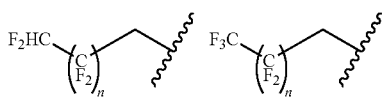

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive. In certain embodiments, n is an integer between 3 and 20, inclusive.

In certain embodiments, $R_1$ is one of the formulae:

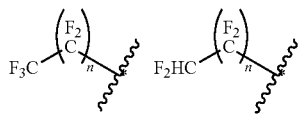

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive. In certain embodiments, n is an integer between 3 and 20, inclusive.

In certain particular embodiments, $R_1$ is of the formula:

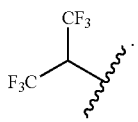

In certain particular embodiments, $R_1$ is of the formula:

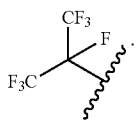

In yet other embodiments, $R_1$ is a substituted or unsubstituted, branched or unbranched heteroaliphatic moiety. In still other embodiments, $R_1$ is a substituted or unsubstituted acyl moiety.

In other embodiments, $R_1$ is a substituted or unsubstituted aryl moiety. In certain particular embodiments, $R_1$ is of the formula:

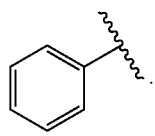

In certain particular embodiments, $R_1$ is of the formula:

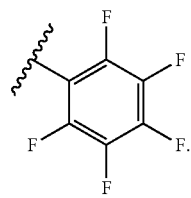 [SMILES: *c1c(F)c(F)c(F)c(F)c1F]

In certain particular embodiments, $R_1$ is of the formula:

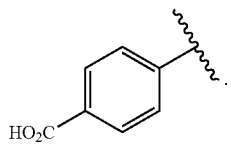

In certain particular embodiments, $R_1$ is a substituted or unsubstituted phenyl moiety. In certain embodiments, $R_1$ is substituted phenyl moiety (e.g., a phenyl ring with 1, 2, 3, 4, or 5 substituents). In other embodiments, $R_1$ is a substituted or unsubstituted heteroaryl moiety.

In certain embodiments, $R_1$ is —C(O)$R_4$. In other embodiments, $R_1$ is —CO$_2$$R_4$. In certain embodiments, $R_4$ is $C_1$-$C_6$ alkyl. In certain particular embodiments, $R_4$ is methyl. In certain embodiments, $R_4$ is

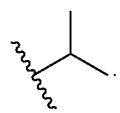

In other embodiments, $R_4$ is t-butyl. In certain particular embodiments, $R_1$ is —CO$_2$$R_4$, wherein $R_4$ is one of the formulae:

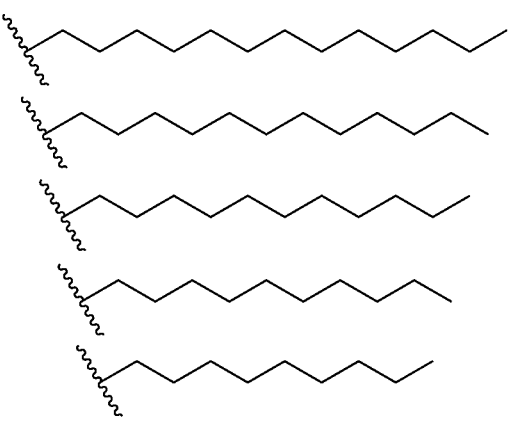

-continued

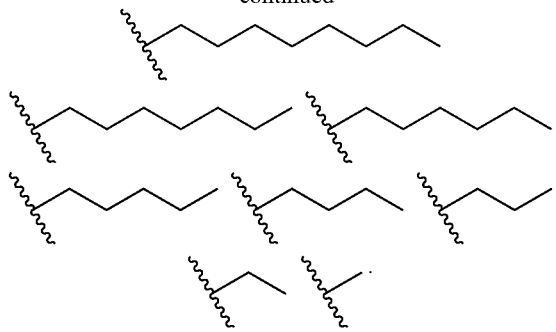

As would be appreciated by one of skill in this art, any of the above alkyl groups may be substituted, branched, unsaturated, and/or cyclic.

In certain particular embodiments, $R_1$ is $—CO_2R_A$, wherein $R_A$ is selected from the group consisting of:

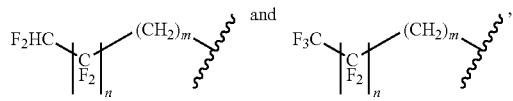

wherein n is an integer between 0 and 20, inclusive; and m is an even or odd integer between 1 and 6, inclusive.

In certain particular embodiments, $R_1$ is $—CO_2R_A$, wherein $R_A$ is one of

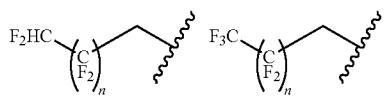

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive.

In certain particular embodiments, $R_1$ is $—CO_2R_A$, wherein $R_A$ is of the formulae:

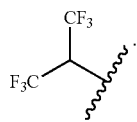

In certain particular embodiments, $R_1$ is $—CO_2R_A$, wherein $R_A$ is of the

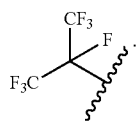

In certain particular embodiments, $R_1$ is $—CO_2R_A$, wherein $R_A$ is aryl or arylalkyl. In certain particular embodiments, $R_1$ is $—CO_2R_A$, wherein $R_A$ is of the formula:

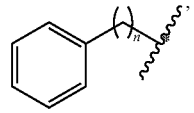

wherein n is an integer between 0 and 12, inclusive. In certain embodiments, n is 0. In certain embodiments, n is 1. In other embodiments, n is 2, 3, 4, 5, or 6. In certain particular embodiments, $R_1$ is $—CO_2R_A$, wherein $R_A$ is of the formula:

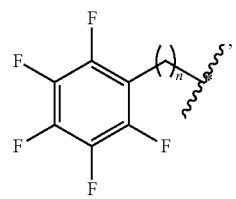

wherein n is an integer between 0 and 12, inclusive. In certain particular embodiments, $R_1$ is $—CO_2R_A$, wherein $R_A$ is of the formula:

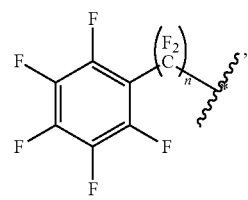

wherein n is an integer between 0 and 12, inclusive. In certain embodiments, n is 0. In certain embodiments, n is 1. In other embodiments, n is 2, 3, 4, 5, or 6. In certain particular embodiments, $R_1$ is $—CO_2R_A$, wherein $R_A$ is of the formula:

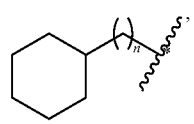

wherein n is an integer between 0 and 12, inclusive. In certain embodiments, n is 0. In certain embodiments, n is 1. In other embodiments, n is 2, 3, 4, 5, or 6. In certain particular embodiments, $R_1$ is $—CO_2R_A$, wherein $R_A$ is of the formula:

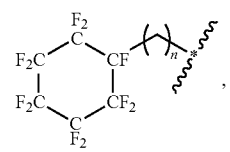

wherein n is an integer between 0 and 12, inclusive. In certain particular embodiments, $R_1$ is $—CO_2R_A$, wherein $R_A$ is of the formula:

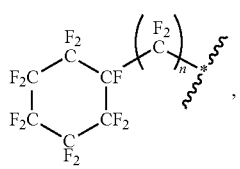

wherein n is an integer between 0 and 12, inclusive. In certain embodiments, n is 0. In certain embodiments, n is 1. In other embodiments, n is 2, 3, 4, 5, or 6.

In certain embodiments, $R_1$ or $R_2$ contains at least one halogen, provided that when $R_1$ is halogen, $R_2$ is not halogen. In certain embodiments, $R_1$ or $R_2$ contains at least one fluorine, provided that when $R_1$ is fluorine, $R_2$ is not fluorine.

In certain embodiments, $R_2$ is substituted or unsubstituted, branched or unbranched aliphatic. In yet other embodiments, $R_2$ is $C_1$-$C_6$ alkyl. In certain embodiments, $R_2$ is an alkyl moiety. In certain particular embodiments, $R_2$ is methyl. In certain particular embodiments, $R_2$ is ethyl. In certain embodiments, $R_2$ is propyl. In certain embodiments, $R_2$ is butyl. In certain embodiments, $R_2$ is trifluoromethyl. In certain embodiments, $R_2$ is a aryl or heteroaryl moiety. In certain embodiments, $R_2$ is a phenyl moiety.

In certain embodiments, $R_2$ is —$CO_2R_A$, wherein $R_A$ is cyclic or acyclic, branched or unbranched aliphatic substituted with one or more halogen.

In certain other embodiments, $R_2$ is —$CO_2R_A$, wherein $R_A$ is selected from the group consisting of:

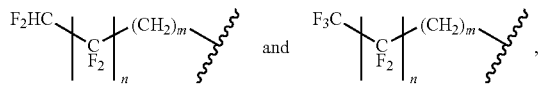

wherein n is an integer between 0 and 20, inclusive; and m is an even or odd integer between 1 and 6, inclusive.

In certain other embodiments, $R_2$ is —$CO_2R_A$, wherein $R_A$ is selected from the group consisting of:

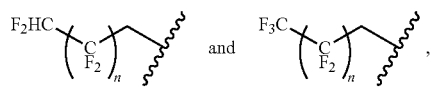

wherein n is an integer between 0 and 20, inclusive.

In certain embodiments, $R_1$ is —$CO_2R_A$. In other embodiments, $R_1$ is —$CO_2R_A$, and $R_2$ is $C_1$-$C_6$ alkyl. In other embodiments, $R_1$ is —$CO_2R_A$, and $R_2$ is methyl. In other embodiments, $R_1$ is —$CO_2R_A$, and $R_2$ is trifluoromethyl. In other embodiments, $R_1$ is —$CO_2R_A$, and $R_2$ is fluorine.

In certain embodiments, $R_1$ is selected from the group consisting of hydrogen, halogen and cyclic or acyclic, branched or unbranched aliphatic or aryl having up to six carbons, wherein said alkyl or aryl may optionally be substituted with one or more functional group selected from the group consisting of halogen, —OH and —$OCH_3$; and $R_2$ is selected from the group consisting of $R_A$, —$C(O)R_A$ and —$CO_2R_A$, wherein $R_A$ is a cyclic or acyclic, substituted or unsubstituted, branched or unbranched aliphatic.

In certain embodiments, $R_1$ is selected from the group consisting of hydrogen, halogen and cyclic or acyclic, branched or unbranched aliphatic or aryl having up to six carbons, wherein said alkyl or aryl may optionally be substituted with one or more functional group selected from the group consisting of halogen, —OH and —$OCH_3$; and $R_2$ is —$CO_2H$.

In certain embodiments, the compound is a methacrylate of formula:

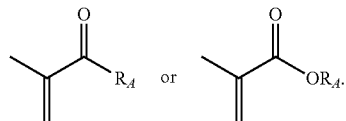

In certain embodiments, the compound is a trifluoromethacrylate of formula:

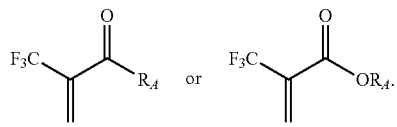

In certain embodiments, the compound is a 2-fluoroacrylate of formula:

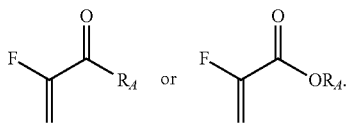

In certain embodiments, the compound is a crotonate of formula:

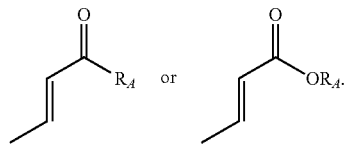

Exemplary disubstituted fluorinated compounds include:

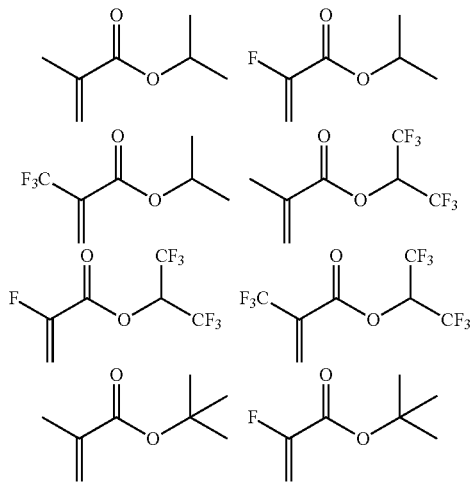

-continued

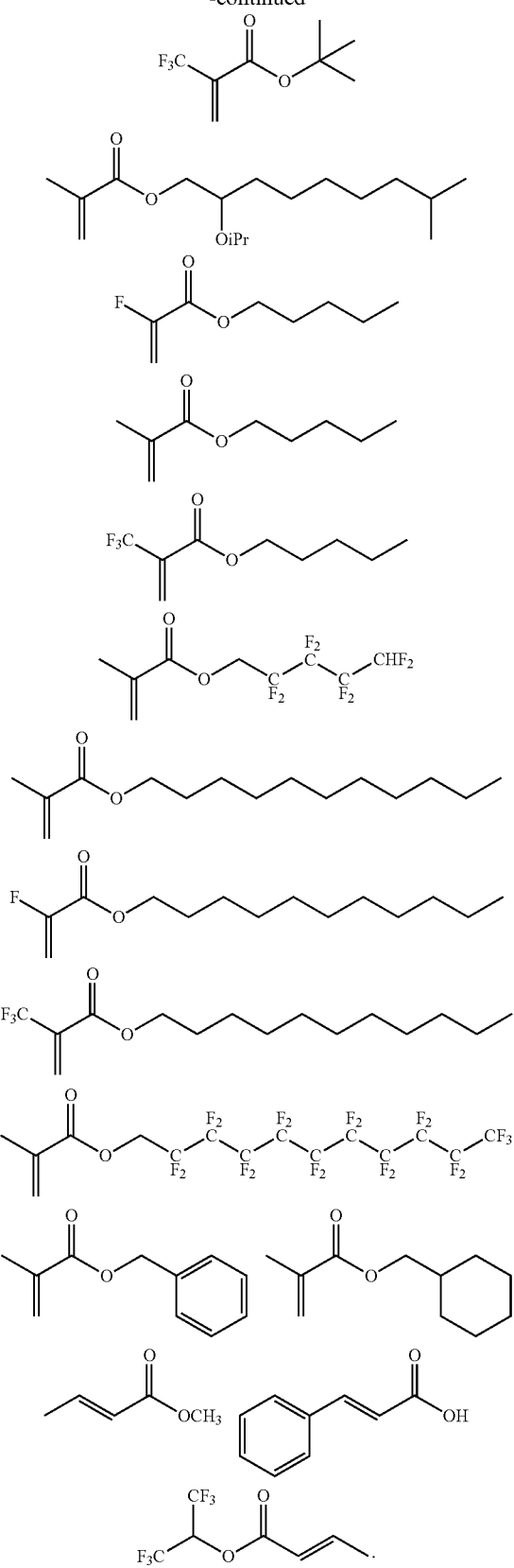

In certain embodiments, the methacrylate useful in the treatment of hair is of the formula:

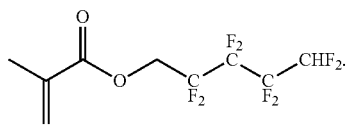

Octafluoropentyl methacrylate (OFPMA)

In certain embodiments, the trisubstituted alkene-containing compound useful in the treatment of hair is of one of the formulae:

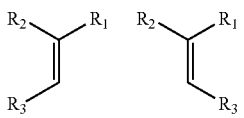

wherein $R_1$, $R_2$ and $R_3$ are each independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR_A$; —$C(O)R_A$; —$CO_2R_A$; —$C(O)N(R_A)_2$; —$SR_A$; —$SOR_A$; —$SO_2R_A$; —$NR_A$; —$N(R_A)_2$; —$NHC(O)R_A$; and —$C(R_A)_3$;

wherein each occurrence of $R_A$ is independently selected from a group consisting of hydrogen, cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; alkoxy; aryloxy; alkylthio; arylthio; amino; alkylamino; dialkylamino; heteroaryloxy; heteroarylthio and a protecting group;

or $R_1$, $R_2$, and/or $R_3$ may form a cyclic structure; and provided that $R_1$, $R_2$ and $R_3$ are not simultaneously hydrogen.

In other embodiments, $R_1$ is a substituted or unsubstituted, branched or unbranched aliphatic moiety. In certain embodiments, $R_1$ is an alkyl moiety. In certain embodiments, $R_1$ is $C_1$-$C_6$ alkyl moiety. In certain embodiments, $R_1$ is of one of the formulae:

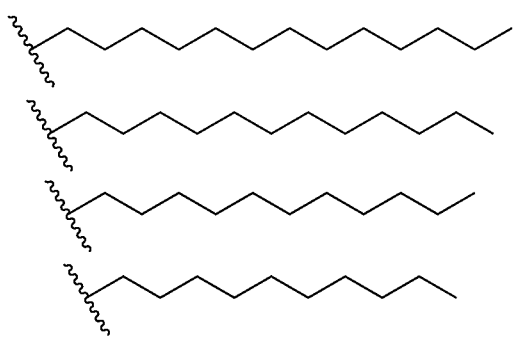

-continued

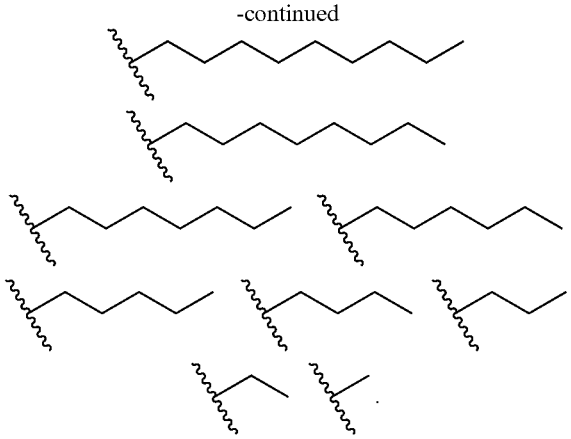

As would be appreciated by one of skill in this art, any of the above alkyl groups may be substituted, branched, unsaturated, and/or cyclic.

In certain embodiments, $R_1$ is one of the formulae:

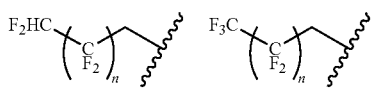

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive. In certain embodiments, n is an integer between 3 and 20, inclusive.

In certain embodiments, $R_1$ is one of the formulae:

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive. In certain embodiments, n is an integer between 3 and 20, inclusive.

In certain embodiments, $R_1$ is of the formula:

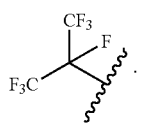

In certain embodiments, $R_1$ is of the formula:

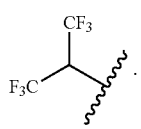

In yet other embodiments, $R_1$ is a substituted or unsubstituted, branched or unbranched heteroaliphatic moiety. In still other embodiments, $R_1$ is a substituted or unsubstituted acyl moiety.

In other embodiments, $R_1$ is a substituted or unsubstituted aryl moiety. In certain particular embodiments, $R_1$ is of the formula:

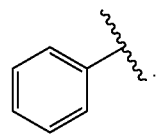 [SMILES: *c1ccccc1]

In certain particular embodiments, $R_1$ is of the formula:

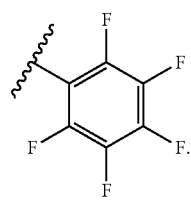 [SMILES: *c1c(F)c(F)c(F)c(F)c1F]

In certain particular embodiments, $R_1$ is of the formula:

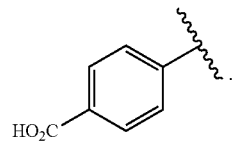

In certain particular embodiments, $R_1$ is a substituted or unsubstituted phenyl moiety. In certain embodiments, $R_1$ is substituted phenyl moiety (e.g., a phenyl ring with 1, 2, 3, 4, or 5 substituents). In other embodiments, $R_1$ is a substituted or unsubstituted heteroaryl moiety.

In certain embodiments, $R_1$ is —C(O)$R_4$. In other embodiments, $R_1$ is —CO$_2R_4$. In certain embodiments, $R_4$ is $C_1$-$C_6$ alkyl. In certain particular embodiments, $R_4$ is methyl. In certain particular embodiments, $R_4$ is trifluoromethyl. In certain embodiments, $R_4$ is

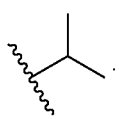

In certain embodiments, $R_4$ is

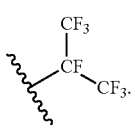

In certain embodiments, $R_A$ is

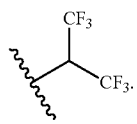 [SMILES: *C(C(F)(F)F)C(F)(F)F]

In other embodiments, $R_A$ is t-butyl. In certain particular embodiments, $R_1$ is $-CO_2R_A$, wherein $R_A$ is one of the formulae:

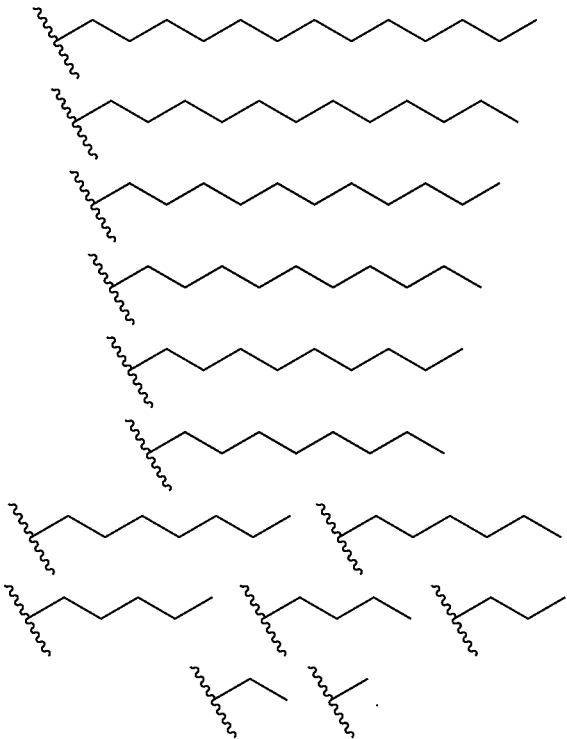

As would be appreciated by one of skill in this art, any of the above alkyl group may be partially substituted, branched, unsaturated, and/or cyclic.

In certain particular embodiments, $R_1$ is $-CO_2R_A$, wherein $R_A$ is selected from the group consisting of:

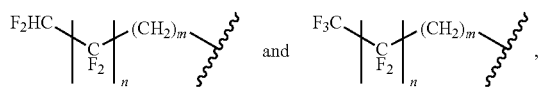

wherein n is an integer between 0 and 20, inclusive; and m is an even or odd integer between 1 and 6, inclusive.

In certain particular embodiments, $R_1$ is $-CO_2R_A$, wherein $R_A$ is one of the formulae:

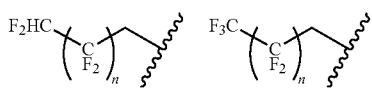

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive.

In certain particular embodiments, $R_1$ is $-CO_2R_A$, wherein $R_A$ is of the

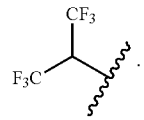

In certain particular embodiments, $R_1$ is $-CO_2R_A$, wherein $R_A$ is of the formulae:

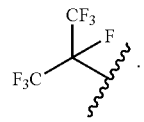

In certain particular embodiments, $R_1$ is $-CO_2R_A$, wherein $R_A$ is aryl or arylalkyl. In certain particular embodiments, $R_1$ is $-CO_2R_A$, wherein $R_A$ is of the formula:

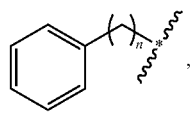

wherein n is an integer between 0 and 12, inclusive. In certain embodiments, n is 0. In certain embodiments, n is 1. In other embodiments, n is 2, 3, 4, 5, or 6. In certain particular embodiments, $R_1$ is $-CO_2R_A$, wherein $R_A$ is of the formula:

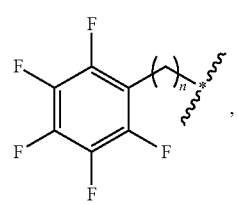

wherein n is an integer between 0 and 12, inclusive. In certain particular embodiments, $R_1$ is $-CO_2R_A$, wherein $R_A$ is of the formula:

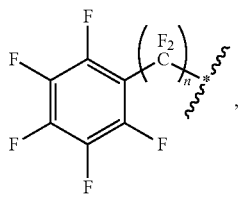

wherein n is an integer between 0 and 12, inclusive. In certain embodiments, n is 0. In certain embodiments, n is 1. In other embodiments, n is 2, 3, 4, 5, or 6. In certain particular embodiments, $R_1$ is $-CO_2R_A$, wherein $R_A$ is of the formula:

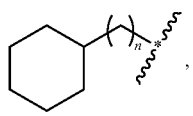

wherein n is an integer between 0 and 12, inclusive. In certain particular embodiments, $R_1$ is —$CO_2R_A$, wherein $R_A$ is of the formula:

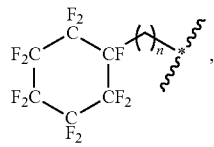

wherein n is an integer between 0 and 12, inclusive. In certain embodiments, n is 0. In certain embodiments, n is 1. In other embodiments, n is 2, 3, 4, 5, or 6.

In certain embodiments, $R_1$, $R_2$, or $R_3$ contains at least one halogen, provided that each is not simultaneously halogen. In certain embodiments, $R_1$, $R_2$, or $R_3$ contains at least one fluorine, but each is not simultaneously fluorine.

In other embodiments, $R_2$ is substituted or unsubstituted, branched or unbranched aliphatic. In yet other embodiments, $R_2$ is $C_1$-$C_6$ alkyl. In certain particular embodiments, $R_2$ is methyl. In certain particular embodiments, $R_2$ is ethyl. In certain embodiments, $R_2$ is propyl. In certain embodiments, $R_2$ is butyl. In certain embodiments, $R_2$ is trifluoromethyl. In certain embodiments, $R_2$ is a aryl or heteroaryl moiety. In certain embodiments, $R_2$ is a phenyl moiety.

In certain embodiments, $R_2$ is of one of the formulae:

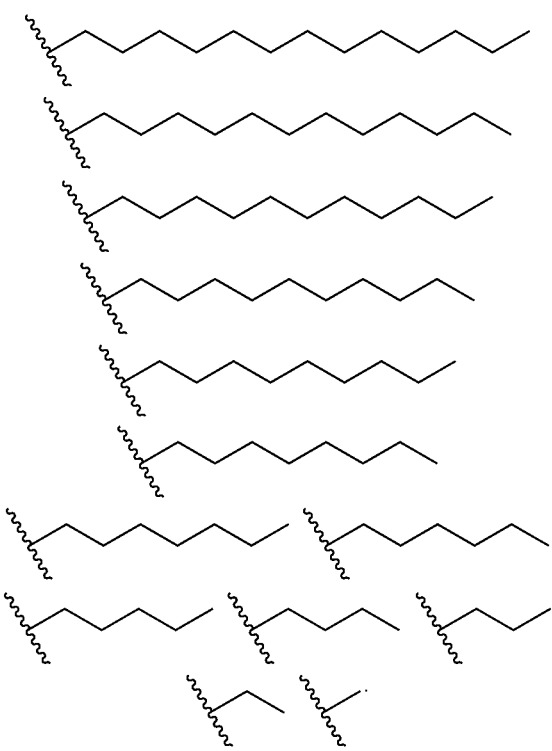

As would be appreciated by one of skill in this art, any of the above alkyl group may be substituted, branched, unsaturated, and/or cyclic. In yet other embodiments, $R_2$ is a substituted or unsubstituted, branched or unbranched heteroaliphatic moiety. In still other embodiments, $R_2$ is a substituted or unsubstituted acyl moiety. In other embodiments, $R_2$ is a substituted or unsubstituted aryl moiety. In certain particular embodiments, $R_2$ is of the formula:

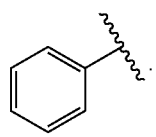

In certain particular embodiments, $R_2$ is of the formula:

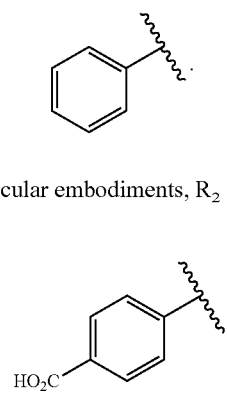

In certain particular embodiments, $R_2$ is a substituted or unsubstituted phenyl moiety. In certain embodiments, $R_2$ is substituted phenyl moiety (e.g., a phenyl ring with 1, 2, 3, 4, or 5 substituents). In other embodiments, $R_2$ is a substituted or unsubstituted heteroaryl moiety. In certain embodiments, $R_2$ is —$C(O)R_B$. In other embodiments, $R_2$ is —$CO_2R_B$. In certain embodiments, $R_B$ is $C_1$-$C_6$ alkyl. In certain particular embodiments, $R_B$ is methyl. In certain embodiments, $R_B$ is

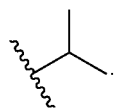

In other embodiments, $R_B$ is t-butyl. In certain particular embodiments, $R_2$ is —$CO_2R_B$, wherein $R_B$ is one of the formulae:

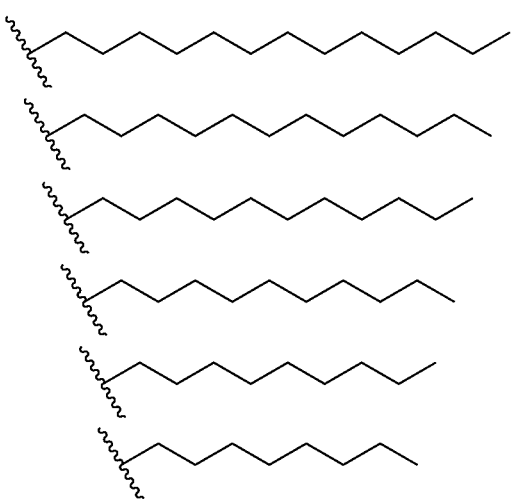

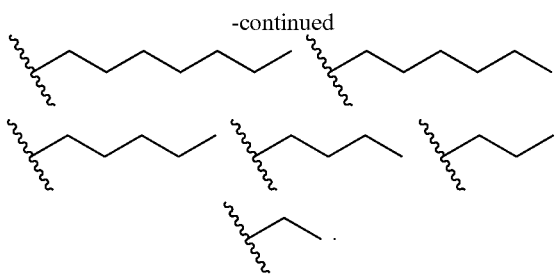

As would be appreciated by one of skill in this art, any of the above alkyl groups may be substituted, branched, unsaturated, and/or cyclic.

In certain particular embodiments, $R_2$ is —$CO_2R_B$, wherein $R_B$ is aryl or arylalkyl. In certain particular embodiments, $R_2$ is —$CO_2R_B$, wherein $R_B$ is of the formula:

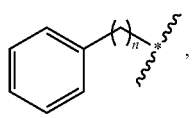

wherein n is an integer between 0 and 12, inclusive. In certain embodiments, n is 0. In certain embodiments, n is 1. In other embodiments, n is 2, 3, 4, 5, or 6. In certain particular embodiments, $R_2$ is —$CO_2R_B$, wherein $R_B$ is of the formula:

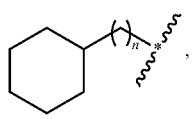

wherein n is an integer between 0 and 12, inclusive. In certain embodiments, n is 0. In certain embodiments, n is 1. In other embodiments, n is 2, 3, 4, 5, or 6.

In certain embodiments, $R_1$ is —$CO_2R_A$. In other embodiments, $R_1$ is —$CO_2R_A$, and $R_2$ is $C_1$-$C_6$ alkyl. In other embodiments, $R_1$ is —$CO_2R_A$, and $R_2$ is methyl. In other embodiments, $R_1$ is —$CO_2R_A$, and $R_2$ is trifluoromethyl. In other embodiments, $R_1$ is —$CO_2R_A$, and $R_2$ is fluorine.

In certain embodiments, $R_3$ is halogen. In certain embodiments, $R_3$ is fluorine.

In other embodiments, $R_3$ is substituted or unsubstituted, branched or unbranched aliphatic. In yet other embodiments, $R_3$ is $C_1$-$C_6$ alkyl. In certain embodiments, $R_3$ is a alkyl moiety. In certain particular embodiments, $R_3$ is methyl. In certain particular embodiments, $R_3$ is ethyl. In certain embodiments, $R_3$ is propyl. In certain embodiments, $R_2$ is butyl. In certain embodiments, $R_3$ is trifluoromethyl. In certain embodiments, $R_3$ is a aryl or heteroaryl moiety. In certain embodiments, $R_3$ is a phenyl moiety. In certain particular embodiments, $R_3$ is a phenyl moiety.

In certain embodiments, $R_3$ is of one of the formulae:

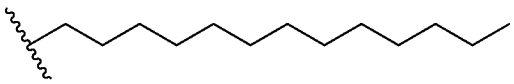

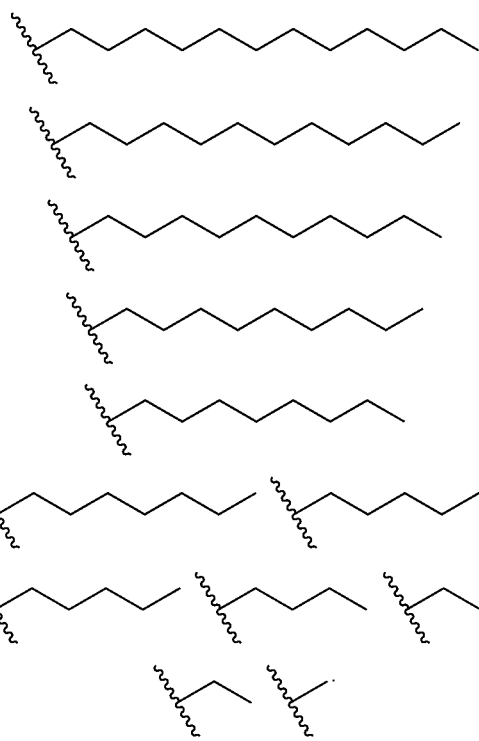

As would be appreciated by one of skill in this art, any of the above alkyl groups may be substituted, branched, unsaturated, and/or cyclic. In yet other embodiments, $R_3$ is a substituted or unsubstituted, branched or unbranched heteroaliphatic moiety. In still other embodiments, $R_3$ is a substituted or unsubstituted acyl moiety. In other embodiments, $R_3$ is a substituted or unsubstituted aryl moiety. In certain particular embodiments, $R_3$ is of the formula:

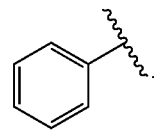 [SMILES: *c1ccccc1]

In certain particular embodiments, $R_3$ is of the formula:

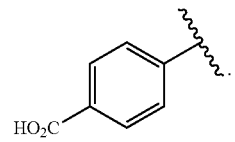

In certain particular embodiments, $R_3$ is a substituted or unsubstituted phenyl moiety. In certain embodiments, $R_3$ is a substituted phenyl moiety (e.g., a phenyl ring with 1, 2, 3, 4, or 5 substituents). In other embodiments, $R_3$ is a substituted or unsubstituted heteroaryl moiety. In certain embodiments, $R_3$ is —$C(=O)R_C$. In other embodiments, $R_3$ is —$CO_2R_C$. In certain embodiments, $R_C$ is $C_1$-$C_6$ alkyl. In certain particular embodiments, $R_C$ is methyl. In certain embodiments, $R_C$ is

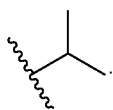 [SMILES: *C(C)C]

In other embodiments, $R_C$ is t-butyl. In certain particular embodiments, $R_3$ is —CO$_2$R$_A$, wherein $R_C$ is one of the formulae:

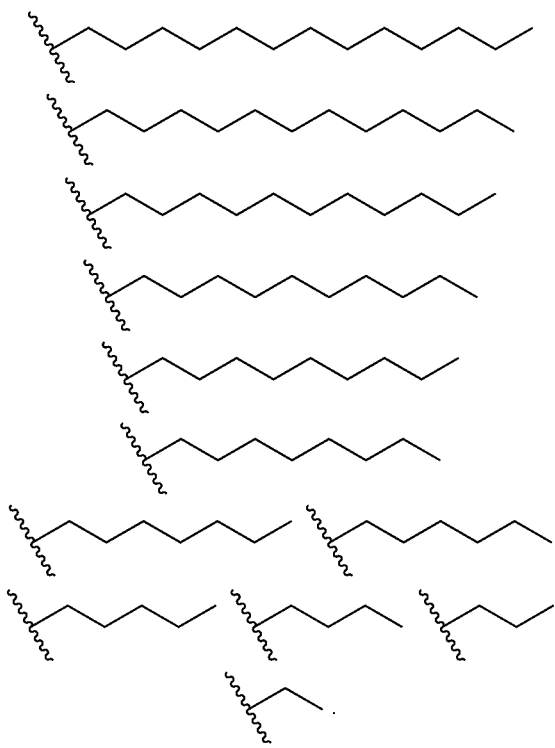

As would be appreciated by one of skill in this art, any of the above alkyl groups may be substituted, branched, unsaturated, and/or cyclic. In certain particular embodiments, $R_3$ is —CO$_2$R$_C$, wherein $R_C$ is aryl or arylalkyl. In certain particular embodiments, $R_3$ is —CO$_2$R$_C$, wherein $R_C$ is of the formula:

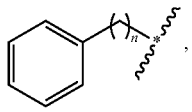

wherein n is an integer between 0 and 12, inclusive. In certain embodiments, n is 0. In certain embodiments, n is 1. In other embodiments, n is 2, 3, 4, 5, or 6. In certain particular embodiments, $R_3$ is —CO$_2$R$_C$, wherein $R_C$ is of the formula:

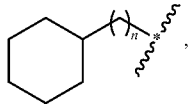

wherein n is an integer between 0 and 12, inclusive. In certain embodiments, n is 0. In certain embodiments, n is 1. In other embodiments, n is 2, 3, 4, 5, or 6.

In other embodiments, $R_1$ is —CO$_2$R$_A$, and $R_2$ and $R_3$ are both methyl. In certain embodiments, $R_1$ is —CO$_2$R$_A$, and $R_2$ and $R_3$ are both fluorine. In certain embodiments, $R_1$ is —CO$_2$R$_A$, and $R_2$ and $R_3$ are fluorine or trifluoromethyl.

Exemplary trisubstituted fluorinated monomers include:

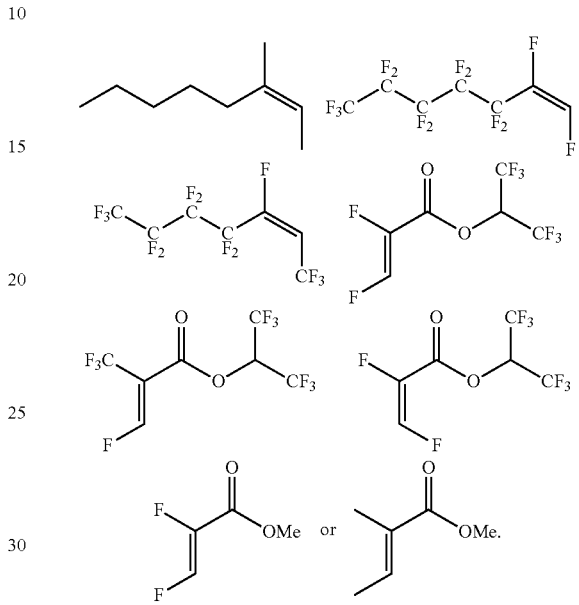

In certain embodiments, the tetrasubstituted alkene-containing compound useful in the treatment of hair is of one of the formulae:

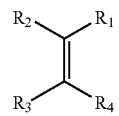

wherein
$R_1$, $R_2$, $R_3$ and $R_4$ are each independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$_A$; —C(O)R$_A$; —CO$_2$R$_A$; —C(O)N(R$_A$)$_2$; —SR$_A$; —SOR$_A$; —SO$_2$R$_A$; —NR$_A$; —N(R$_A$)$_2$; —NHC(O)R$_A$; and —C(R$_A$)$_3$;
wherein
each occurrence of $R_A$ is independently selected from a group consisting of hydrogen, cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; alkoxy; aryloxy; alkylthio; arylthio; amino; alkylamino; dialkylamino; heteroaryloxy; heteroarylthio and a protecting group;

or $R_1$, $R_2$, $R_3$ and/or $R_4$ may form a cyclic structure;
provided that $R_1$, $R_2$, $R_3$ and $R_4$ are not simultaneously hydrogen.

In other embodiments, $R_1$ is a substituted or unsubstituted, branched or unbranched aliphatic moiety. In certain embodiments, $R_1$ is an alkyl moiety. In certain embodiments, $R_1$ is of one of the formulae:

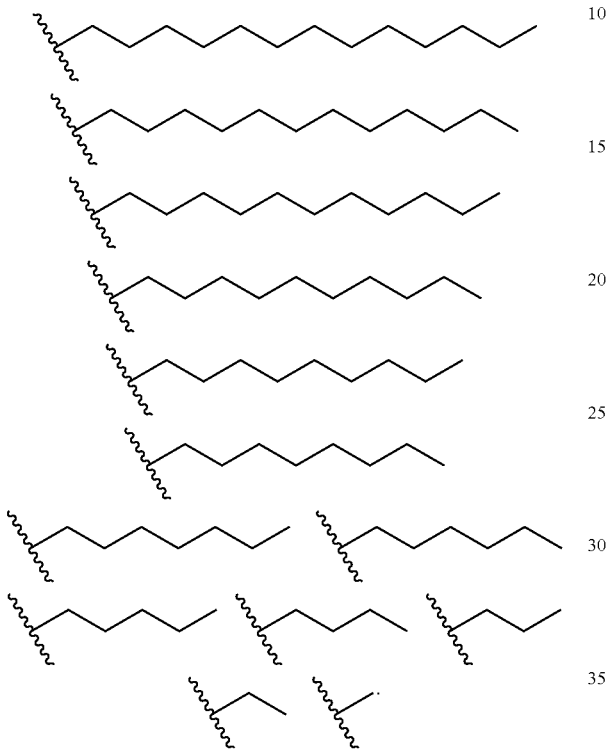

As would be appreciated by one of skill in this art, any of the above alkyl groups may be partially substituted, branched, unsaturated, and/or cyclic.

In certain particular embodiments. $R_1$ is one of the formulae:

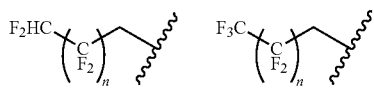

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive. In certain embodiments, n is an integer between 3 and 20, inclusive.

In certain embodiments, $R_1$ is one of the formulae:

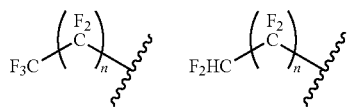

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive. In certain embodiments, n is an integer between 3 and 20, inclusive.

In certain particular embodiments, $R_1$ is of the formula:

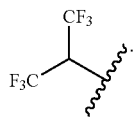

In certain particular embodiments, $R_1$ is of the formula:

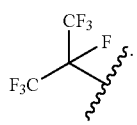

In yet other embodiments, $R_1$ is a substituted or unsubstituted, branched or unbranched heteroaliphatic moiety. In still other embodiments, $R_1$ is a substituted or unsubstituted acyl moiety.

In other embodiments, $R_1$ is a substituted or unsubstituted aryl moiety. In certain particular embodiments, $R_1$ is of the formula:

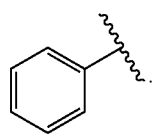

In certain particular embodiments, $R_1$ is of the formula:

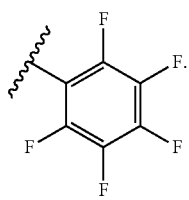 [SMILES: *c1c(F)c(F)c(F)c(F)c1F]

In certain particular embodiments, $R_1$ is of the formula:

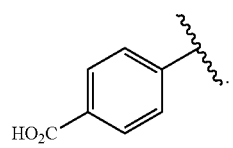

In certain particular embodiments, $R_1$ is a substituted or unsubstituted phenyl moiety. In certain embodiments, $R_1$ is substituted phenyl moiety (e.g., a phenyl ring with 1, 2, 3, 4, or 5 substituents). In other embodiments, $R_1$ is a substituted or unsubstituted heteroaryl moiety.

In certain embodiments, $R_1$ is —C(O)$R_4$. In other embodiments, $R_1$ is —CO$_2$$R_4$. In certain embodiments, $R_4$ is $C_1$-$C_6$ alkyl. In certain particular embodiments, $R_4$ is methyl. In certain embodiments, $R_4$ is

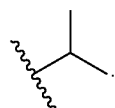

In other embodiments, $R_A$ is t-butyl. In certain particular embodiments, $R_1$ is $—CO_2R_A$, wherein $R_A$ is one of the formulae:

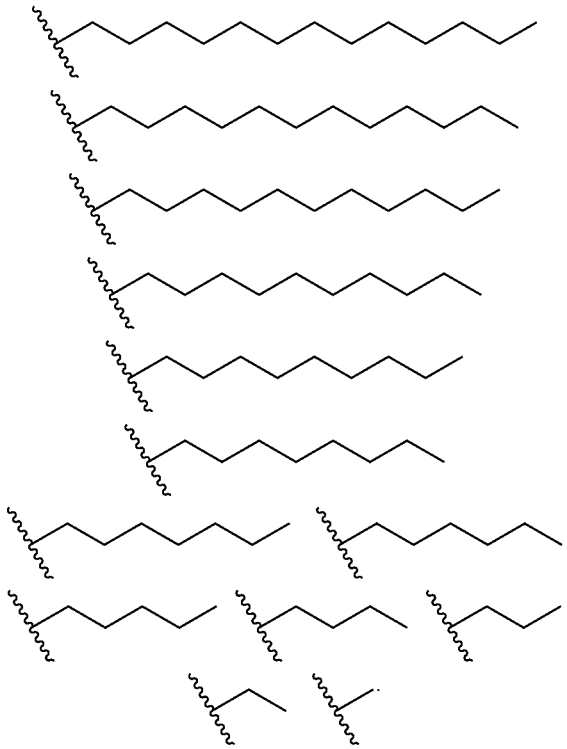

As would be appreciated by one of skill in this art, any of the above alkyl groups may be substituted, branched, unsaturated, and/or cyclic.

In certain particular embodiments, $R_1$ is $—CO_2R_A$, wherein $R_A$ is selected from the group consisting of:

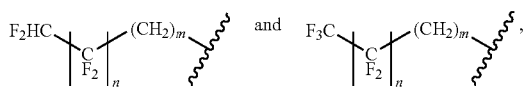

wherein n is an integer between 0 and 20, inclusive; and m is an even or odd integer between 1 and 6, inclusive.

In certain particular embodiments, $R_1$ is $—CO_2R_A$, wherein $R_A$ is one of the formulae:

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive.

In certain particular embodiments, $R_1$ is $—CO_2R_A$, wherein $R_A$ is of the

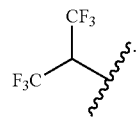

In certain particular embodiments, $R_1$ is $—CO_2R_A$, wherein $R_A$ is of the formulae:

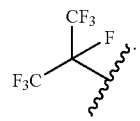

In certain particular embodiments, $R_1$ is $—CO_2R_A$, wherein $R_A$ is aryl or arylalkyl. In certain particular embodiments, $R_1$ is $—CO_2R_A$, wherein $R_A$ is of the formula:

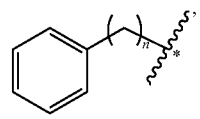

wherein n is an integer between 0 and 12, inclusive. In certain embodiments, n is 0. In certain embodiments, n is 1. In other embodiments, n is 2, 3, 4, 5, or 6. In certain particular embodiments, $R_1$ is $—CO_2R_A$, wherein $R_A$ is of the formula:

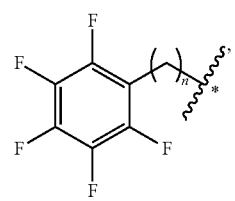

wherein n is an integer between 0 and 12, inclusive. In certain particular embodiments, $R_1$ is $—CO_2R_A$, wherein $R_A$ is of the formula:

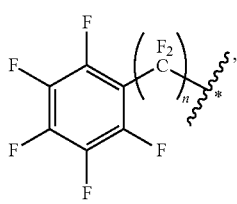

wherein n is an integer between 0 and 12, inclusive. In certain embodiments, n is 0. In certain embodiments, n is 1. In other embodiments, n is 2, 3, 4, 5, or 6. In certain particular embodiments, $R_1$ is $—CO_2R_A$, wherein $R_A$ is of the formula:

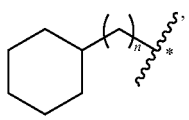

wherein n is an integer between 0 and 12, inclusive. In certain embodiments, n is 0. In certain embodiments, n is 1. In other embodiments, n is 2, 3, 4, 5, or 6. In certain particular embodiments, $R_1$ is —$CO_2R_A$, wherein $R_A$ is of the formula:

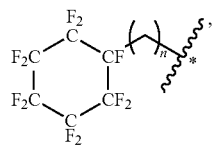

wherein n is an integer between 0 and 12, inclusive. In certain particular embodiments, $R_1$ is —$CO_2R_A$, wherein $R_A$ is of the formula:

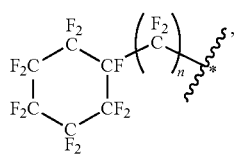

wherein n is an integer between 0 and 12, inclusive. In certain embodiments, n is 0. In certain embodiments, n is 1. In other embodiments, n is 2, 3, 4, 5, or 6.

In certain embodiments, $R_1$, $R_2$, $R_3$ or $R_4$ contains at least one halogen, provided that each is not simultaneously halogen. In certain embodiments, $R_1$, $R_2$, $R_3$ or $R_4$ contains at least one fluorine, but each is not simultaneously fluorine.

In other embodiments, $R_2$ is substituted or unsubstituted, branched or unbranched aliphatic. In yet other embodiments, $R_2$ is $C_1$-$C_6$ alkyl. In certain embodiments, $R_2$ is a alkyl moiety. In certain particular embodiments, $R_2$ is methyl. In certain particular embodiments, $R_2$ is ethyl. In certain embodiments, $R_2$ is propyl. In certain embodiments, $R_2$ is butyl. In certain embodiments, $R_2$ is trifluoromethyl. In certain embodiments, $R_2$ is a aryl or heteroaryl moiety. In certain embodiments, $R_2$ is a phenyl moiety. In certain particular embodiments, $R_2$ is a phenyl moiety.

In certain embodiments, $R_2$ is of one of the formulae:

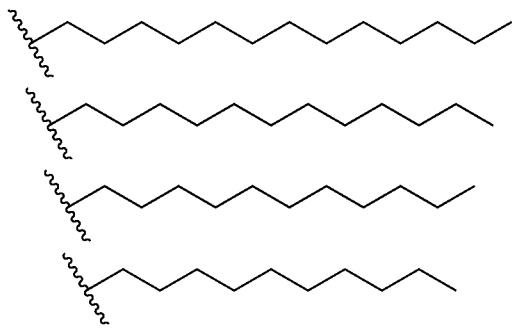

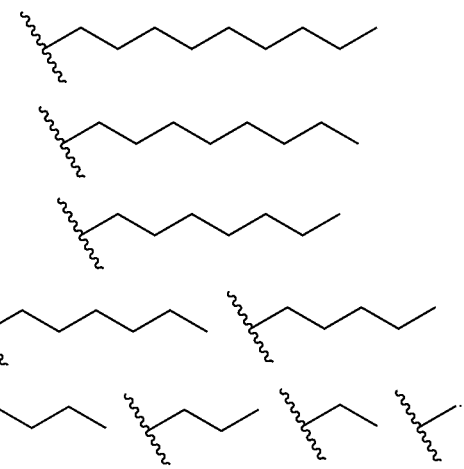

As would be appreciated by one of skill in this art, any of the above alkyl groups may be substituted, branched, unsaturated, and/or cyclic.

In certain particular embodiments, $R_2$ is one of the formulae:

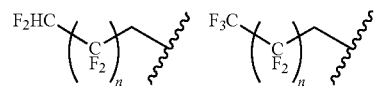

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive. In certain embodiments, n is an integer between 3 and 20, inclusive.

In certain embodiments. $R_2$ is one of the formulae:

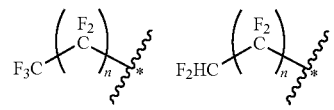

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive. In certain embodiments, n is an integer between 3 and 20, inclusive.

In certain particular embodiments, $R_2$ is of the formula:

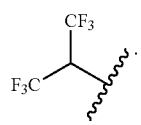

In certain particular embodiments, R$_2$ is of the formula:

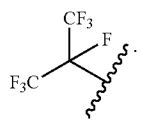

In yet other embodiments, R$_2$ is a substituted or unsubstituted, branched or unbranched heteroaliphatic moiety. In still other embodiments, R$_2$ is a substituted or unsubstituted acyl moiety.

In other embodiments, R$_2$ is a substituted or unsubstituted aryl moiety. In certain particular embodiments, R$_2$ is of the formula:

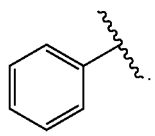

In certain particular embodiments, R$_1$ is of the formula:

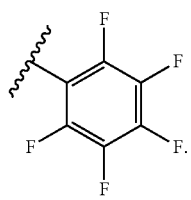 [SMILES: *c1c(F)c(F)c(F)c(F)c1F]

In certain particular embodiments, R$_2$ is of the formula:

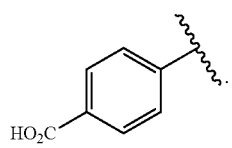

In certain particular embodiments, R$_2$ is a substituted or unsubstituted phenyl moiety. In certain embodiments, R$_2$ is substituted phenyl moiety (e.g., a phenyl ring with 1, 2, 3, 4, or 5 substituents). In other embodiments, R$_2$ is a substituted or unsubstituted heteroaryl moiety.

In certain embodiments, R$_2$ is —C(O)R$_B$. In other embodiments, R$_2$ is —CO$_2$R$_B$. In certain embodiments, R$_B$ is C$_1$-C$_6$ alkyl. In certain particular embodiments, R$_B$ is methyl. In certain embodiments, R$_B$ is

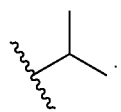

In other embodiments, R$_B$ is t-butyl. In certain particular embodiments, R$_2$ is —CO$_2$R$_B$, wherein R$_B$ is one of the formulae:

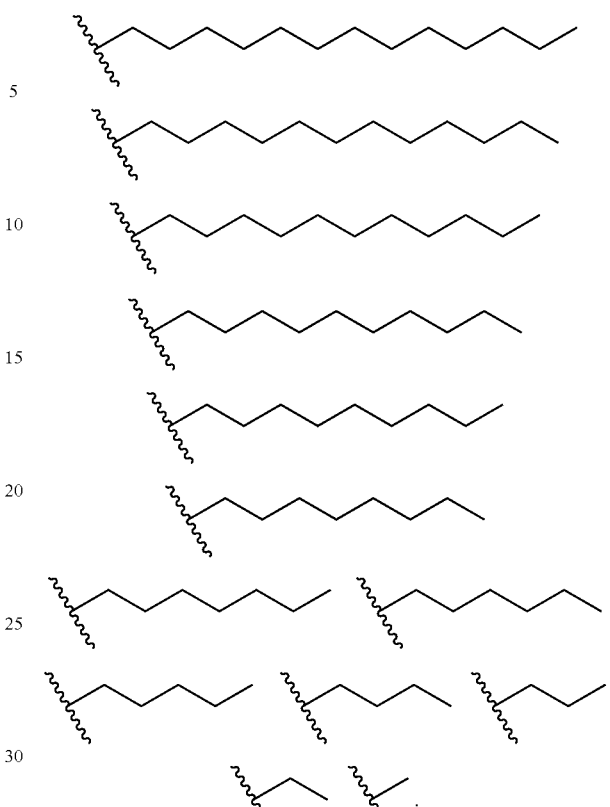

As would be appreciated by one of skill in this art, any of the above alkyl groups may be substituted, branched, unsaturated, and/or cyclic.

In certain particular embodiments, R$_2$ is —CO$_2$R$_B$, wherein R$_B$ is selected from the group consisting of:

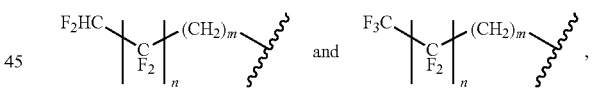

wherein n is an integer between 0 and 20, inclusive; and m is an even or odd integer between 1 and 6, inclusive.

In certain particular embodiments, R$_2$ is —CO$_2$R$_B$, wherein R$_B$ is one of the formulae:

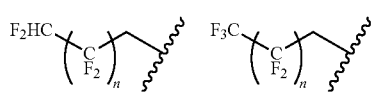

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive.

In certain particular embodiments, $R_2$ is $-CO_2R_B$, wherein $R_B$ is of the formulae:

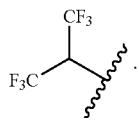

In certain particular embodiments, $R_2$ is $-CO_2R_B$, wherein $R_B$ is of the formulae:

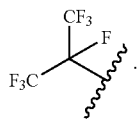

In certain particular embodiments, $R_2$ is $-CO_2R_B$, wherein $R_B$ is aryl or arylalkyl. In certain particular embodiments, $R_2$ is $-CO_2R_B$, wherein $R_B$ is of the

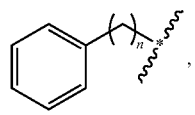

wherein n is an integer between 0 and 12, inclusive. In certain embodiments, n is 0. In certain embodiments, n is 1. In other embodiments, n is 2, 3, 4, 5, or 6. In certain particular embodiments, $R_2$ is $-CO_2R_B$, wherein $R_B$ is of the formula:

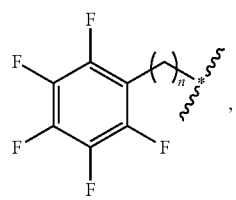

wherein n is an integer between 0 and 12, inclusive. In certain particular embodiments, $R_2$ is $-CO_2R_B$, wherein $R_B$ is of the formula:

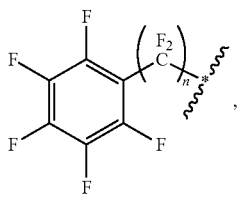

wherein n is an integer between 0 and 12, inclusive. In certain embodiments, n is 0. In certain embodiments, n is 1. In other embodiments, n is 2, 3, 4, 5, or 6. In certain particular embodiments, $R_2$ is $-CO_2R_B$, wherein $R_B$ is of the formula:

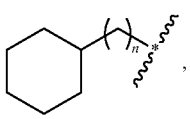

wherein n is an integer between 0 and 12, inclusive. In certain embodiments, n is 0. In certain embodiments, n is 1. In other embodiments, n is 2, 3, 4, 5, or 6. In certain particular embodiments, $R_2$ is $-CO_2R_B$, wherein $R_B$ is of the formula:

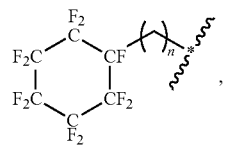

wherein n is an integer between 0 and 12, inclusive. In certain particular embodiments, $R_2$ is $-CO_2R_B$, wherein $R_B$ is of the formula:

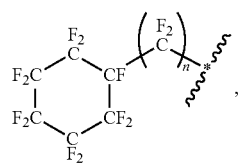

wherein n is an integer between 0 and 12, inclusive. In certain embodiments, n is 0. In certain embodiments, n is 1. In other embodiments, n is 2, 3, 4, 5, or 6.

In certain embodiments, $R_3$ is halogen. In certain embodiments, $R_3$ is fluorine.

In certain embodiments, $R_3$ is substituted or unsubstituted, branched or unbranched aliphatic. In yet other embodiments, $R_3$ is $C_1$-$C_6$ alkyl. In certain particular embodiments, $R_3$ is methyl. In certain particular embodiments, $R_3$ is ethyl. In certain embodiments, $R_3$ is propyl. In certain embodiments, $R_3$ is butyl. In certain embodiments, $R_3$ is trifluoromethyl. In certain embodiments, $R_3$ is a aryl or heteroaryl moiety. In certain embodiments, $R_3$ is a phenyl moiety. In certain particular embodiments, $R_3$ is a phenyl moiety.

In certain embodiments, $R_3$ is of one of the formulae:

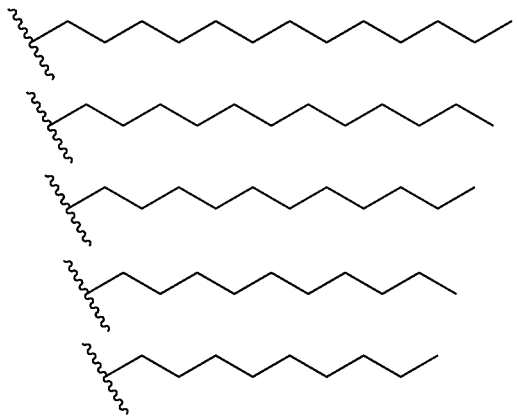

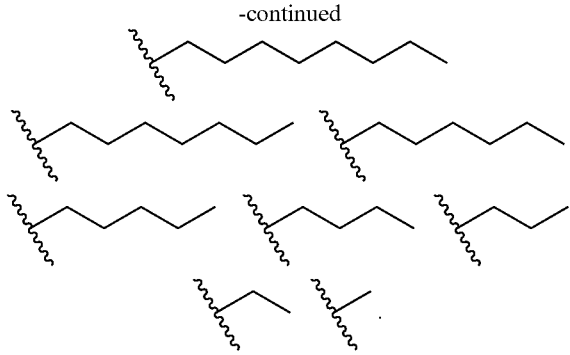

As would be appreciated by one of skill in this art, any of the above alkyl groups may be substituted, branched, unsaturated, and/or cyclic.

In certain particular embodiments, $R_3$ is one of the formulae:

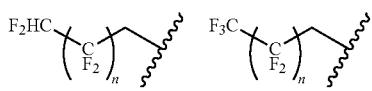

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive. In certain embodiments, n is an integer between 3 and 20, inclusive.

In certain embodiments, $R_3$ is one of the formulae:

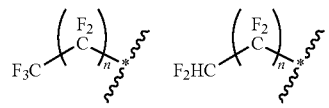

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive. In certain embodiments, n is an integer between 3 and 20, inclusive.

In certain particular embodiments, $R_3$ is of the formula:

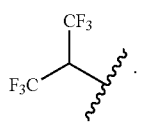

In certain particular embodiments, $R_3$ is of the formula:

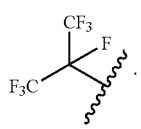

In yet other embodiments, $R_3$ is a substituted or unsubstituted, branched or unbranched heteroaliphatic moiety. In still other embodiments, $R_3$ is a substituted or unsubstituted acyl moiety.

In other embodiments, $R_3$ is a substituted or unsubstituted aryl moiety. In certain particular embodiments, $R_3$ is of the formula:

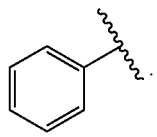 [SMILES: *c1ccccc1]

In certain particular embodiments, $R_3$ is of the formula:

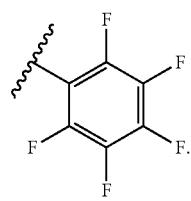 [SMILES: *c1c(F)c(F)c(F)c(F)c1F]

In certain particular embodiments, $R_3$ is of the formula:

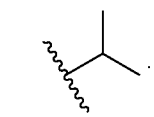 [SMILES: *C(C)C]

In certain particular embodiments, $R_3$ is a substituted or unsubstituted phenyl moiety. In certain embodiments, $R_3$ is a substituted phenyl (e.g., a phenyl ring with 1, 2, 3, 4, or 5 substituents). In other embodiments, $R_3$ is a substituted or unsubstituted heteroaryl moiety.

In certain embodiments, $R_3$ is —C(O)$R_D$. In other embodiments, $R_3$ is —CO$_2R_C$. In certain embodiments, $R_C$ is $C_1$-$C_6$ alkyl. In certain particular embodiments, $R_C$ is methyl. In certain embodiments, $R_C$ is In other embodiments, $R_C$ is t-butyl. In certain particular embodiments, $R_3$ is —CO$_2R_C$, wherein $R_C$ is one of the formulae:

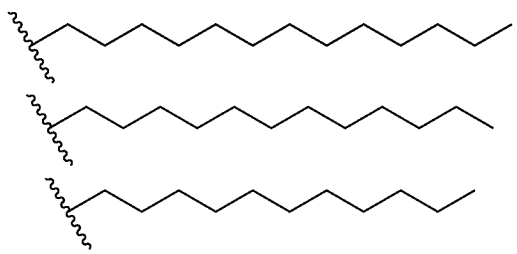

-continued

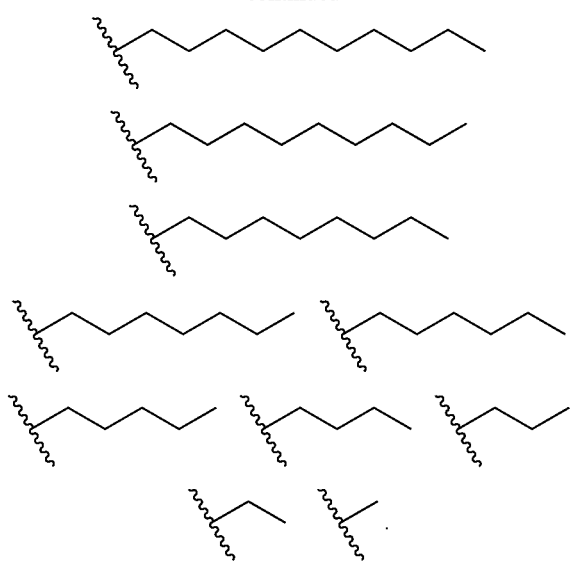

As would be appreciated by one of skill in this art, any of the above alkyl groups may be substituted, branched, unsaturated, and/or cyclic.

In certain particular embodiments, $R_3$ is —$CO_2R_C$, wherein $R_C$ selected from the group consisting of:

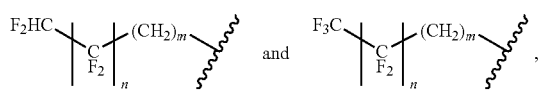

wherein n is an integer between 0 and 20, inclusive; and m is an even or odd integer between 1 and 6, inclusive.

In certain particular embodiments, $R_3$ is —$CO_2R_C$, wherein $R_C$ is one of the formulae:

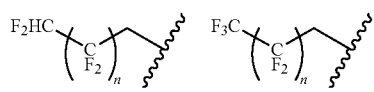

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive.

In certain particular embodiments, $R_3$ is —$CO_2R_C$, wherein $R_C$ is of the formulae:

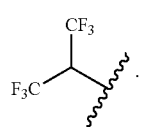

In certain particular embodiments, $R_3$ is —$CO_2R_C$, wherein $R_C$ is of the formulae:

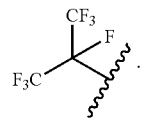

In certain particular embodiments, $R_3$ is —$CO_2R_C$, wherein $R_C$ is aryl or arylalkyl. In certain particular embodiments, $R_3$ is —$CO_2R_C$, wherein $R_C$ is of the formula:

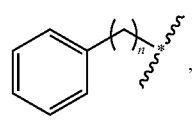

wherein n is an integer between 0 and 12, inclusive. In certain embodiments, n is 0. In certain embodiments, n is 1. In other embodiments, n is 2, 3, 4, 5, or 6. In certain particular embodiments, $R_3$ is —$CO_2R_C$, wherein $R_C$ is of the formula:

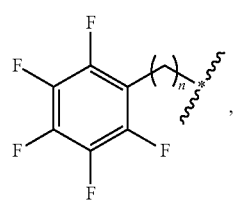

wherein n is an integer between 0 and 12, inclusive. In certain particular embodiments, $R_3$ is —$CO_2R_C$, wherein $R_C$ is of the formula:

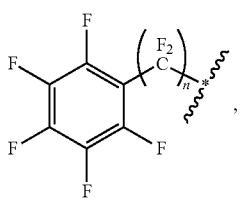

wherein n is an integer between 0 and 12, inclusive. In certain embodiments, n is 0. In certain embodiments, n is 1. In other embodiments, n is 2, 3, 4, 5, or 6. In certain particular embodiments, $R_3$ is —$CO_2R_C$, wherein $R_C$ is of the formula:

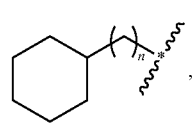

wherein n is an integer between 0 and 12, inclusive. In certain embodiments, n is 0. In certain embodiments, n is 1. In other embodiments, n is 2, 3, 4, 5, or 6. In certain particular embodiments, $R_3$ is —$CO_2R_C$, wherein $R_C$ is of the formula:

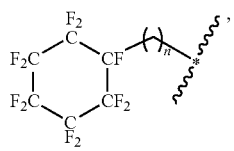

wherein n is an integer between 0 and 12, inclusive. In certain particular embodiments, $R_3$ is —$CO_2R_C$, wherein $R_C$ is of the formula:

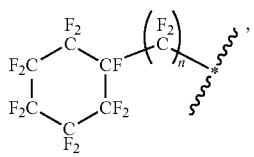

wherein n is an integer between 0 and 12, inclusive. In certain embodiments, n is 0. In certain embodiments, n is 1. In other embodiments, n is 2, 3, 4, 5, or 6.

In certain embodiments, $R_4$ is halogen. In certain embodiments, $R_4$ is fluorine.

In other embodiments, $R_4$ is substituted or unsubstituted, branched or unbranched aliphatic. In yet other embodiments, $R_4$ is $C_1$-$C_6$ alkyl. In certain particular embodiments, $R_4$ is methyl. In certain particular embodiments, $R_4$ is ethyl. In certain embodiments, $R_4$ is propyl. In certain embodiments, $R_4$ is butyl. In certain embodiments, $R_4$ is trifluoromethyl. In certain embodiments, $R_4$ is a aryl or heteroaryl moiety. In certain embodiments, $R_4$ is a phenyl moiety. In certain particular embodiments, $R_4$ is a phenyl moiety.

In certain embodiments, $R_4$ is of one of the formulae:

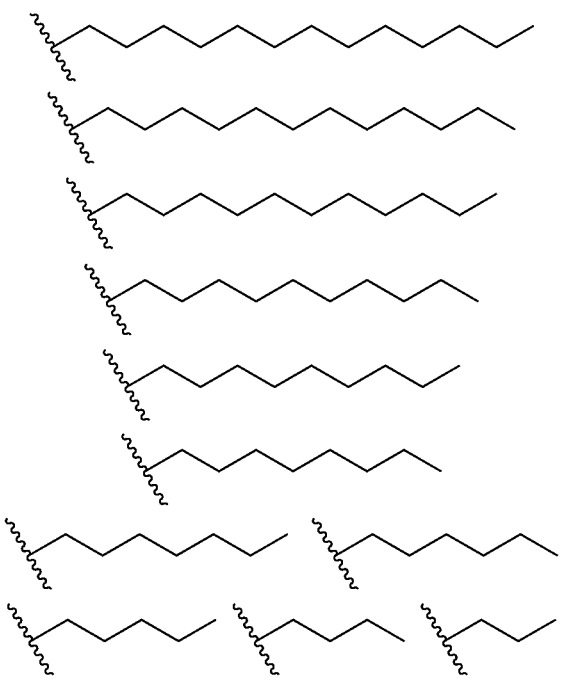

-continued

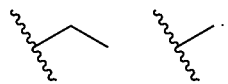

As would be appreciated by one of skill in this art, any of the above alkyl groups may be substituted, branched, unsaturated, and/or cyclic.

In certain embodiments, $R_4$ is one of the formulae:

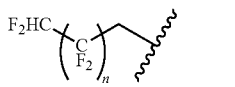 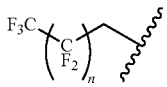

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive. In certain embodiments, n is an integer between 3 and 20, inclusive.

In certain embodiments, $R_4$ is one of the formulae:

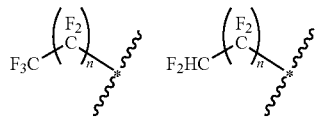

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive. In certain embodiments, n is an integer between 3 and 20, inclusive.

In certain embodiments, $R_4$ is of the formula:

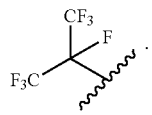

In certain embodiments, $R_4$ is of the formula:

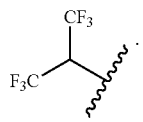

In yet other embodiments, $R_4$ is a substituted or unsubstituted, branched or unbranched heteroaliphatic moiety. In still other embodiments, $R_4$ is a substituted or unsubstituted acyl moiety.

In other embodiments, $R_4$ is a substituted or unsubstituted aryl moiety. In certain particular embodiments, $R_4$ is of the formula:

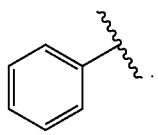 [SMILES: *c1ccccc1]

In certain particular embodiments, $R_1$ is of the formula:

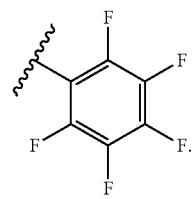 [SMILES: *c1c(F)c(F)c(F)c(F)c1F]

In certain particular embodiments, $R_4$ is of the formula:

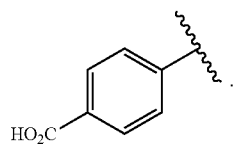 [SMILES: *c1ccc(C(=O)O)cc1]

In certain particular embodiments, $R_4$ is a substituted or unsubstituted phenyl moiety. In certain embodiments, $R_4$ is substituted phenyl moiety (e.g., a phenyl ring with 1, 2, 3, 4, or 5 substituents). In other embodiments, $R_4$ is a substituted or unsubstituted heteroaryl moiety.

In certain embodiments, $R_4$ is $-C(O)R_D$. In other embodiments, $R_4$ is $-CO_2R_D$. In certain embodiments, $R_D$ is $C_1$-$C_6$ alkyl. In certain particular embodiments, $R_D$ is methyl. In certain particular embodiments, $R_A$ is trifluoromethyl. In certain embodiments, $R_D$ is

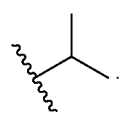 [SMILES: *C(C)C]

In certain embodiments, $R_D$ is

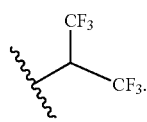

In certain embodiments, $R_D$ is

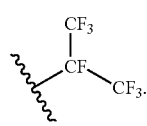

In other embodiments, $R_D$ is t-butyl. In certain particular embodiments, $R_4$ is $-CO_2R_D$, wherein $R_D$ is one of the formulae:

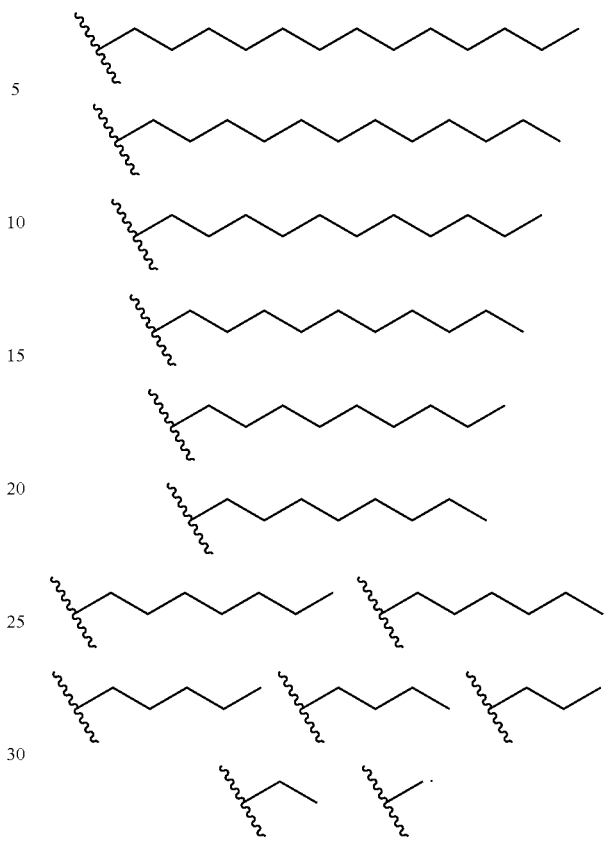

As would be appreciated by one of skill in this art, any of the above alkyl group may be substituted, branched, unsaturated, and/or cyclic.

In certain particular embodiments, $R_4$ is $-CO_2R_D$, wherein $R_D$ is selected from the group consisting of:

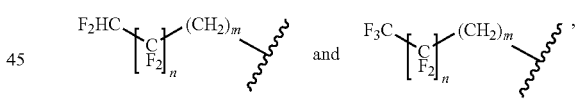

wherein n is an integer between 0 and 20, inclusive; and m is an even or odd integer between 1 and 6, inclusive.

In certain particular embodiments, $R_4$ is $-CO_2R_D$, wherein $R_D$ is one of the formulae:

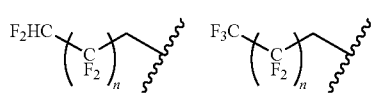

wherein n is an integer between 0 and 20, inclusive. In certain embodiments, n is an integer between 0 and 12, inclusive. In certain embodiments, n is an integer between 0 and 6, inclusive. In certain embodiments, n is an integer between 1 and 6, inclusive.

In certain particular embodiments, $R_4$ is $-CO_2R_D$, wherein $R_D$ is of the formulae:

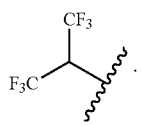

In certain particular embodiments, $R_4$ is —$CO_2R_D$, wherein $R_D$ is of the formulae:

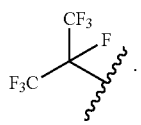

In certain particular embodiments, $R_4$ is —$CO_2R_D$, wherein $R_D$ is aryl or arylalkyl. In certain particular embodiments, $R_4$ is —$CO_2R_D$, wherein $R_D$ is of the formula:

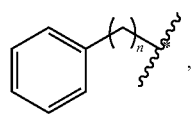

wherein n is an integer between 0 and 12, inclusive. In certain embodiments, n is 0. In certain embodiments, n is 1. In other embodiments, n is 2, 3, 4, 5, or 6. In certain particular embodiments, $R_4$ is —$CO_2R_D$, wherein $R_D$ is of the formula:

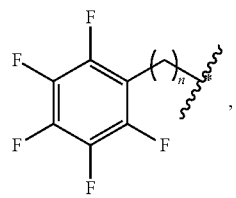

wherein n is an integer between 0 and 12, inclusive. In certain particular embodiments, $R_4$ is —$CO_2R_D$, wherein $R_D$ is of the formula:

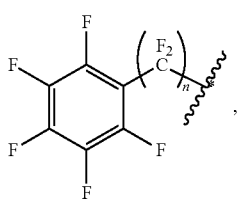

wherein n is an integer between 0 and 12, inclusive. In certain embodiments, n is 0. In certain embodiments, n is 1. In other embodiments, n is 2, 3, 4, 5, or 6. In certain particular embodiments, $R_4$ is —$CO_2R_D$, wherein $R_D$ is of the formula:

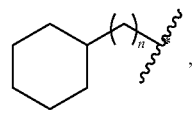

wherein n is an integer between 0 and 12, inclusive. In certain embodiments, n is 0. In certain embodiments, n is 1. In other embodiments, n is 2, 3, 4, 5, or 6. In certain particular embodiments, $R_4$ is —$CO_2R_D$, wherein $R_D$ is of the formula:

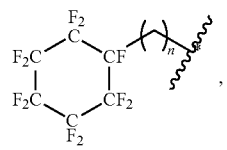

wherein n is an integer between 0 and 12, inclusive. In certain embodiments, n is 0. In certain embodiments, n is 1. In other embodiments, n is 2, 3, 4, 5, or 6.

In other embodiments, $R_1$ is —$CO_2R_4$, and $R_2$ and $R_3$ are both methyl. In certain embodiments, at least one of $R_1$, $R_2$, $R_3$, and $R_4$ is fluorine. In certain embodiments, at least two of $R_1$, $R_2$, $R_3$, and $R_4$ is fluorine. In certain embodiments, at least three of $R_1$, $R_2$, $R_3$, and $R_4$ is fluorine. In certain embodiments, at least one of $R_1$, $R_2$, $R_3$, and $R_4$ is $C_1$-$C_6$ alkyl. In certain embodiments, at least one of $R_1$, $R_2$, $R_3$, and $R_4$ is methyl. In certain embodiments, at least one of $R_1$, $R_2$, $R_3$, and $R_4$ is trifluoromethyl.

Exemplary tetrasubstituted compounds include:

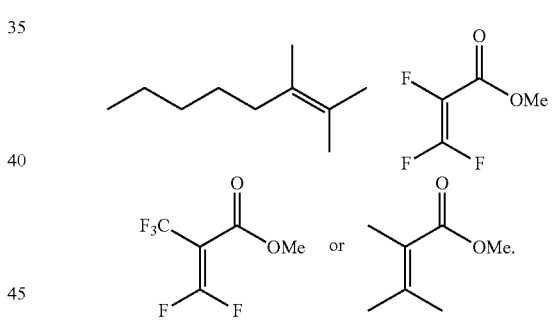

In certain embodiments, the compound useful in the treatment of hair is mixed with one or more different compounds. The resulting combination may be applied to hair. As would be appreciated by those of skill in this art, a combination of compounds may have desirable properties not attainable with a single compound alone. In certain embodiments, two different compounds are applied to hair. In other embodiments, three different compounds are applied to hair. When multiple different compounds are used, the compounds are applied to hair simultaneously or separately. In certain embodiments, the compounds are all in the same composition which is applied to the hair.

Exemplary compounds useful in accordance with the present invention include trimethylolpropane trimethacrylate; 1,3-bis(3-methacryloyloxypropyl)-1,1,3,3-tetramethyl-disiloxane; 1,3-butanediol dimethacrylate; 1,4-butanediol dimethacrylate; 1,6-hexanediol dimethacrylate; bisphenol A dimethacrylate; bisphenol A ethoxylate dimethacrylate; bisphenol A glycerolate dimethacrylate; di(ethylene glycol) dimethacrylate; diurethane dimethacrylate, mixture of isomers; ethylene glycol dimethacrylate; glycerol dimethacrylate, mixture of isomers; neopentyl glycol dimethacrylate; poly(ethylene glycol) dimethacrylate; poly(lauryl methacrylate-co-ethylene glycol dimethacrylate); poly(methyl methacrylate-co-ethylene glycol dimethacrylate); poly(propylene glycol) dimethacrylate; tetraethylene glycol dimethacrylate; triethylene glycol dimethacrylate; 1,1,1,3,3,3-hexafluoroisopropyl methacrylate; 2-(9H-carbazol-9-yl)ethyl acrylate; 2-(diethylamino)ethyl methacrylate; 2-(dimethylamino)ethyl methacrylate; 2-(methacryloyloxy)ethyl acetoacetate; 2-(methylthio)ethyl methacrylate; 2-(tert-butylamino)ethyl methacrylate; 2-(trimethylsilyloxy)ethyl methacrylate; 2,2,2-trifluoroethyl methacrylate; 2,2,3,3,3-pentafluoropropyl methacrylate; 2,2,3,3,4,4,4-heptafluorobutyl methacrylate; 2,2,3,3,4,4,5,5-octafluoropentyl methacrylate; 2,2,3,4,4,4-hexafluorobutyl methacrylate; 2-[3-(2H-benzotriazol-2-yl)-4-hydroxyphenyl]ethyl methacrylate; 2-aminoethyl methacrylate hydrochloride; 2-butoxyethyl methacrylate; 2-ethoxyethyl methacrylate; 2-ethylhexyl methacrylate; 2-hydroxyethyl methacrylate; 2-methyl-2-nitropropyl methacrylate; 2-naphthyl methacrylate; 3-(acryloyloxy)-2-hydroxypropyl methacrylate; 3-(diethoxymethylsilyl)propyl methacrylate; 3-(dimethylchlorosilyl)propyl methacrylate; 3-(trichlorosilyl)propyl methacrylate; 3-(dimethylchlorosilyl)propyl methacrylate; 3-(trichlorosilyl)propyl methacrylate; 3-(trimethoxysilyl)propyl methacrylate; 3,3,4,4,5,5,6,6,6,-nonafluorohexyl methacrylate; 3,3,4,4,5,5,6,6,7,7,8,8,8-tridecafluorooctyl methacrylate; 3,3,4,4,5,5,6,6,7,7,8,8,9,10,10,10-hexadecafluoro-9-trifluoromethyl)decyl methacrylate; 3,3,4,4,5,5,6,6,7,7,8,8,9,9,10,10,10-heptadecafluorodecyl methacrylate; 3,3,4,4,5,5,6,6,7,7,8,8,9,9,10,10,11,11,12,12,12-heneicosafluorododecyl methacrylate; 3,3,4,4,5,5,6,6,7,7,8,8,9,9,10,10,11,12,12,12-eicosafluoro-11-(trifluoromethyl)dodecyl methacrylate; 3,3,4,4,5,5,6,6,7,8,8,8-dodecafluoro-7-(trifluoromethyl)octyl methacrylate; 3,3,4,4,5,6,6,6-octafluoro-5-(trifluoromethyl)hexyl methacrylate; 3,3,5-trimethylcyclohexyl methacrylate, mixture of isomers; 3-[(3,5,7,9,11,13,15-heptacyclopentylpentacyclo[9.5.1.1$^{3,9}$.1$^{5,15}$.1$^{7,13}$]octasiloxan-1-yloxy)dimethylsilyl]propyl methacrylate; 3-[tris(trimethylsiloxy)silyl]propyl methacrylate; 3-chloro-2-hydroxypropyl methacrylate; 3-sulfopropyl methacrylate; 4,4,5,5,6,6,7,7,8,8,9,9,10,11,11,11-hexadecafluoro-2-hydroxy-10-(trifluoromethyl)undecyl methacrylate; 4,4,5,5,6,6,7,7,8,9,9,9-dodecafluoro-2-hydroxy-8-(trifluoromethyl)nonyl methacrylate; 4,4,5,5,6,7,7,7-octafluoro-2-hydroxy-6-(trifluoromethyl)heptyl methacrylate; 6-[4-(4-cyanophenyl)phenoxy]hexyl methacrylate; 9-anthracenylmethyl methacrylate; 9H-carbazole-9-ethylmethacrylate; allyl methacrylate; benzyl methacrylate; butyl methacrylate; cyclohexyl methacrylate; decyl methacrylate; di(ethylene glycol) ethyl ether methacrylate; di(ethylene glycol) methyl ether methacrylate; di(propylene glycol) allyl ether methacrylate, mixture of isomers; Disperse Red 1 methacrylate; Disperse Red 13 methacrylate; Disperse yellow 7 methacrylate; ethyl methacrylate; ethylene glycol dicyclopentenyl ether methacrylate; ethylene glycol methyl ether methacrylate; ethylene glycol phenyl ether methacrylate; furfuryl methacrylate; glycidyl methacrylate; glycol methacrylate; glycosyloxyethyl methacrylate; hexyl methacrylate; hydroxybutyl methacrylate, mixture of isomers; hydroxypropyl methacrylate; isobornyl methacrylate; isobutyl methacrylate; isodecyl methacrylate; lauryl methacrylate; methyl methacrylate; stearyl methacrylate; tert-butyl methacrylate; tetrahydrofurfuryl methacrylate; tridecyl methacrylate; trimethylsilyl methacrylate; vinyl methacrylate; glycerol propoxylate (1PO/OH) triacrylate; pentaerythritol triacrylate; trimethylolpropane ethoxylate triacrylate; trimethylolpropane propoxylate triacrylate; trimethylolpropane triacrylate; di(trimethylolpropane) tetraacrylate; pentaerythritol tetraacrylate; dipentaerythritol pentaacrylate; ethoxylated pentaerythritol tetraacrylate; low viscosity dipentaerythritol pentaacrylate; pentaacrylate ester; pentaerythritol tetraacrylate; trimethylolpropane triacrylate; ethoxylated trimethylolpropane triacrylate; propoxylated glycerol triacrylate; pentaerythritol triacrylate; propoxylated glyceryl triacrylate; propoxylated trimethylolpropane triacrylate; trimethylolpropane trimethacrylate; tris(2-hydroxy ethyl) isocyanurate triacrylate; tris(2-hydroxy ethyl) isocyanurate triacrylate; polybutadiene diacrylate; and polybutadiene dimethacrylate. In certain particular embodiments, the compound is ethyl acrylate; vinyl acrylate; 1,3-butanediol diacrylate; dipentaerythritol pentaacrylate; tridecyl methacrylate; styrene; and 3,4-epoxycyclohexylmethyl 3',4'-epoxycyclohexane carboxylate. In certain embodiments, the fluorinated compound for the treatment of hair is 1,1,1,3,3,3-hexafluoroisopropyl 2-fluoroacrylate, 1,1,1,3,3,3-hexafluoroisopropyl acrylate, 1,1,1,3,3,3-hexafluoroisopropyl methacrylate, 2,2,3,3,4,4,5,5-octafluoro-1,6-hexyl diacrylate, 2,2,3,3,4,4,5,5-octafluoro-1,6-hexyl dimethacrylate, 2,3,4,5,6-pentafluorostyrene, methyl pentafluoromethacrylate, methyl trifluoroacrylate, 4-allyl-2,3,5,6-tetrafluorobenzoic acid, heptafluoroisopropyl acrylate, hexafluoroisopropyl crotonate, hexafluoro-2-methylisopropyl acrylate, 1,1,1,3,3,3-hexafluoroisopropyl methacrylate, 1,1,1,3,3,3-hexafluoroisopropyl dimethacrylate, 1H,1H,5H-octafluoropentyl acrylate, 1H,1H,5H-octafluoropentyl methacrylate, pentafluorobenzyl acrylate, tert-butyl-2-(trifluoromethyl)acrylate, and 1H,1H,1H-eicosafluoroundecyl acrylate. In certain embodiments, the compound is a polybutadiene di(meth)acrylate oligomer. In certain embodiments, the compound is tricyclodecane dimethanol diacrylate. In certain embodiments, the compound is tricyclodecane dimethanol dimethacrylate. In certain embodiments, the compound is hexanediol acrylate. In certain embodiments, the compound is hexanediol diemethacrylate.

In certain embodiments, a fluorinated organic compound is applied to hair based on the inventive hair treatment system. The fluorinated compound typically comprises an unsaturated functional group and at least one fluorine atom. The unsaturated functional group includes a double bond or triple bond. Exemplary unsaturated functional groups include alkenes, alkynes, carbonyls, imines, thiocarbonyls, acrylates, methacrylates, acrylates, crotonates, styrenes, nitriles, cyano, vinyl, styrene, crotonate, cinnamate, dienes, trienes, eneynes, maleimides, etc.

The fluorinated compound may range from including one fluorine atom to being one fluorine atom less than being perfluorinated. In certain embodiments, a functional group of the compound is fluorinated such as, for example, an alkyl, alkenyl, alkynyl, acyl, aryl, heteroaryl, heterocyclic, or carbocyclic moiety. For example, the compound may include a trifluoromethyl group. In certain embodiments, the fluorinated compound includes at least 1, 2, 3, 4, 5, 6, 7, 8, 9, 10, 11, 12, 13, 14, 15, 16, 17, 18, 19, or 20 fluorine atoms. In other embodiments, the fluorinated compound contains at least 10, at least 15, at least 20, at least 25, at least 30, or at least 40 fluorine atoms. As would be appreciated by one of skill in this art, the larger the compound the more fluorine atoms the compound is likely to have. Furthermore, the compound applied to hair should include enough fluorine atoms so that the compound imparts the desired characteristics when applied to hair (e.g., look, feel).

In certain embodiments, at least 10%, 20%, 30%, 40%, 50%, 60%, 70%, 80%, 90%, 95%, or 99% of the total number of hydrogen and fluorine atoms are fluorine atoms in the fluorinated compound. In certain embodiments, at least 50% of the total number of hydrogen and fluorine atoms are fluorine atoms in the fluorinated compound. In certain embodiments, at least 80% of the total number of hydrogen and fluorine atoms are fluorine atoms in the fluorinated compound. In certain embodiments, at least 90% of the total number of hydrogen and fluorine atoms are fluorine atoms in the fluorinated compound.

In certain embodiments, the fluorinated compound is a fluorinated alkene. In certain particular embodiments, the fluorinated alkene is monosubstituted. In other embodiments, the fluorinated alkene is disubstituted. Disubstituted fluorinated alkene may be either in the cis or trans configuration or a mixture thereof. In yet other embodiments, the fluorinated alkene is trisubstituted. The trisubstituted fluorinated alkene may be in either the E or Z configuration or a mixture thereof. In still other embodiments, the fluorinated alkene is tetrasubstituted. Again, various isomers are possible and are considered part of this invention. In certain embodiments, the fluorinated compound is a fluorinated alkyne.

Exemplary monosubstituted fluorinated compounds include:

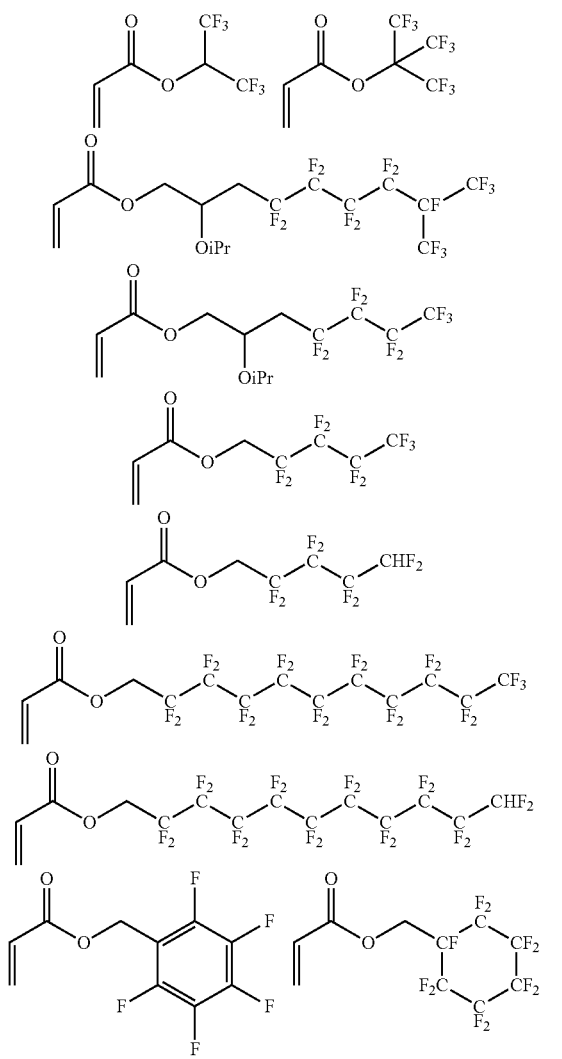

-continued

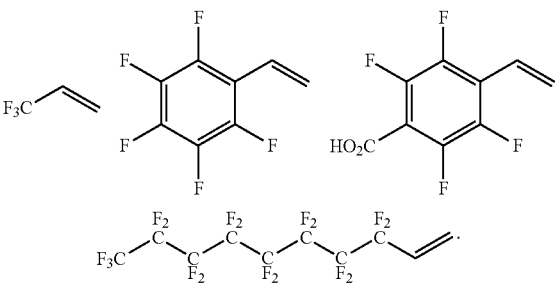

Exemplary disubstituted fluorinated compounds useful in the treatment of hair include:

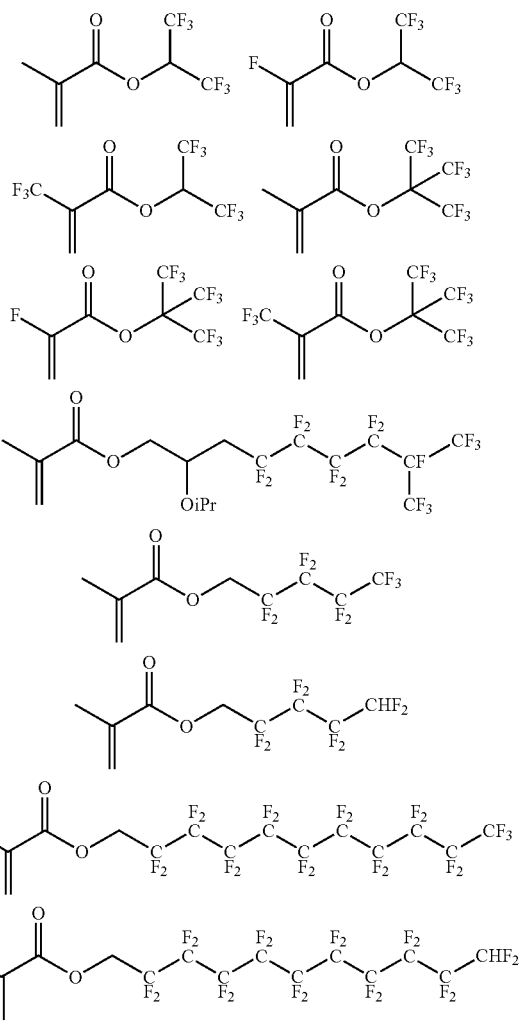

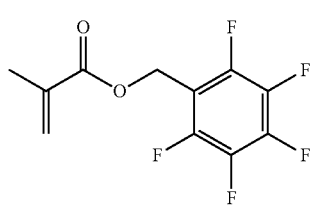

-continued

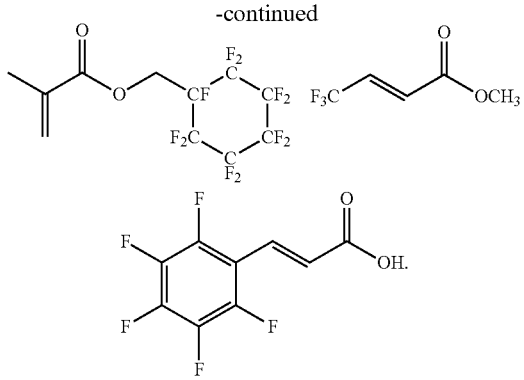

Exemplary trisubstituted fluorinated compounds include:

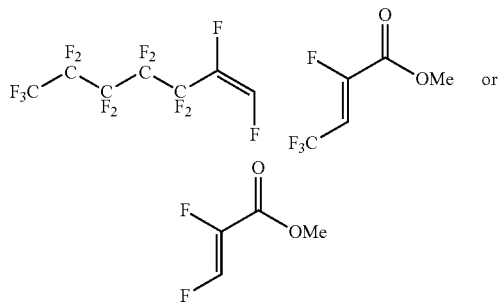

Exemplary tetrasubstituted fluorinated compounds useful in the treatment of hair include:

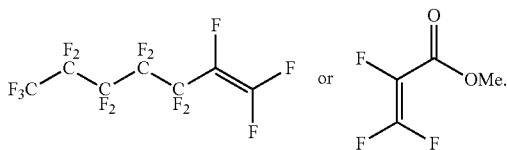 [SMILES: FC(F)=C(F)C(F)(F)C(F)(F)C(F)(F)C(F)(F)C(F)(F)F ; "or" ; COC(=O)C(F)=C(F)F]

In certain embodiments, the fluorinated compound is mixed with one or more different compound. As would be appreciated by those of skill in this art, a mixture may have desirable properties not attainable with one compound alone. In certain embodiments, two different compounds are applied to hair. In other embodiments, three different compounds are applied to hair. When different compounds are used, the compounds are applied to hair simultaneously or separately. In certain embodiments, the compounds are all in the same solution which is applied to the hair. In certain embodiments, one of the compounds is fluorinated, and another is not fluorinated. In other embodiments, all compounds are fluorinated.

The compounds described herein can be applied to hair using any method known in the art. The hair to be treated is brushed, sprayed, rubbed, dipped, soaked, etc. with the compound or a solution of the compound. In certain embodiments, the compound is dissolved in a carrier such as water, alcohol, water/alcohol or alcohol/water mixtures (between 5%/95% to 10%/90%, between 10%/90% to 20%/80%, between 20%/80% to 30%/70%, between 30%/70% to 40%/60%, and between 40%/60% to 50%/50%) or other carriers and applied to hair. The carrier may include a propellant such as difluoroethane or dimethyl ether. Typically, the concentration of the compound ranges from 0.1% to 10%. In certain embodiments, the concentration ranges from 0.1% to 3%. In other embodiments, the concentration ranges from 0.1% to 2%.

The compound is typically soluble in a variety of organic carriers (e.g., alcohol), propylene glycol, glycerol, water, or aqueous solutions. In certain embodiments, the compound has a solubility of at least 10 g/dL in a 50:50 water/ethanol solution. In certain embodiments, the compound has a solubility of at least 5 g/dL in a 50:50 water/ethanol solution. In certain embodiments, the compound has a solubility of at least 4 g/dL in a 50:50 water/ethanol solution. In certain embodiments, the compound has a solubility of at least 3 g/dL in a 50:50 water/ethanol solution. In certain embodiments, the compound has a solubility of at least 2 g/dL in a 50:50 water/ethanol solution. In certain embodiments, the compound has a solubility of at least 1 g/dL in a 50:50 water/ethanol solution. In certain embodiments, the compound has a solubility of at least 0.5 g/dL in a 50:50 water/ethanol solution. An aqueous solution may be acid or basic. In certain embodiments, the compound is soluble in an alcohol (e.g., methanol, ethanol, denatured ethanol, isopropanol, butanol).

Polymerization Initiators

Polymerization is typically effected through use of a polymerization initiator. A polymerization initiator may be chosen based on the type of monomers being used, the type of initiation (e.g., heat or photoinitiation), and solubility of initiator in a carrier or other excipient. Preferably the present invention does not include a polymerization initiator, more preferably it does not include a polymerization initiator that is activated under ambient or uv light or using a heat source below 160° C., and even more preferably using a heat source below 120° C.

The present invention preferably does not include a free radical initiator, which forms free radicals upon exposure to light or upon heating. Typically, the initiator decomposes upon heating or exposure to a certain wavelength of light to yield two free radicals that initiate the polymerization reaction. The free radical generated from the initiator reacts with an unsaturated functional group (e.g., an alkene, acrylate, or methacrylate functionality) of a monomer thus beginning the chain reaction which results in the formation of the desired fluorinated polymer.

The present invention preferably does not include oxygen tolerant polymerization initiators. Oxygen-tolerant initiators eliminate the need for an oxygen-free or an oxygen-reduced environment for the polymerization reaction to take place. Such oxygen-tolerant initiators allow for the polymerization reaction to take place directly on hair fibers in a normal atmosphere with about 21% oxygen. Exemplary oxygen tolerant polymerization initiators include 4,4'-azobis(4-cyanovaleric acid); 1,1'-azobis(cyclohexanecarbonitrile); 2,2'-azobis(2-methylpropionitrile); 2,2'-azo-bis-isobutyronitrile (AIBN); benzoyl peroxide; 2,2-bis(tert-butylperoxy)butane; 2,5-bis(tert-butylperoxy)-2,5-dimethylhexane; bis[1-(tert-butylperoxy)-1-methyl ethyl]benzene; tert-butyl hydroperoxide; tert-butyl peracetate; tert-butyl peroxide; tert-butyl peroxybenzoate; cumene hydroperoxide; dicumyl peroxide; lauroyl peroxide; peracetic acid; potassium persulfate; 2-hydroxy-2-methyl-phenylpropanone; 2,4,6-trimethylbenzoyl-diphenyl phosphine oxide; 2,4,6-trimethyl benzophenone; oligo(2-hydroxy-2-methyl-1-(4-(1-methylvinyl)phenyl)propanone; and 4-methylbenzophenone.

The present invention preferably does not include an initiator. To effect polymerization typically, the concentration of initiator is approximately 1000-fold, 100-fold, 10-fold, or 5-fold less than the concentration of monomer. To effect polymerization in some cases the initiator is at a concentration of more than about 0.001%. In other cases the initiator is at a concentration of more than about 0.01%. In certain other cases the concentration of initiator is more than about 0.1%. Practice of the present invention preferably avoids employing any of the above mentioned ratios of initiator to monomer and/or avoids employing any of the stated initiator concentrations.

The present invention preferably does not include an initiator that is a free radical thermal initiator. A thermal initiator is designed to work at a temperature ranging from 30° C. to 120° C. The present invention preferably does not include a co-initiator. Co-initiators act to lower the decomposition temperature of the initiator. Exemplary co-initiators include, but are not limited to, aromatic amine (e.g., dimethyl aniline), organic peroxides, decahydroacridine 1,8-dione, etc. Other co-initiators are listed below. The heat may be applied to hair with monomer and initiator applied for about 10 seconds to about 5 minutes. The heat source for initiating polymerization may include, but is not limited to, blow dryers, curling irons, hot curlers, hair irons, hair straighteners, hair crimpers, hot air brushes, and hair dryers.

The present invention preferably does not include thermal initiators, such as, azo compounds, peroxides, peracids, peracetates, persulfates, etc. Exemplary thermal initiators include tert-amyl peroxybenzoate; 4,4'-azobis(4-cyanovaleric acid); 1,1'-azobis(cyclohexanecarbonitrile); 2,2'-azobis(2-methylpropionitrile); benzoyl peroxide; 2,2'-azo-bis-isobutyronitrile (AIBN); benzoyl peroxide; 2,2-bis(tert-butylperoxy)butane; 1,1-bis(tert-butylperoxy)cyclohexane; 2,5-bis(tert-butylperoxy)-2,5-dimethylhexane; 2,5-bis(tert-butylperoxy)-2,5-dimethyl-3-hexyne; bis[1-(tert-butylperoxy)-1-methylethyl]benzene; 1,1-bis(tert-butylperoxy)-3,3,5-trimethylcyclohexane; tert-butyl hydroperoxide; tert-butyl peracetate; tert-butyl peracetic acid; tert-butyl peroxide; tert-butyl peroxybenzoate; tert-butylperoxy isopropyl carbonate; cumene hydroperoxide; cyclohexanone peroxide; dicumyl peroxide; lauroyl peroxide; 2,4-pentanedione peroxide; peracetic acid; and potassium persulfate. Many of the above listed thermal initiators are available from commercial sources such as Sigma-Aldrich. The present invention preferably does not include initiators, such as, 2,2'-azo-bis-isobutyronitrile (AIBN) or benzoyl peroxide (also known as dibenzoyl peroxide). The present invention preferably does not include a combination of thermal initiators or a combination of ammonium persulfate (APS) and N,N,N',N'-tetramethylethylenediamine (TEMED).

The present invention preferably does not include a free radical initiator that is a photoinitiator. Photoinitiators produce reactive free radical species that initiate the polymerzation of monomers upon exposure to light. Photoinitiated polymerizations and photoinitiators are discussed in detail in Rabek, *Mechanisms of Photophysical Processes and Photochemical Reactions in Polymers*, New York: Wiley & Sons, 1987; Fouassier, *Photoinitiation, Photopolymerization, and Photocuring*, Cincinnati, Ohio: Hanser/Gardner; Fisher et al., "Photoinitiated Polymerization of Biomaterials" *Annu. Rev. Mater. Res.* 31:171-81, 2001; incorporated herein by reference. The present invention preferably does not include a photoinitiator designed to produce free radicals at any wavelength of light. The present invention preferably does not include a photoinitiator designed to work using UV light (200-500 nm), long UV rays or short UV rays. The present invention preferably does not include a photoinitiator designed to work using visible light (400-800 nm). The present invention preferably does not include a photoinitiator designed to work using blue light (420-500 nm). The present invention preferably does not include a photoinitiator designed to work using IR light (800-2500 nm). The output of light can be controlled to provide greater control over the polymerization reaction.

The present invention preferably does not include a photoinitiator, such as, a peroxide (e.g., ROOR'), a ketone (e.g., RCOR'), an azo compound (e.g., compounds with a —N═N— group), an acylphosphineoxide, a sulfur-containing compound or a quinone. Exemplary photoinitiators preferably not included in the present invention are acetophenone; anisoin; anthraquinone; anthraquinone-2-sulfonic acid, sodium salt monohydrate; (benzene) tricarbonylchromium; 4-(boc-aminomethyl)phenyl isothiocyanate; benzin; benzoin; benzoin ethyl ether; benzoin isobutyl ether; benzoin methyl ether; benzoic acid; benzophenone; benzyl dimethyl ketal; benzophenone/1-hydroxycyclohexyl phenyl ketone; 3,3',4,4'-benzophenonetetracarboxylic dianhydride; 4-benzoylbiphenyl; 2-benzyl-2-(dimethylamino)-4'-morpholinobutyrophenone; 4,4'-bis(diethylamino)benzophenone; 4,4'-bis(dimethylamino)benzophenone; Michler's ketone; camphorquinone; 2-chlorothioxanthen-9-one; 5-dibenzosuberenone; (cumene)cyclopentadienyliron(II) hexafluorophosphate; dibenzosuberenone; 2,2-diethoxyacetophenone; 4,4'-dihydroxybenzophenone; 2,2-dimethoxy-2-phenylacetophenone; 4-(dimethylamino)benzophenone; 4,4'-dimethylbenzil; 2,5-dimethylbenzophenone; 3,4-dimethylbenzophenone; diphenyl(2,4,6-trimethylbenzoyl)phosphine oxide; 2-hydroxy-2-methylpropiophenone; 4'-ethoxyacetophenone; 2-ethylanthraquinone; ferrocene; 3'-hydroxyacetophenone; 4'-hydroxyacetophenone; 3-hydroxybenzophenone; 4-hydroxybenzophenone; 1-hydroxycyclohexyl phenyl ketone; 2-hydroxy-2-methylpropiophenone; 2-methylbenzophenone; 3-methylbenzophenone; methybenzoylformate; 2-methyl-4'-(methylthio)-2-morpholinopropiophenone; 9,10-phenanthrenequinone; 4'-phenoxyacetophenone; thioxanthen-9-one; triarylsulfonium hexafluoroantimonate salts; triarylsulfonium hexafluorophosphate salts; 3-mercapto-1-propanol; 11-mercapto-1-undecanol; 1-mercapto-2-propanol; 3-mercapto-2-butanol; hydrogen peroxide; benzoyl peroxide; 4,4'-dimethoxybenzoin; 2,2-dimethoxy-2-phenylacetophenone; dibenzoyl disulphides; diphenyldithiocarbonate; 2,2'-azobisisobutyronitrile (AIBN); camphorquinone (CQ); eosin; dimethylaminobenzoate (DMAB); dimethoxy-2-phenyl-acetophenone (DMPA); Quanta-cure ITX photosensitizer (Biddle Sawyer); Irgacure 907 (Ciba Geigy); Irgacure 651 (Ciba Geigy); Darocur 2959 (Ciba Geigy); ethyl-4-N,N-dimethylaminobenzoate (4EDMAB); 1-[-(4-benzoylphenylsulfanyl)phenyl]-2-methyl-2-(4-methylphenylsulfonyl) propan-1-one; 1-hydroxy-cyclohexyl-phenyl-ketone; 2,4,6-trimethylbenzoyldiphenylphosphine oxide; diphenyl(2,4,6-trimethylbenzoyl)phosphine; 2-ethylhexyl-4-dimethylaminobenzoate; 2-hydroxy-2-methyl-1-phenyl-1-propanone; 65% (oligo[2-hydroxy-2-methyl-1-[4-(1-methylvinyl)phenyl]propanone] and 35% propoxylated glyceryl triacrylate; benzil dimethyl ketal; benzophenone; blend of benzophenone and α-hydroxy-cyclohexyl-phenyl-ketone; blend of Esacure KIP150 and Esacure TZT; blend of Esacure KIP150 and Esacure TZT; blend of Esacure KIP150 and TPGDA; blend of phosphine oxide, Esacure KIP150 and Esacure TZT; difunctional α-hydroxy ketone; ethyl 4-(dimethylamino)benzoate; isopropyl thioxanthone; 2-hydroxy-2-methyl-phenylpropanone; 2,4,6,-trimethylbenzoyldiphenyl phosphine oxide; 2,4,6-trimethyl benzophenone; liquid blend of 4-methylbenzophenone and benzophenone; oligo(2-hydroxy-2 methyl-1-(4 (1-methylvinyl)phenyl)propanone; oligo(2-hydroxy-2-methyl-1-4 (1-methylvinyl)phenyl propanone and 2-hydroxy-2-methyl- 1-phenyl-1-propanone (monomeric); oligo (2-hydroxy-2-methyl-1-4 (1-methylvinyl)phenyl propanone and 2-hydroxy-2-methyl-1-phenyl-1-propanone (polymeric); 4-methylbenzophenone; trimethylbenzophenone and methylbenzophenone; and water emulsion of 2,4,6-trimethylbenzoylphosphine oxide, alpha hydroxyketone, trimethylbenzophenone, 4-methyl benzophenone, acetophenone; diphenyl(2,4,6-trimethylbenzoyl)phosphine oxide; 4,4'-dimethoxybenzoin; anthraquinone; anthraquinone-2-sulfonic acid; benzene-chromium(0) tricarbonyl; 4-(boc-aminomethyl)phenyl isothiocyanate; benzil; benzoin; benzoin ethyl ether; benzoin isobutyl ether; benzoin methyl ether; benzophenone; benzoic acid; benzophenone/1-hydroxycyclohexyl phenyl ketone, 50/50 blend; benzophenone-3,3',4,4'-tetracarboxylic dianhydride; 4-benzoylbiphenyl; 2-benzyl-2-(dimethylamino)-4'-morpholinobutyrophenone; 4,4'-bis(diethylamino)benzophenone; Michler's ketone; (±)-camphorquinone; 2-chlorothioxanthen-9-one; 5-dibenzosuberenone; 2,2-diethoxyacetophenone; 4,4'-dihydroxybenzophenone; 2,2-dimethoxy-2-phenylacetophenone; 4-(dimethylamino)benzophenone; 4,4'-dimethylbenzil; 3,4-dimethylbenzophenone; diphenyl(2,4,6-trimethylbenzoyl)phosphine oxide/2-hydroxy methylpropiophenone; 4'-ethoxyacetophenone; 2-ethylanthraquinone; ferrocene; 3'-hydroxyacetophenone; 4'-hydroxyacetophenone; 3-hydroxybenzophenone; 4-hydroxybenzophenone; 1-hydroxycyclohexyl phenyl ketone; 2-hydroxy-2-methylpropiophenone; 2-methylbenzophenone; 3-methylbenzophenone; methyl benzoylformate; 2-methyl-4'-(methylthio)-2-morpholinopropiophenone; 9,10-phenanthrenequinone; 4'-phenoxyacetophenone; thioxanthen-9-one; triarylsulfonium hexafluorophosphate salts; 3-mercapto-1-propanol; 11-mercapto-1-undecanol; 1-mercapto-2-propanol; and 3-mercapto-2-butanol. The present invention preferably does not include a free radical initiator is selected from the group consisting of benzophenone, benzyl dimethyl ketal, 2-hydroxy-2-methyl-phenylpropanone; 2,4,6-trimethylbenzoyldiphenyl phosphine oxide; 2,4,6-trimethyl benzophenone; oligo(2-hydroxy-2-methyl-1-(4-(1-methylvinyl)phenyl)propanone and 4-methylbenzophenone. The present invention preferably does not include a photoinitiator, such as, dimethoxy-2-phenyl-acetophenone (DMPA), a titanocene or a combination of photoinitiators.

The present invention preferably does not include an initiator of a cationic or anionic polymerization process. The present invention preferably does not include an initiator that is a photoinitiator of a cationic polymerization process, such as, titanium tetrachloride, vanadium tetrachloride, bis(cyclopentadienyl)titanium dichloride, ferrocene, cyclopentadienyl manganese tricarbonyl, manganese decacarbonyl, diazonium salts, diaryliodonium salts (e.g., 3,3'-dinitrodiphenyliodonium hexafluoroarsenate, diphenyliodonium fluoroborate, 4-methoxydiphenyliodonium fluoroborate) and triarylsulfonium salts. The present invention preferably does not include a free radical/cationic photoinitiator to polymerize the monomers in situ on hair.

The present invention preferably does not include an anionic polymerization initiator. The anionic polymerization initiators preferably not included in the present invention may be molecular compounds, oligomers, dendrimers, and polymers which comprise at least one nucleophilic function, for example, $R_2N^-$, $NH_2^-$, $Ph_3C^-$, $R_3C^-$, $PhNH^-$, pyridine, $ArS^-$, $R-C\equiv C^-$, $RS^-$, $SH^-$, $RO^-$, $R_2NH$, $ArO^-$, $N_3^-$, $OH^-$, $ArNH_2$, $NH_3$, $I^-$, $Br^-$, $Cl^-$, $RCOO^-$, $SCN^-$, $ROH$, $RSH$, $NCO^-$, $CN^-$, $NO_3^-$, $ClO_4^-$ and $H_2O$, wherein Ph is a phenyl group, Ar is chosen from aryl groups, and R is chosen from $C_1$-$C_{10}$ alkyl groups.

Cosmetic Hair Care Compositions

The present invention provides cosmetic hair care compositions comprising an active hair care ingredient as described above, and a cosmetically acceptable excipient. Cosmetically acceptable excipients used in the hair care industry can be broken down into several categories. Components from a category may be included or excluded from the final hair care composition depending on the use of the final composition (e.g., hair spray, conditioner, shampoo). The categories of excipients include: (1) preservatives/antioxidants/chelating agents; (2) sunscreen agents; (3) vitamins; (4) dyes/hair coloring agents; (4) proteins/amino acids; (5) plant extracts; (6) humectants; (7) fragrances/perfumes; (8) oils/emollients/lubricants/butters; (9) penetrants; (10) thickeners/viscosity modifiers; (11) polymers/resins/hair fixatives/film formers; (12) surfactants/detergents/emulsifiers/opacifying agents; (13) volatiles/propellants/solvents/carriers; (14) liquid vehicles/solvents/carriers; (15) salts; (16) pH adjusting agents/buffers/neutralizing agents; (17) hair conditioning agents; (18) anti-static agents/anti-frizz agents; (19) antidandruff agents; (20) hair waving/straightening agents; and (21) absorbents.

In certain embodiments, the cosmetic hair care composition is a spray. The spray typically includes the active hair care ingredient and a carrier or propellant. In certain embodiments, the carrier is a water and alcohol mixture. In certain embodiments, the spray composition also optionally includes a preservative, antioxidant, sunscreen agent, vitamin, protein, peptide, plant extract, humectant, oil, emollient, lubricant, thickener, hair conditioning agent, polymer, or surfactant. In certain embodiments, the composition includes an oil. In certain embodiments, the composition includes a polymer. In certain embodiments, the composition includes a humectant. In certain embodiments, the composition includes a fragrance. In certain particular embodiments, the composition comprises water, an alcohol, an oil, fragrance, and an active hair care ingredient. In certain particular embodiments, the composition comprises water, an alcohol, an oil, a polymer, fragrance, and an active hair care ingredient. In certain particular embodiments, the composition comprises water, an alcohol, an anti-static agent, fragrance, and an active hair care ingredient. In certain particular embodiments, the composition comprises water, an alcohol, a hair-conditioning agent, fragrance, and an active hair care ingredient. In certain particular embodiments, the composition comprises water, an alcohol, a surfactant, fragrance, and an active hair care ingredient. In certain particular embodiments, the composition comprises water, an alcohol, an emollient, fragrance, and an active hair care ingredient. Hair spray compositions are dispensed from containers that aerosol dispensers or pump spray dispensers. Such dispensers are known in the art and are commercially available from a variety of manufacturers, including American National Can Corp. and Continental Can Corp.

In certain embodiments, when the hair spray composition is dispensed from a pressurized aerosol container, a propellant is used to force the composition out of the container. Suitable propellants are described herein. In certain embodiments, the propellant is a liquifiable gas. In certain embodiments, the propellant is a halogenated propellant. In other embodiments, the composition does not contain any fluorinated or chlorinated propellants. Generally, the amount of propellant in the composition is from about 10% to about 60% by weight. In certain embodiments, the amount of propellant in the composition ranges from about 15% to about 50% by weight. In certain embodiments, the propellant is separated from the hair spray composition as in a two compartment container. Other suitable aerosol dispensers are those characterized by the propellant being compressed air which can be filled into the dispenser using a pump or equivalent device prior to use. Such dispensers are described in U.S. Pat. Nos. 4,077,441 and 4,850,577, both of which are incorporated by reference herein, and in U.S. patent application, U.S. Ser. No. 07/839,648, filed Feb. 21, 1992, also incorporated by reference herein. Conventional non-aerosol pump spray dispensers, i.e., atomizers, may also be used to apply the invention hair spray compositions.

In certain embodiments, the cosmetic hair care composition is a cream. The inventive cream typically includes the active hair care ingredient, a carrier, an oil, a hair conditioning agent, and a thickening agent. In certain embodiments, the cream also includes a fragrance. In certain embodiments, the cream also includes a plant extract. In certain embodiments, the cream also includes a surfactant. In certain embodiments, the cream also include a polymer. The inventive cream may be packaged in a tube, tub, bottle, or other suitable container.

Moisture Resistance

Moisture on hair and its penetration into the hair can disturb the arrangement of hair proteins, resulting in cosmetically undesired changes, such as, an increase of frizz. The present invention provides hair, in particular hair on or from the scalp, with beneficial moisture resistance properties. Moisture resistance in the present invention refers to the hysteresis of water sorption/desorption when measured by Dynamic Vapor Sorption (DVS). In DVS a sample is placed on a microbalance exposed to a continuous flow of air with predetermined and constant relative humidity. As the humid air passes over the sample, a zone of constant moisture concentration is created around it. This zone allows the rapid establishment of water vapor sorption or desorption equilibrium by maximizing mass transport of water vapor into and out of the sample.

Mass changes in the sample (e.g., a swatch of hair) due to water vapor sorption/desorption can be measured between different levels of relative humidity at a particular temperature. The change in mass can be plotted as a function of the relative humidity, which provides information about the nature of water vapor sorption phase (absorption and/or adsorption) when humidity is increased, or, conversely, the nature of desorption of water, when humidity is decreased. The difference in changes in mass at any particular value for relative humidity in the sorption and desorption phases is known as the hysteresis and can be used as a measure to evaluate the ability of a hair treatment to resist or control moisture on and in hair. As described below, the invention affords reduced hysteresis especially over relative humidity values range of 30-80% RH.

In the context of the present invention, moisture resistance is measured according to DVS Protocol I.

DVS Protocol I 1. 1.50 g of bleached hair tress is dampened with 0.30 mL de-ionized water, optionally via pipet, and lightly combed through to remove any tangles.
2. Apply composition to the hair tress according to the following amounts: for a serum (0.10 g to 0.12 g), for a cream/lotion/mousse (0.20 g to 0.25 g), and for a spray (0.35 g to 0.40 g) and is distributed evenly and combed through the hair. Preferably the weight ratio of formulation to hair should be approximately 0.073 for serums, 0.15 for a cream/lotion/mousse and 0.25 for a spray.
3. Styling consists of 10 passes with a hair brush and blow drier set to high, approximately 50-120° C.
4. After styling, the hair is cut and sections from the middle of each tress (approximately 300 mg) are analyzed via DVS.
5. DVS conditions are as follows. Unless otherwise stated the temperature employed is 25° C. Sorption phase: Start at 30% RH and increase up to 90% RH, each step increasing RH by 10%. Desorption phase: Start at 90% RH and decrease down to 0% RH, each step decreasing RH by 10%. At each RH condition, the sample is maintained for 4 hours, and the step up or down to the next RH level is programmed to occur over 20 min period.

Monitoring the hysteresis values from such a DVS experiment on hair samples allows assessment of the ability of a hair treatment to resist or control moisture.

The present invention affords superior moisture resistance compared to either (1) a control treatment using water and (2) a leading silicone product, such as Kerastase Olexo Relax Serum®, which in fact increased the hysteresis compared to water. Preferably, use of the invention on a hair tress as described above affords a 4% reduction in the average hysteresis values compared to control (water-treated) hair over the relative humidity range of 30-80% when examined by the DVS protocol described above. More preferably, use of the invention on a hair tress as described above affords more than a 10% reduction and still more preferably more than a 20% reduction, in the average hysteresis values compared to control (water treated) hair over the relative humidity range of 30-80% when examined by the DVS protocol described above. Even more preferably, the invention affords a 50% or more, or even an 80% or more, reduction in the average hysteresis values compared to control (water-treated) hair over the relative humidity values range of 30-80% RH when determined by the DVS protocol described above.

Weightlessness

Those who use hair care products desire the beneficial effects described above. However, such users do not want the feeling of residue/product in or on their hair. A composition that maintains performance, but which does so with less residual weight or "feel" in the hair is, therefore, preferred.

The compositions of the present invention, while maintaining product performance, beneficially lose no less than 25% of their weight, preferably 50% of their weight, more preferably no less than 70% of their weight, still more preferably no less than 80% weight, and still more preferably no less than 90%, and most preferably 95% or higher of their weight after heating at 55° C. and 25% RH for 20 minutes (for spray formulations) and 30 minutes (cream/lotion/serum/mousse) formulations according to the "Weightlessness Test I."

Weightless Test I

Composition is dispensed into an uncovered container and spread out evenly. For instance, the container is a round container with a diameter of 9 cm and a lip measuring 0.5 cm.
1. The containers are labeled and then weighed immediately before and after dosing with 3 g of formulation.
2. Compositions are left to equilibrate at ambient conditions (25° C., 30% RH) for 5 minutes before placing into the oven.
3. The container is placed into an oven controlled at 55° C. and 25% RH.
4. Each dish is removed and its mass recorded at 20 minutes for spray compositions and 30 minutes for cream/lotion/serum/mousse compositions.

The compositions for treating hair according to the invention on average leave at least 25% less residue upon dry-down when following package instructions for amounts used for Kerastase Oleo Relax Serum®, John Frieda Frizz Ease®, Biosilk Silk Therapy®, Redken Smooth Down Heat Glide®, Nexxus Sleek Memory Straightening Smooth Spray®, Barex Re-define Cràme®, Fekkai Glossing Cream® and Bedhead Curls Rock®. It is believed that one reason for the "weightlessness" benefits of the inventive formulations is that they do not require, and preferably do not include, silicone compounds at levels found in the above identified hair care products.

Dirt Resistance

Many materials are used to control or reduce moisture penetration into hair fibers. However, the majority of these materials are oil-based or silicone-based. The resulting effect is modest moisture resistance combined with a heavy residue feel which attracts grease and particulates. It is desirable in the art to create a composition that will control or reduce moisture penetration into hair fibers while leaving the hair feeling lightweight, non-greasy, and minimizing attraction of dirt/particulates.

The attraction of dirt and particles to the hair leaves the hair limper, heavier, and duller throughout the day. The ability to resist environmental pollutants gives the hair longer lasting style and shine. Accordingly, the ability of the present inventive hair care compositions to resist dirt accumulation was examined and compared to Kerastase Oleo Relax Serum®. Corn starch was selected as simulated dirt. USP corn starch is uniformly-white and can associate with hair, providing excellent contrast on black hair, thereby allowing for a quantifiable Gray-scale measurement via digital photography. Remaining corn starch was also assayed by gravimetric analysis.

Starch Resistance (Gravimetric)

The inventive hair care compositions when tested on hair as described below should afford gain in weight of no more than 15% by weight, preferably no more than 10% by weight, more preferably no more than 7% weight, and most preferably no more than 5% by weight when subjected to the Starch Test I.

Starch Test I 1. 1.50 g of virgin dark brown hair tress is dampened with 0.30 mL of water.
2. Apply composition to the hair tress according to the following amounts: for a serum (0.10 g to 0.12 g), for a cream/lotion/mousse (0.20 g to 0.25 g), and for a spray (0.35 g to 0.40 g) and is distributed evenly and combed through the hair. Preferably the weight ratio of formulation to hair should be approximately 0.073 for serums, 0.15 for a cream/lotion/mousse and 0.25 for a spray.
3. The hair was styled with a hair brush and blow drier on high speed and high temperature, approximately at 50-120° C. for 30 seconds.
4. The tress is saturated in a bath of corn starch, for instance, in about 2 grams of corn starch, USP.
5. The tress is removed from the corn starch bath and shaken by hand until all loose corn starch is removed, for instance, for 10 seconds.
6. The tress is weighed and the new mass is recorded.

Starch Resistance (Gray Value)

The inventive hair care compositions when tested on hair as described below should display equal Gray values to those generated by a similar sample treated with water, preferably the composition-treated hair sample should display Gray values 5% less than those generated from a similar sample treated with water, more preferably the composition-treated hair sample should display Gray values 10% less than those generated from a similar sample treated with water, and most preferably the composition-treated hair sample should display Gray values of at least 15% less than those generated from a similar sample treated with water when subjected to Starch Test II.

Starch Test II 1. 1.50 g of virgin dark brown hair tress is dampened with 0.30 mL of water.
2. Apply composition to the hair tress according to the following amounts: for a serum (0.10 g to 0.12 g), for a cream/lotion/mousse (0.20 g to 0.25 g), and for a spray (0.35 g to 0.40 g) and is distributed evenly and combed through the hair. Preferably the weight ratio of formulation to hair should be approximately 0.073 for serums, 0.15 for a cream/lotion/mousse and 0.25 for a spray 3. The hair was styled with a round brush and blow drier on high speed and high temperature, approximately 50-120° C. for 30 seconds.
4. The tress is saturated in a bath of corn starch, for instance, in about 2 grams of corn starch, USP.
5. The tress is removed from the corn starch bath and shaken by hand until all loose corn starch is removed, for instance, for 10 seconds.
6. Samples were taped hanging against a black background
7. Photographs were taken from a distance that allowed the entirety of the tresses to be captured, approximately 3 feet away.
8. Images were analyzed using Image J software (Wayne Rasband, National Institutes of Health, USA). Photographs were converted to Grayscale and a box was drawn wide enough to encompass all tresses. The box height was adjusted so as to include only the middle third of the tresses, and the "Plot Profile" feature was used to collect gray value data, which was imported into Microsoft Excel.

The present invention may be used on any animal with hair. The system is particularly useful for treating human hair. However, the hair or fur of other mammals may also be treated. For example, the hair or fur of domesticated animals such as dogs and cats may be treated using the inventive system. In addition, the hair or fur of test animals such as rodents (e.g., mouse, rat, rabbit, guinea pig, etc.) or primates may also be treated. In certain embodiments, hair samples from a human (e.g., hair clippings) or other animals are tested with the present invention. Hair or fur samples treated with the present invention are considered to be within the scope of the invention. These hair or fur samples comprise compound on the hair or fur. In certain embodiments, the hair is human hair. In other embodiments, the hair is non-human hair. In certain embodiments, the hair or fur is dog or cat hair or fur. In other embodiments, the hair is rat, mouse, guinea pig, rabbit, gerbil, or primate hair. The hair treatment system of the present invention can also be used to treat hair contained in wigs, toupees, and hairpieces.

These and other aspects of the present invention will be further appreciated upon consideration of the following Examples, which are intended to illustrate certain particular embodiments of the invention but are not intended to limit its scope, as defined by the claims.

EXAMPLES

Example 1

Testing of Treated Hair

Tests as described herein may be used to test shine/luster, break strength, and hair fiber thickness.

In this example, the measure of the hair's shine/luster is proposed. After applying a composition and curling and brushing a hair sample, the hair would be wound around a cylinder and placed under a lamp that mimics sunlight. The width of the cone of luster will be measure and compared with that of a commercial product.

In this example, the measure of the hair's break strength is proposed. Single hair fibers (treated and untreated) can be attached to an Instron which will pull at one end of the fiber, breaking the fiber at a certain force.

In this example, the measure of the hair fiber thickness is proposed. Cross sections of hair fibers (treated and untreated) can be examined and measured by microscopy.

In this example, the humidity resistance of the treated hair is proposed. This property can be measured by placing the styled hair tress in an atmosphere of high humidity.

In this example, the feel is proposed. The parameters of feel can be assessed for a given material on the hair fiber. Several parameters such as tack, slip, stiffness, smoothness, grease, and strength can be evaluated by a blind test of experts.

Example 2

Styling Spray

Below are included various hair care compositions of the exemplary halogenated monomers. The halogenated monomers may be, for example, 1,1,1,3,3,3-hexafluoroisopropyl 2-fluoroacrylate; 1,1,1,3,3,3-hexafluoroisopropyl 2-fluoromethacrylate; 1,1,1,3,3,3-hexafluoroisopropyl acrylate; 1,1,1,3,3,3-hexafluoroisopropyl methacrylate; 2,2,3,3,4,4,5,5-octafluoro-1,6-hexyl dimethacrylate; 2,2,3,3,4,4,5,5-octafluoro-1,6-hexyl diacrylate; methyl pentafluoromethacrylate; methyl pentafluoroacrylate; methyl trifluoroacrylate; methyl trifluoromethacrylate; heptafluoroisopropyl acrylate; heptafluoroisopropyl methacrylate; hexafluoroisopropyl crotonate; hexafluoro-2-methylisopropyl acrylate; hexafluoro-2-methylisopropyl methacrylate; 1,1,1,3,3,3-hexafluoroisopropyl methacrylate; 1,1,1,3,3,3-hexafluoroisopropyl acrylate; 1,1,1,3,3,3-hexafluoroisopropyl dimethacrylate; 1,1,1,3,3,3-hexafluoroisopropyl diacrylate; pentafluorobenzyl acrylate; pentafluorobenzyl methacrylate; tert-butyl-2-(trifluoromethyl)acrylate; tert-butyl-2-(trifluoromethyl) methacrylate; 1H,1H,1H-eicosafluoroundecyl acrylate; 1H,1H,1H-eicosafluoroundecyl methacrylate; 2,2,3,3,4,4,5,5-octafluoro-1,6-hexyldiacrylate; 2,2,3,3,4,4,5,5-octafluoro-1,6-hexyldimethacrylate; 2,2,3,3,4,4,5,5-octafluoropentyl methacrylate; 2,2,3,3,4,4,5,5-octafluoropentyl acrylate; 2,2,3,3,4,4-hexafluoro-1,5-pentyl diacrylate; 2,2,3,3,4,4-hexafluoro-1,5-pentyl dimethacrylate; 2,3-dichloro-1-propyl acrylate; 2,3-dichloro-1-propyl methacrylate; 1-3-dichloro-2-propyl acrylate; 1-3-dichloro-2-propyl methacrylate; 2,2,2-trichloroethyl acrylate; 2,2,2-trichloroethyl methacrylate; 2-chloroethyl acrylate; 2-chloroethyl methacrylate; 2,2,2-tribromoethyl acrylate; 2,2,2-tribromoethyl methacrylate; 2,2,2-tribromoethyl methacrylate; and 2,2,2-tribromoethyl acrylate or any of the other halogenated monomer of the present invention as described above. As would be appreciated by one of skill in the art, these formulations may be used to deliver other compounds described herein such as other methacrylates, acrylates, alkenes, halogenated compounds, etc. An exemplary styling spray containing a halogenated monomer may include:

| | |
|---|---|
| Water | 45-51% w/w |
| Alcohol (e.g., ethanol) | 40-55% w/w |
| PEG-40 Hydrogenated Castor Oil | 0.1-5% w/w |
| Fragrance | 0.1-1.5% w/w |
| Halogenated Monomer | 0.1-10% w/w |

Example 3

Styling Spray

An exemplary styling spray containing a halogenated monomer may include:

| | |
|---|---|
| Water | 45-51% w/w |
| Alcohol (e.g., ethanol) | 40-55% w/w |
| VP/Vinyl Caprolactam/DMAPA Acrylates Copolymer | 0.01-2% w/w |
| PEG-40 Hydrogenated Castor Oil | 0.01-5% w/w |
| Fragrance | 0.1-1.5% w/w |
| Halogenated Monomer | 0.1-10% w/w |

The halogenated monomer is as described in Example 2 above.

Example 4

Styling Spray

Another exemplary styling spray may include:

| | |
|---|---|
| Water | 45-51% w/w |
| Alcohol (e.g., ethanol) | 40-55% w/w |
| PVP/VA | 0.01-2.5% w/w |
| PEG-40 Hydrogenated Castor Oil | 0.1-5% w/w |
| Fragrance | 0.1-1.5% w/w |
| Halogenated Monomer | 0.1-10% w/w |

The halogenated monomer is as described in Example 2 above.

Example 5

Styling Spray

An exemplary styling spray containing a halogenated monomer may include:

| | |
|---|---|
| Water | 45-51% w/w |
| Alcohol (e.g., ethanol) | 40-55% w/w |
| Cetrimonium chloride | 0.01-2.5% w/w |
| PPG-2 myristyl ether propionate | 0.01-2.5% w/w |
| PEG-40 hydrogenated castor oil | 0.01-5% w/w |
| Fragrance | 0.1-1.5% w/w |
| Halogenated Monomer | 0.1-10% w/w |

The halogenated monomer is as described in Example 2 above.

Example 6

Styling Spray

An other exemplary styling spray containing a halogenated monomer may include:

| | |
|---|---|
| Water | 45.0-51.0% w/w |
| Alcohol (e.g., ethanol) | 40.0-55.0% w/w |
| Glycereth-7 | 0.1-2.5% w/w |
| PEG-40 Hydrogenated Castor Oil | 0.1-5.0% w/w |
| Fragrance | 0.1-1.5% w/w |
| Halogenated Monomer | 0.1-10% w/w. |

The halogenated monomer is as described in Example 2 above.

Example 7

Styling Cream

An exemplary styling cream containing a halogenated monomer may include:

| | |
|---|---|
| Water | 75-97% w/w |
| Polysorbate 80 | 0.1-2.0% w/w |
| Isohexadecane | 0.1-2.0% w/w |
| Acrylamide/Sodium Acryloyldimethyltaurate copolymer | 0.1-1.0% w/w |
| PPG-2 Myristyl Ether Propionate | 0.1-3% w/w |
| Phenoxyethanol | 0.1-1.0% w/w |
| Methylparaben | 0.1-0.5% w/w |
| Propylparaben | 0.1-0.5% w/w |
| Fragrance | 0.1-1.5% w/w |
| Halogenated Monomer | 0.1-10% w/w |

The halogenated monomer is as described in Example 2 above.

Example 8

Styling Cream

An exemplary styling cream containing halogenated monomer may include:

| | |
|---|---|
| Water | 75-97% w/w |
| Polysorbate 20 | 0.1-1.0% w/w |
| Polyacrylate-13 | 0.5-3.5% w/w |
| Polyisobutene | 0.5-3.5% w/w |
| Ethylhexyl Stearate | 0.1-3% w/w |
| Phenoxyethanol | 0.3-1.5% w/w |
| Caprylyl glycol | 0.1-1.0% w/w |
| Sorbic acid | 0.1-0.5% w/w |
| Cetyl Alcohol | 0.25-1.5% w/w |
| Fragrance | 0.1-1.5% w/w |
| Halogenated Monomer | 0.1-10% w/w |

The halogenated monomer is as described in Example 2 above.

Example 9

Styling Cream

An exemplary styling cream containing a halogenated monomer may include:

| | |
|---|---|
| Water | 75-97% w/w |
| Cetearyl Alcohol | 1.5-5% w/w |
| Glyceryl Stearate | 0.5-3% w/w |
| Ceteareth-20 | 0.5-3% w/w |
| PPG-2 Myristyl Ether Propionate | 0.1-3% w/w |
| Phenoxyethanol | 0.1-1.5% w/w |
| Fragrance | 0.1-1.5% w/w |
| Halogenated Monomer | 0.1-10% w/w |

The halogenated monomer is as described in Example 2 above.

Example 10

Styling Spray

An exemplary styling spray containing a halogenated monomer may include:

| | |
|---|---|
| Water | 45-94% w/w |
| Alcohol (e.g., ethanol) | 5-45% w/w |
| Stearyl alcohol | 0.5-3% w/w |
| Laureth-23 | 0.1-2% w/w |
| Laureth-4 | 0.1-2% w/w |
| PEG-40 Hydrogenated Castor Oil | 0.1-2% w/w |
| Fragrance | 0.1-1.5% w/w |
| Halogenated Monomer | 0.1-10% w/w |

The halogenated monomer is as described in Example 2 above.

Example 11

Styling Cream

An exemplary styling cream containing a halogenated monomer may include:

| | |
|---|---|
| Water | 72-97% w/w |
| Behenyl alcohol | 1.5-5% w/w |
| Ceteareth-20 | 0.5-5% w/w |
| Ceteth-10 | 0.5-5% w/w |
| PEG-40 Stearate | 0.25-1% w/w |
| Hydroxypropyltrimonium Hydrolyzed Corn Starch | 0.25-1.5% w/w |
| PPG-3 Benzyl Ether Myristate | 0.1-1% w/w |
| Carbomer | 0.01-0.5% w/w |
| Triethanolamine | 0.01-0.8% w/w |
| Fragrance | 0.1-1.5% w/w |
| Halogenated Monomer | 0.1-10% w/w |

The halogenated monomer is as described in Example 2 above.

Example 12

Styling Cream

An exemplary styling cream containing a halogenated monomer may include:

| | |
|---|---|
| Water | 75-97% w/w |
| Cetearyl alcohol | 1.5-5% w/w |
| Ceteareth-20 | 0.5-5% w/w |
| Ceteth-10 | 0.5-5% w/w |
| Behentrimonium Chloride | 0.1-2.5% w/w |
| PPG-2 Myristyl Propionate | 0.25-3% w/w |
| Carbomer | 0.01-.5% w/w |
| Triethanolamine | 0.01-0.8% w/w |
| Fragrance | 0.1-1.5% w/w |
| Halogenated Monomer | 0.1-10% w/w |

The halogenated monomer is as described in Example 2 above.

Example 13

Styling Cream

Another formulation of styling cream containing a halogenated monomer may include:

| | |
|---|---|
| Water | 75-97% w/w |
| Cetearyl alcohol | 1.5-5.0% w/w |
| Ceteareth-20 | 0.5-5.0% w/w |
| Ceteth-10 | 0.5-5.0% w/w |
| VP/Acrylates/Lauryl Methacrylate Copolymer | 0.01-2.5% w/w |
| PPG-2 Myristyl Propionate | 0.25-3.0% w/w |
| Carbomer | 0.01-0.5% w/w |
| Triethanolamine | 0.01-0.9% w/w |
| Fragrance | 0.1-1.5% w/w |
| Halogenated Monomer | 0.1-10% w/w |

The halogenated monomer is as described in Example 2 above.

Example 14

Styling Cream

Another exemplary formulation of styling cream containing a halogenated monomer may include:

| | |
|---|---|
| Water | 75-97% w/w |
| Cetearyl alcohol | 1.5-5% w/w |
| Ceteareth-20 | 0.5-5% w/w |
| Ceteth-10 | 0.5-5% w/w |
| Polyquaternium-28 | 0.5-10% w/w |
| PPG-2 Myristyl Propionate | 0.25-3% w/w |
| Sodium Polyactylate | 0.01-0.5% w/w |
| Fragrance | 0.1-1.5% w/w |
| Halogenated Monomer | 0.1-10% w/w |

The halogenated monomer is as described in Example 2 above.

Example 15

Styling Cream

Another exemplary formulation of styling cream containing a halogenated monomer may include:

| | |
|---|---|
| Water | 75-97% w/w |
| Cetearyl Alcohol | 2-5% w/w |
| Polysorbate 80 | 1-4% w/w |
| PEG-4M | 0.25-2% w/w |
| Fragrance | 0.1-1.5% w/w |
| Halogenated Monomer | 0.1-10% w/w |

The halogenated monomer is as described in Example 2 above.

Example 16

Styling Cream

An exemplary styling cream containing a halogenated monomer may include:

| | |
|---|---|
| Water | 75-97% w/w |
| Cearyl Alcohol | 1.5-5% w/w |
| Steareth-21 | 0.5-5% w/w |
| Steareth-20 | 0.5-5% w/w |
| VP/Acrylates/Lauryl Methacrylate Copolymer | 0.01-2.5% w/w |
| PPG-2 Myristyl Propionate | 0.25-3% w/w |
| Carbomer | 0.01-0.5% w/w |
| Triethanolamine | 0.01-0.8% w/w |
| Fragrance | 0.1-1.5% w/w |
| Halogenated Monomer | 0.1-10% w/w |

The halogenated monomer is as described in Example 2 above.

Example 17

Styling Spray

An exemplary styling spray containing a halogenated monomer may include:

| Ingredients | % w/w |
|---|---|
| Water | q.s. |
| Alcohol (e.g. ethanol) | 0.00-55.00 |
| VP/Vinyl Caprolactam/DMAPA Acrylates Copolymer | 0.00-15.00 |
| VP/Acrylates/Lauryl Methacrylate Copolymer | 0.00-15.00 |
| C10-40 Isoalkylamidopropyl Ethyldimonium Ethosulfate | 0.00-2.00 |
| Cosmetic Fluid CF-76 or CF-61 | 0.00-99.00 |
| Cetrimonium chloride | 0.00-0.50 |
| Oleic Acid | 0.00-2.00 |
| Stearyl Alcohol | 0.00-3.00 |
| Glycereth-7 | 0.00-4.00 |
| Laureth-23 | 0.00-6.00 |
| Laureth-4 | 0.00-6.00 |
| Polysorbate 80 | 0.00-6.00 |
| Sorbitan Oleate | 0.00-4.00 |
| PEG-40 Hydrogenated Castor Oil | 0.00-6.00 |
| Fragrance | 0.00-4.00 |
| Halogenated Monomer | 0.10-20.00 |

The halogenated monomer is as described in Example 2 above.

Example 18

Styling Spray Gel

An exemplary styling spray gel containing a halogenated monomer may include:

| Ingredients | % w/w |
|---|---|
| Water | q.s. |
| Alcohol (e.g. ethanol) | 0.00-55.00 |
| PVP/VA | 0.00-15.00 |
| Glycerin | 0.00-10.00 |
| Glyceryl Polyacrylate | 0.00-2.00 |
| Oleic Acid | 0.00-3.00 |
| Polyquaternium-28 | 0.00-1.00 |
| Acrylic Acid/VP Crosspolymer | 0.00-1.00 |
| Aminomethyl Propanol | 0.00-0.75 |
| Octyldodeceth-20 | 0.00-6.00 |
| PEG-40 Hydrogenated Castor Oil | 0.00-6.00 |
| Preservative | 0.00-2.00 |
| Fragrance | 0.00-4.00 |
| Halogenated Monomer | 0.10-20.00 |

The halogenated monomer is as described in Example 2 above.

The above composition may be manufactured using the process described below.

Phase A consisting of water, aminomethyl propanol (AMP) and acrylic acid/VP crosspolymer: First, a vessel is charged with water and heated to 35° C. Then, 10% of the total amount of AMP needed is added. Acrylic acid/VP copolymer is then added with high agitation and mixed for at least 1 hour. Phase B consisting of a mixture of halogenated monomer, octyldodeceth-20 and fragrance: In a separate vessel, octyldodeceth-20 is warmed to 35° C. The halogenated monomer and fragrance are then added to the vessel. The contents are mixed until homogeneous. Phase B is added to Phase A and they are mixed until homogeneous. The mixture is then homogenized to reduce the particle size, then mixed slowly with a pitched blade propeller and allowed to deaerate. Phase C consisting of the reaming AMP and a preservative: Phase C is then added to the above mixture of Phase A and Phase B and mixed for 1 hour. The mixture is then cooled to 21° C.-25° C.

Example 19

Styling Cream

An exemplary styling cream containing a halogenated monomer may include:

| Ingredients | % w/w |
|---|---|
| Water | q.s. |
| Myristyl Alcohol | 0.00-5.00 |
| Cetyl Alcohol | 0.00-5.00 |
| Cetearyl Alcohol | 0.00-5.00 |
| Behenyl alcohol | 0.00-5.00 |
| Glyceryl Stearate | 0.00-2.00 |
| VP/VA Copolymer | 0.00-15.00 |
| VP/Dimethylaminoethyl Methacrylate Copolymer | 0.00-15.00 |
| VP/Acrylates/Lauryl Methacrylate Copolymer | 0.00-15.00 |
| Ceteareth-20 | 0.00-6.00 |
| Ceteth-10 | 0.00-6.00 |
| PEG-100 Stearate | 0.00-3.50 |
| PEG-40 Stearate | 0.00-3.50 |
| Polyacrylate-13 | 0.00-4.00 |
| Acrylamide/Sodium Acryloyldimethyltaurate Copolymer | 0.00-4.00 |
| Isohexadecane | 0.00-5.00 |
| Polyisobutene | 0.00-5.00 |
| Polysorbate 80 | 0.00-6.00 |
| Polysorbate 20 | 0.00-6.00 |
| Sorbitan Oleate | 0.00-4.00 |
| Ethylhexyl Stearate | 0.00-10.00 |
| PPG-2 Myristyl Propionate | 0.00-10.00 |
| PPG-3 Benzyl Ether Myristate | 0.00-10.00 |
| Hydroxypropyltrimonium Hydrolyzed Corn Starch | 0.00-5.00 |
| Carbomer | 0.00-1.00 |
| Triethanolamine | 0.00-0.75 |
| Preservative | 0.00-2.00 |
| Fragrance | 0.00-4.00 |
| Halogenated Monomer | 0.10-20.00 |

The halogenated monomer is as described in Example 2 above.

Example 20

Styling Pomade

An exemplary styling pomade containing a halogenated monomer may include:

| Ingredients | % w/w |
|---|---|
| Water | q.s. |
| Behenyl Alcohol | 0.00-10.00 |
| Cetearyl Alcohol | 0.00-10.00 |
| Linoleum Acid | 0.00-10.00 |
| Oleth-20 | 0.00-6.00 |
| Oleth-2 | 0.00-6.00 |
| PEG-8 Beeswax | 0.00-3.50 |
| Capric/Caprylic Triglyceride | 0.00-5.00 |
| Polyquaternium-46 | 0.00-10.00 |
| PVP | 0.00-10.00 |
| Preservative | 0.00-2.00 |
| Fragrance | 0.00-4.00 |
| Halogenated Monomer | 0.10-20.00 |

The halogenated monomer is as described in Example 2 above.

Example 21

Aerosol Hair Styling Spray

An exemplary aerosol hair styling spray containing a halogenated monomer may include:

| Ingredients | % w/w |
|---|---|
| Water | q.s. |
| Propellant | 2.00-80.00 |
| Alcohol (e.g. ethanol) | 0.00-55.00 |
| Polysorbate 20 | 0.00-6.00 |
| PEG-40 Hydrogenated Castor Oil | 0.00-6.00 |
| Oleth-20 | 0.00-6.00 |
| VP/VA Copolymer | 0.00-15.00 |
| Fragrance | 0.00-4.00 |
| Preservative | 0.00-2.00 |
| Halogenated Monomer | 0.10-20.00 |

The halogenated monomer is as described in Example 2 above.

Example 22

Aerosol Hair Styling Mousse

An exemplary aerosol hair styling mousse containing a halogenated monomer may include:

| Ingredients | % w/w |
| --- | --- |
| Water | q.s. |
| Propellant | 1.00-10.00 |
| Cocamidopropylbetaine | 0.00-5.00 |
| Lauramide Oxide | 0.00-2.00 |
| Trideceth-12 | 0.00-5.00 |
| PEG-8 Stearate | 0.00-0.50 |
| Halogenated Monomer | 0.10-20.00 |

The halogenated monomer is as described in Example 2 above.

Example 23

Aerosol Shave Cream

An exemplary aerosol shave cream containing a halogenated monomer may include:

| Ingredients | % w/w |
| --- | --- |
| Water | q.s. |
| Fatty Acid | 2.00-15.00 |
| Triethanolamine | 1.00-15.00 |
| Propellant | 2.00-6.00 |
| Laureth-23 | 0.00-2.00 |
| Hydroxyethylcellulose | 0.00-1.00 |
| Xanthan Gum | 0.00-1.00 |
| PEG-150 Distearate | 0.00-0.75 |
| Fragrance | 0.00-2.00 |
| Preservative | 0.00-1.50 |
| Halogenated Monomer | 0.10-20.00 |

The halogenated monomer is as described in Example 2 above.

Example 24

Aerosol Shave Gel

An exemplary aerosol shave gel containing a halogenated monomer may include:

| Ingredients | % w/w |
| --- | --- |
| Water | q.s. |
| Fatty Acid | 0.00-10.00 |
| Sarcosinate Acid | 0.00-10.00 |
| Triethanolamine | 0.00-10.00 |
| Propellant | 2.00-5.00 |
| Glyceryl Oleate | 0.00-4.00 |
| Hydroxyethylcellulose | 0.00-1.50 |
| PEG-90M | 0.00-0.75 |
| Fragrance | 0.00-2.00 |
| Preservative | 0.00-1.50 |
| Halogenated Monomer | 0.10-20.00 |

The halogenated monomer is as described in Example 2 above.

Example 25

Shave Cream

An exemplary shave cream containing a halogenated monomer may include:

| Ingredients | % w/w |
| --- | --- |
| Water | q.s. |
| Fatty Acid | 2.00-15.00 |
| Potassium Hydroxide | 0.50-10.00 |
| Sodium Lauryl Sarcosinate | 0.00-5.00 |
| Hydroxyethylcellulose | 0.00-2.00 |
| Hydroxypropylcellulose | 0.00-2.00 |
| Oleth-20 | 0.00-4.00 |
| Laureth-23 | 0.00-4.00 |
| PEG-24M | 0.00-1.00 |
| Fragrance | 0.00-2.00 |
| Preservative | 0.00-1.50 |
| Halogenated Monomer | 0.10-20.00 |

The halogenated monomer is as described in Example 2 above.

Example 26

Styling Spray

An exemplary styling spray containing a halogenated monomer may include:

| Ingredients | % w/w |
| --- | --- |
| Denatured Alcohol | 55.0% w/w |
| Water | 38.92% w/w |
| Halogenated Monomer | 2% w/w |
| PEG-40 Hydrogenated Castor Oil | 0.15% w/w |
| Fragrance | 0.50% w/w |
| $C_{10-40}$ Isoalkylamidopropyl ethyldimonium Ethosulfate | 0.25% w/w |
| Dipropylene Glycol | 0.38% w/w |

The halogenated monomer is as described in Example 2 above.

The above composition may be manufactured using the process described below.

Phase A consisting of denatured alcohol and water: First, a vessel is charged with water. Then, denatured alcohol is added to the charged vessel. The contents are mixed until homogeneous Phase A is obtained. Phase B consisting of a mixture of the halogenated monomer, PEG-40 hydrogenated castor oil and fragrance: In a separate vessel, PEG-40 hydrogenated castor oil is warmed to 30° C. The halogenated monomer and fragrance are then added to the vessel. The contents are mixed until homogeneous Phase B is obtained. Phase B is added to Phase A and they are mixed until homogeneous. Phase C consisting of $C_{10-40}$ isoalkylamidopropyl ethyldimonium ethosulfate and dipropylene glycol: Phase C is added to the above mixture of Phase A and Phase B until a homogeneous composition above is obtained.

Example 27

Styling Spray

An exemplary styling spray containing a halogenated monomer may include:

| | |
|---|---|
| Denatured Alcohol | 55.50% w/w |
| Water | 37.47% w/w |
| VP/Vinyl Caprolactam/DMAPA Acrylates Copolymer | 3.75% w/w |
| Halogenated Monomer | 2.00% w/w |
| PEG-40 Hydrogenated Castor Oil | 0.15% w/w |
| Fragrance | 0.50% w/w |
| $C_{10\text{-}40}$ Isoalkylamidopropyl ethyldimonium Ethosulfate | 0.25% w/w |
| Dipropylene Glycol | 0.38% w/w |

The halogenated monomer is as described in Example 2 above.

The above composition may be manufactured using the process described below.

Phase A consisting of denatured alcohol and water: First, a vessel is charged with water. Then, denatured alcohol is added to the charged vessel. The contents are mixed until homogeneous Phase A is obtained. Phase B consisting of a mixture of the halogenated monomer, PEG-40 hydrogenated castor oil and fragrance: In a separate vessel, PEG-40 hydrogenated castor oil is warmed to 30° C. The halogenated monomer and fragrance are then added to the vessel. The contents are mixed until homogeneous Phase B is obtained. Phase B is added to Phase A and they are mixed until homogeneous. Phase C consisting of $C_{10\text{-}40}$ isoalkylamidopropyl ethyldimonium ethosulfate and dipropylene glycol:: Phase C is added to the above mixture of Phase A and Phase B until homogeneous composition above is obtained.

Example 28

Styling Cream

An exemplary styling cream containing a halogenated monomer may include:

| | |
|---|---|
| Water | 93.35% w/w |
| Myristyl Alcohol | 1.00% w/w |
| PEG-8 Stearate | 0.50% w/w |
| Polysorbate 20 | 0.08% w/w |
| Polyacrylate-13 | 1.00% w/w |
| Polyisobutene | 0.50% w/w |
| PPG-2 Myristyl Ether Propionate | 0.50% w/w |
| Phenoxyethanol | 0.50% w/w |
| Caprylyl Glycol | 0.20% w/w |
| Sorbic Acid | 0.05% w/w |
| Halogenated Monomer | 2.00% w/w |
| Fragrance | 0.30% w/w |

The halogenated monomer is as described in Example 2 above.

The above composition may be manufactured using the process described below.

Phase A consisting of water: First, a vessel is charged with water. Then, the vessel is heated to 50° C. Phase B consisting of a mixture of myristyl alcohol, PEG-8 stearate, polysorbate 20, polyacrylate-13 and polyisobutene: Phase B ingredients are added to Phase A, allowing myristyl alcohol and PEG-8 stearate to melt before adding polysorbate 20, polyacrylate-13 and polyisobutene. The contents are mixed with high agitation for 30 minutes or until homogeneous. Phase C consisting of PPG-2 myristyl ether propionate is added to the above mixture of Phase A and Phase B and the contents are mixed until homogeneous. The mixture is cooled to 45° C. Then Phase D consisting of phenoxyethanol, caprylyl glycol and sorbic acid is added to the above mixture and the contents are mixed until homogeneous. The mixture is cooled to 30° C. Then Phase E consisting of the halogenated monomer and fragrance is added to the above mixture and the contents are mixed until homogeneous. Then water is added q.s. to the mixture and homogenized to obtain the above composition.

Example 29

Styling Cream

An exemplary styling cream containing a halogenated monomer may include:

| | |
|---|---|
| Water | 93.05% w/w |
| Cetyl Alcohol | 0.80% w/w |
| Polysorbate 20 | 0.10% w/w |
| Polyacrylate-13 | 1.10% w/w |
| Polyisobutene | 0.60% w/w |
| Octyl Stearate | 1.25% w/w |
| Phenoxyethanol | 0.50% w/w |
| Caprylyl Glycol | 0.20% w/w |
| Sorbic Acid | 0.05% w/w |
| Halogenated Monomer | 2.00% w/w |
| Fragrance | 0.35% w/w |

The halogenated monomer is as described in Example 2 above.

The above composition may be manufactured using the process described below.

Phase A consisting of water: First, a vessel is charged with water. Then, the vessel is heated to 60° C. Phase B consisting of a mixture of cetyl alcohol, polysorbate 20, polyacrylate-13 and polyisobutene: Phase B ingredients are added to Phase A, allowing cetyl alcohol to melt before adding polysorbate 20, polyacrylate-13 and polyisobutene. The contents are mixed with high agitation for 30 minutes or until homogeneous. Phase C consisting of octyl stearate is added to the above mixture of Phase A and Phase B until homogeneous. The mixture is cooled to 45° C. Then Phase D consisting of phenoxyethanol, caprylyl glycol and sorbic acid is added to the above mixture and the contents are mixed until homogeneous. The mixture is cooled to 30° C. Then Phase E consisting of the halogenated monomer and fragrance is added to the above mixture and the contents are mixed until homogeneous. Then water is added q.s. to the mixture and homogenized to obtain the above composition.

Example 30

Hair Styling Control Cream

An exemplary hair styling control cream containing a halogenated monomer may include:

| | |
|---|---|
| Water | 76.30% w/w |
| VP/VA Copolymer | 6.00% w/w |
| VP/Dimethylaminoethyl methacrylate Copolymer | 10.00% w/w |
| Myristyl Alcohol | 1.00% w/w |
| PEG-8 Stearate | 0.50% w/w |
| Polysorbate 20 | 0.08% w/w |

-continued

| | |
|---|---|
| Polyacrylate-13 | 1.00% w/w |
| Polyisobutene | 0.50% w/w |
| PPG-2 Myristyl Ether Propionate | 0.50% w/w |
| Phenoxyethanol | 0.50% w/w |
| Caprylyl Glycol | 0.20% w/w |
| Sorbic Acid | 0.05% w/w |
| Halogenated Monomer | 2.00% w/w |
| Glycerin | 1.00% w/w |
| Fragrance | 0.35% w/w |

The halogenated monomer is as described in Example 2 above.

The above composition may be manufactured using the process described below.

Phase A consisting of water, VP/VA copolymer, and VP/dimethylaminoethyl methacrylate copolymer: First, a vessel is charged with water. Then, VP/VA copolymer, and VP/dimethylaminoethyl methacrylate copolymer are added to the vessel. The vessel is then heated to 50° C. Phase B consisting of a mixture of myristyl alcohol, PEG-8 stearate, polysorbate 20, polyacrylate-13 and polyisobutene: Phase B ingredients are added to Phase A, allowing myristyl alcohol and PEG-8 stearate to melt before adding polysorbate 20, polyacrylate-13 and polyisobutene. The contents are mixed with high agitation for 30 minutes or until homogeneous. Phase C consisting of PPG-2 myristyl ether propionate is added to the above mixture of Phase A and Phase B until homogeneous. The mixture is cooled to 45° C. Then Phase D consisting of phenoxyethanol, caprylyl glycol and sorbic acid is added to the above mixture and the contents are mixed until homogeneous. The mixture is cooled to 30° C. Then Phase E consisting of the halogenated monomer, glycerin and fragrance is added to the above mixture and the contents are mixed until homogeneous. Then water is added q.s. to the mixture and homogenized to obtain the above composition.

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A composition for treating scalp hair comprising a non-polymeric fluorinated ester having the following terminal fluorinated alkyl moiety:

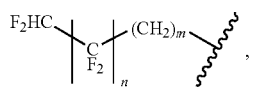

and a cosmetically acceptable excipient,
wherein n is an integer between 0 and 20 and m is an integer between 1 and 6, and having a molecular weight less than about 1500 g/mol, and
wherein the composition does not contain a free radical initiator, a polymerization initiator or a polymerization catalyst.

2. The composition according to claim 1, wherein the fluorinated ester is present in the composition in a range of 0.1% to 20% w/w.

3. The composition according to claim 1, wherein the fluorinated ester is

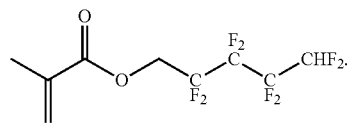 [SMILES: C=C(C)C(=O)OCC(F)(F)C(F)(F)C(F)(F)C(F)F]

4. The composition according to claim 1, wherein the composition is a shampoo, conditioner, hair spray, styling cream or styling spray.

5. A method for treating scalp hair comprising applying to scalp hair a composition comprising a non-polymeric fluorinated ester having the following terminal fluorinated alkyl moiety:

and a cosmetically acceptable excipient,
wherein n is an integer between 0 and 20 and m is an integer between 1 and 6, and having a molecular weight less than about 1500 g/mol, and
wherein the method does not employ a free radical initiator, a polymerization initiator or a polymerization catalyst.

6. The method according to claim 5, wherein the method does not have a rinsing step.

7. The method according to claim 5, wherein the fluorinated ester is present in the composition in a range of 0.1% to 20% w/w.

8. The method according to claim 5, wherein the fluorinated ester is

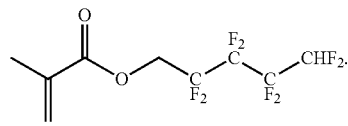 [SMILES: C=C(C)C(=O)OCC(F)(F)C(F)(F)C(F)(F)C(F)F]

9. The method according to claim 5, wherein the composition is a shampoo, conditioner, hair spray, styling cream or styling spray.

* * * * *